US007432045B2

(12) United States Patent
Brandt et al.

(10) Patent No.: US 7,432,045 B2
(45) Date of Patent: Oct. 7, 2008

(54) METHOD OF INHIBITING INFLUENZA INFECTION WITH ANTIVIRAL PEPTIDES

(75) Inventors: Curtis R. Brandt, Stoughton, WI (US); Hermann Bultmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 195 days.

(21) Appl. No.: 11/001,674

(22) Filed: Dec. 1, 2004

(65) Prior Publication Data

US 2005/0203024 A1 Sep. 15, 2005

Related U.S. Application Data

(60) Provisional application No. 60/526,252, filed on Dec. 1, 2003.

(51) Int. Cl.
*C12Q 1/70* (2006.01)
*A61K 38/00* (2006.01)
*A61K 39/145* (2006.01)

(52) U.S. Cl. .................... 435/5; 530/326; 424/209.1

(58) Field of Classification Search ................. None
See application file for complete search history.

(56) References Cited

U.S. PATENT DOCUMENTS

| 4,795,740 A | 1/1989 | Cohen et al. |
| 5,104,854 A | 4/1992 | Schlesinger et al. |
| 5,182,265 A | 1/1993 | Bruzzese et al. |
| 5,260,420 A | 11/1993 | Burnouf-Radosevich et al. |
| 5,380,727 A | 1/1995 | Dëziel et al. |
| 5,441,936 A | 8/1995 | Houghten et al. |
| 5,645,849 A | 7/1997 | Pruss et al. |
| 5,700,780 A | 12/1997 | Beaulieu et al. |
| 5,877,282 A | 3/1999 | Nadler et al. |

FOREIGN PATENT DOCUMENTS

| EP | 0 531 080 A2 | 3/1993 |
| FR | 2739621 | 4/1997 |
| JP | 4-21635 | 1/1992 |
| WO | WO 99/05302 | 2/1999 |
| WO | WO 99/64449 | 12/1999 |
| WO | WO 01/57072 | 8/2001 |
| WO | WO 01/57072 A2 * | 8/2001 |

OTHER PUBLICATIONS

Jones et al. Journal of Virology, Dec. 2006, 80(24):11960-11967.*
Aldrian-Herrada, G. et al., "A peptide nucleic acid (PNA) is more rapidly internalized in cultured neurons when coupled to a retro-inverso delivery peptide. The antisense activity depresses the target mRNA and protein in magnocellular oxytocin neurons." *Nucleic Acids Res*, 26: 4910-4916, 1998; Oxford University Press.
Banfield, B. W. et al., "Evidence for an interaction of herpes simplex virus chondroitin sulfate proteoglycans during infection." *Virology* 208: 531-539, 1995; Academic Press, Inc.

Berkowitz, B. A. et al., "Magainins: A new family of membrane-active host defense peptides." *Biochem. Pharmacol.* 39: 625-629, 1990; Pergamon Press.
Böcher, B. et al., "Peptides that Block Hepatitis B Virus Assembly: Analysis by Cryomicroscopy, Mutagenesis and Transfection." *The EMBO Journal* 17(23): 6839-6845, 1998; Oxford University Press.
Boulikas, T., "Nuclear Localization Signals (NLS)." *Critical Reviews in Eukaryotic Gene Expression*, 3(3) pp. 193-227, 1993; CRC Press, Inc.
Brandt, C. R. et al., "A murine model of herpes simplex virus-induced ocular disease for antiviral drug testing." *J. Virol. Methods.* 36: 209-222, 1992; Elsevier Science Publishers B.V.
Brandt, C. R. et al., "Evaluation of a peptidomimetic ribonucleotide reductase inhibitor with a murine model of herpes simplex virus type 1 ocular disease." *Antimicrob. Agents Chemother.* 40: 1078-1084, 1996; American Society for Microbiology.
Brandt, C. R. et al., "Inhibition of HSV ocular infection by membrane transiisting peptides." *Investigative Ophthalmology and Visual Science*, vol. 42, No. 4, p. S108, 2000; Association for Research in Vision and Ophthalmology; Assoc. Research Vision Opthalmology Inc.
Brugidou, J. et al., "The *Retro inverso* Form of a Homeobox-Derived Short Peptide is Rapidly Internalized by Cultured Neurones: A New Basis for an Efficient Intracellular Delivery System." *Biochemical and Biophysical Research Communications* 214(2): 685-693, 1995; Academic Press Inc.
Bultmann, H. et al., "Modified FGF4 signal peptide inhibits entry of herpes simplex virus type 1." *J. Virol.* 75: 2634-2645, 2001; American Society for Microbiology.
Bultmann, H. et al., "Peptides containing membrane-transiting motifs inhibit virus entry." *J. Biol. Chem.* 277: 36018-36023, 2002; The American Society for Biochemistry and Molecular Biology, Inc.
Cai, W. et al., "Role of glycoprotein B of herpes simplex virus type I in viral entry and fusion." *J. Virol.* 62: 2598-2604, 1988; American Society for Microbiology.
Campadelli-Fiume, G. et al., "Glycoprotein C-dependent attachment of herpes simplex virus to susceptible cells leading to productive infection." *Virology* 178: 213-222, 1990.
Choudhury, I. et al., "Inhibition of HIV-1 Replication by a Test RNA-Binding Domain Peptide Analog." *Journal of Acquired Deficiency Syndromes and Human Retrovirology*, vol. 17, No. 2, pp. 104-111, Feb. 1, 1998; Lippincon-Raven Publishers (Philadelphia).
Cockrell, A. S. et al., "Herpes simplex virus type 2 UL45 is a type II membrane protein." *J. Virol.* 72: 4430-4433, 1998; American Society for Microbiology.
Coen, D. M. et al., "Fine mapping and molecular cloning of mutations in the herpes simplex virus DNA polymerase locus." *J. Virol.* 49: 236-247, 1984; American Society for Microbiology.

(Continued)

*Primary Examiner*—Stacy B Chen
(74) *Attorney, Agent, or Firm*—Foley & Lardner LLP

(57) ABSTRACT

This invention relates to peptides having antiviral properties. The antiviral peptides comprise membrane transiting peptides, and active fragments and derivatives of such peptides. The antiviral peptides exhibit activity against a broad spectrum of viruses, including enveloped and non-enveloped viruses, and are used in pharmaceutical compositions to prevent and/or treat viral infections.

30 Claims, 44 Drawing Sheets

OTHER PUBLICATIONS

Cohen, E. A. et al., "Specific inhibition of herpesvirus ribonucleotide reductase by a nonapeptide derived from the carboxy terminus of subunit 2." *Nature*, 321: 441-443, 1986.

Derossi, D. et al., "The third helix of the antennapedia homeodomain translocates through biological membranes" *J. Biol. Chem.* 269: 10444-10450, 1994; The American Society for Biochemistry and Molecular Biology, Inc.

Derossi, D. et al., "Cell internalization of the third helix of the antennapedia homeodomain is receptor-independent." *J. Biol. Chem.* 217: 18188-18193, 1996; The American Society for Biochemistry and Molecular Biology, Inc.

Derossi, D. et al., "Trojan peptides: the penetration system for intracellular delivery." *Trends Cell. Biol.* 8: 84-87, 1998; Elsevier Science Ltd.

Derossi, D., "Antennapedia Homeodomain Third Helix as a Peptide and Oligonucleotide Vector." *Restorative Neurology and Neuroscience 8*: 17-18, 1995; Elsevier Science Ireland Ltd.

Desai, P. J. et al., "Excretion of non-infectious virus particles lacking gH by a temperature-sensitive mutant of herpes simplex virus type I: Evidence that gH is essential for virion infectivity." *J. Gen. Virol.* 69: 1147-1156, 1988; SGM (Great Britain).

Du, C. et al., "Conformational and Topological Requirements of Cell-Permeable Peptide Function." *J. Peptide Res.* 51: 235-243, 1998; Munksgaard.

Dutia, B. et al., "Specific inhibition of herpesvirus ribonucleotide reductase by synthetic peptides." *Nature 321*: 439-441, 1986.

Elliott, G. et al., "Intercellular Trafficking and Protein Delivery by a Herpesvirus Structural Protein." *Cell 88*: 223-233, 1997; Cell Press.

Fawell, S. et al., "Tat-mediated delivery of heterologous proteins into cells." *Proc. Natl. Acad. Sci. USA 91*: 664-668, 1994.

Fields, C. G. et al., "HBTU activation for automated Fmoc solid-phase peptide synthesis." *Peptide Res. 4*: 95-101, 1991.

Flores, E. R. et al., "Establishment of the human papillomavirus type 16 (PHV-16) life cycle in an immortalized human foreskin keratinocyte cell line." *Virology 262*: 344-354, 1999; Academic Press.

Fuller, A. O. et al., "Anti-glycoprotein D antibodies that permit adsorption but block infection by herpes simplex virus 1 prevent virion-cell fusion at the cell surface." *Proc. Natl. Acad. Sci. USA 84*: 5454-5458, 1987.

Fuller, A. O. et al., "Herpes simplex virus type I entry through a cascade of virus-cell interactions requires different roles of gD and gH in penetration." *J. Virol. 66*: 5002-5012, 1992; American Society for Microbiology.

Gariepy, J. et al., "Vectorial delivery of macromolecules into cells using peptide-based vehicles." *Trends Biotechnol. 19*: 21-28, 2001; Elsevier Science Ltd.

Geraghty, R. J. et al., "Entry of alphaherpesviruses mediated by poliovirus receptor related protein 1 and poliovirus receptor." *Science 280*: 1618-1620, 1998.

Gibbs, J. S. et al., "Sequence and mapping analysis of the herpes simplex virus DNA polymerase gene predicts a c-terminal substrate binding domain." *Proc. Natl. Acad. Sci. USA 82*: 7969-7973, 1985.

Goldstein, D. J. et al., "Factor(s) present in herpes simplex virus type 1-infected cells can compensate for the loss of the large subunit of the viral ribonucleotide reductase: characterization of an ICP6 deletion mutant." *Virology 166*: 41-51, 1988; Academic Press, Inc.

Grau, D. R. et al., "Herpes simplex virus stromal keratitis is not titer-dependent and does not correlate with neurovirulence." *Invest. Ophthalmol. Vis. Sci.* 30: 2474-2480, 1989; Association for Research in Vision and Ophthalmology.

Haanes, E. J. et al., "The UL45 gene product is required for herpes simplex virus type 1 glycoprotein B-induced fusion." *J. Virol.* 68: 5825-5834, 1994; American Society for Microbiology.

Hall, J. D. et al., "Aphidicolin resistance in herpes simplex virus type 1 appears to alter substrate specificity in the DNA polymerase." *J. Virol.* 63: 2874-2876, 1989; American Society for Microbiology.

Handler, C. G. et al., "Cross-linking of glycoprotein oligomers during herpers simplex virus type 1 entry." *J. Virol.* 70: 6076-6082, 1996; American Society for Microbiology.

Hawiger, J., "Noninvasive intracellular delivery of functional peptides and proteins." *Curr. Opin. Chem. Biol.* 3: 89-94, 1999.

Herold, B. C. et al., "Glycoprotein C of herpes simplex virus type 1 plays a principal role in the adsorption of virus to cells and in infectivity." *J. Virol.* 65: 1090-1098, 1991; American Society for Mirobiology.

Herold, B. C. et al., "Glycoprotein C-independent binding of herpes simplex virus to cells requires cell surface heparan sulphate and glycoprotein B." *J. Gen. Virol.* 75: 1211-1222, 1994; SGM (Great Britain).

Herold, B. C. et al., "Differences in the susceptibility of Herpes simplex virus types 1 and 2 to modified heparan compounds suggest serotype differences in viral entry." *J. Virol.* 70: 3461-3469, 1996; American Society for Microbiology.

Highlander, S. et al., "Neutralizing monoclonal antibodies specific for herpes simplex virus glycoprotein D inhibit virus penetration." *J. Virol.* 61: 3356-3364, 1987; American Society for Microbiology.

Hong, S. Y. et al., "Identification and Characterization of Novel Antimicrobial Decapeptides Generated by Combinatorial Chemistry." *Antimicrobial Agents and Chemotherapy 42*(10): 2534-2541, 1998; American Society for Microbiology.

Hutchinson, L. et al., "A novel herpes simplex virus glycoprotein, gL, forms a complex with glycoprotein H (gH) and affects normal folding and surface expression of gH." *J. Virol.* 66: 2240-2250, 1992; American Society for Microbiology.

Janek, K. et al., "Water-Soluble β-Sheet Models Which Self-Assemble into Fibrillar Structures." *Biochemistry*, vol. 38, No. 26, pp. 8246-8252, 1999; American Chemical Society.

Johnson, R. M. et al., "Herpes simplex virus glycoprotein D mediates interference with herpes simplex virus infection." *J. Virol.* 63: 819-827, 1989; American Society for Microbiology.

Kilby, M. J. et al., "Potent suppression of HIV-1 replication in humans by T-20, a peptide inhibitor of gp41-mediated virus entry." *Nature Med.* 4 (11): 1302-1307, 1998.

Knopf, C. W., "The herpes simplex virus type 1 DNA polymerase gene: Site of phosphonoacetic acid resistance mutation in strain Angelotti is highly conserved." *J. Gen. Virol.* 68: 1429-1433, 1987; SGM (Great Britain).

Krause, E. et al., "Conformation of a Water-Soluble β-Sheet Model Peptide." *Int. J. Peptide Protein Res.* 48:559-568, 1996; Munksgaard (UK).

Krummenacher, C. et al., "Herpes simplex virus glycoprotein D can bind to poliovirus receptor-related protein 1 or herpesvirus entry mediator, two structurally unrelated mediators of virus entry." *J. Virol.* 72: 7064-7074, 1998; American Society for Microbiology.

Laquerre, S. et al., "Heparan sulfate proteoglycan binding by herpes simplex virus type 1 glycoproteins B and C, which differ in their contributions to virus attachment, penetration, and cell to cell spread." *J. Virol.* 72: 6119-6130, 1998; American Society for Microbiology.

Ligas, M. W. et al., "A herpes simplex virus mutant in which glycoprotein D sequences are replaced by β-galactosidase sequences binds to, but is unable to penetrate into cells." *J. Virol.* 62: 1486-1494, 1988; American Society for Microbiology.

Lin, Y. -Z. et al., "Inhibition of nuclear translocation of transcription factor NF-κβ by a synthetic peptide containing a cell membrane-permeable motif and nuclear localization sequence." *J. Biol. Chem.* 270: 14255-14258, 1995; The American Society for Biochemistry and Molecular Biology, Inc.

Lycke, E. et al., "Binding of herpes simplex virus to cellular heparan sulfate, an initial step in the adsorption process." *J. Gen. Virol.* 72: 1131-1137, 1991; SGM (Great Britain).

Manservigi, R. et al., "Cell fusion induced by herpes simplex virus is promoted and suppressed by different viral glycoproteins." *Proc. Natl. Acad. Sci. USA* 74: 3913-3917, 1977.

Matthews, J. T. et al., "The structure and function of the HSV DNA replication proteins: Defining novel antiviral targets." *Antiviral Res.* 20: 89-114, 1993; Elsevier Science Publishers B.V.

Meienhofer, J. et al., "Solid phase synthesis without repetitive acidolysis: Preparation of leucyl-alanyl-glycyl-valine using 9-fluorenylmethyloxy-carbonylamino acids." *Int. J. Peptide Res.* 13: 35-42, 1979; Munksgaard (Copenhagen).

Merrifield, R. B., "Solid phase peptide synthesis I. The synthesis of a tetrapeptide." *J. Am. Chem. Soc.* 85: 2129-7154, 1963.

Minson, A. C. et al., "An analysis of the biological properties of monoclonal antibodies against glycoprotein D of herpes simplex virus and identification of amino acid substitutions that confer resistance to neutralization." *J. Gen. Virol.* 67: 1001-1013, 1986; SGM (Great Britain).

Montgomery, R. I. et al., "Herpes simplex virus-1 entry into cells mediated by a novel member of the TNF/NGF receptor family." *Cell* 87:427-436, 1996; Cell Press.

Nicola, A. V. et al., "Structure function analysis of soluble forms of herpes simplex virus glycoprotein D." *J. Virol.* 70: 3815-3822, 1996; American Society for Microbiology.

Nicola, A. V. et al., "Monoclonal antibodies to distinct sites on herpes simplex virus (HSV) glycoprotein D block HSV binding to HVEM." *J. Virol.* 72: 3595-3601, 1998; American Society for Microbiology.

Nisole, S. et al., "The anti-HIV pseudopeptide HB-19 forms a complex with cell-surface-expressed nucleolin independent of heparan sulfate proteoglycans." *J. Biol. Chem.* 274: 27875-27884, 1999; The American Society for Biochemistry and Molecular Biology, Inc.

O'Brien, W. A. et al., "Anti-Human Immunodeficiency Virus Type 1 Activity of an Oligocationic Compound Mediated via gp 120 V3 Interactions," *Journal of Virology*, vol. 70, No. 5, pp. 2825-2831, 1996; American Society for Microbiology.

Oehlke, J. et al., "Cellular uptake of an α-helical amphipathic model peptide with the potential to deliver polar compounds into cell interior non-endocytically." *Biochimica et Biophysica Acta 1414*, pp. 127-139, 1998; Elsevier Science BV.

Oehlke, J. et al., "Nonendocytic, amphipathicity dependent cellular uptake of helical model peptides." *Protein Peptide Lett.* 3: 393-398, 1996; Bentham Science Publishers B.V.

Oehlke, J. et al., "Extensive cellular uptake into endothelial cells of an amphipathic β-sheet forming peptide." *FEBS Lett.* 415: 196-199, 1997; Federation of European Biochemical Societies.

Oehlke, J. et al., "Utilization of Endothelial Cell Monolayers of Low Tightness for Estimation of Transcellular Transport Characteristics of Hydrophilic Compounds." *Euro. J. Pharm.* 2: 365-372, 1994; Elsevier Science B.V.

Phelan, A. et al., "Intercellular Delivery of Functional p53 by the Herpesvirus Protein VP22." *Nature Biotechnology 16*: 440-443, 1998.

Pooga, M. et al., "Cell penetration by transportan." *FASEB J.* 12: 67-77, 1998; FASEB.

Rimsky, L. T. et al., "Determinants of human immunodeficiency virus type 1 resistance to gp41-derived inhibitory peptides." *J. Virol.* 72 (2): 986-993, 1998; American Society for Microbiology.

Rojas, M. et al., "Genetic Engineering of Proteins with Cell Membrane Permeability," *Nature Biotechnology 16*: 370-375, 1998.

Roop, C. et al., "A mutant herpes simplex virus type 1 unable to express glycoprotein L. cannot enter cells and its particles lack glycoprotein H." *J. Virol.* 67: 2285-2297, 1993; American Society for Microbiology.

Rothemund, S. et al., "Recognition of α-Helical Peptide Structures Using High-Performance Liquid Chromatographic Retention Data for D-Amino Acid Analogues: Influence of Peptide Amphipathicity and of a Stationary Phase Hydrophobicity," *Journal of Chromatography A 689*: 219-226, 1995; Elsevier Science B.V.

Sasadeusz, J. J. et al., "Homopolymer mutational hot spots mediate herpes simplex virus resistance to acyclovir." *J. Virol.* 71: 3872-3878, 1997; American Society for Microbiology.

Schwarze, S. R. et al., "In vivo protein transduction: Delivery of a biologically active protein into the mouse." *Science 285*: 1569-1572, 1999.

Schwarze, S. R. et al., "Protein transduction: unrestricted delivery into all cells." *Trends Cell Biol.* 10: 290-295, 2000; Elsevier Science Ltd.

Sears, A. E. et al., "Infection of polarized MDCK cells with herpes simplex virus 1: Two asymmetrically distributed cell receptors interact with different viral proteins." *Proc. Natl. Acad. Sci.* USA 88: 5087-5091, 1991.

Shieh, M. T. et al., "Cell surface receptors for herpes simplex virus are heparan sulfate proteoglycans." *J. Cell Biol.* 116: 1273-1281, 1992; The Rockefeller University Press.

Shieh, M.-T. et al., "Herpes virus-induced cell fusion that is dependent on cell surface heparan sulfate or soluble heparan." *J. Virol.* 68: 1224-1228, 1994; American Society for Microbiology.

Spear, P. G., "Entry of alphaherpesviruses into cells." *Sem. Virol.* 4: 167-180, 1993; Academic Press Ltd.

Srinivas, R. V. et al., "Antiviral effects of apolipoprotein A-I and its synthetic amphipathic peptide analogs." *Virology 176*: 48-57, 1990; Academic Press, Inc.

Srinivas, S. K. et al., "Membrane interactions of synthetic peptides corresponding to amphipathic helical segments of the human immunodeficiency virus type-1 envelope glycoprotein." *J. Biol. Chem.* 267(10): 7121-7127, 1992; The American Society for Biochemistry and Molecular Biology, Inc.

Stephens, D. J. et al., "The many ways to cross the plasma membrane." *Proc. Natl. Acad. Sci USA 98*, 4295-4298, 2001.

Tal-SInger, R. et al., "Interaction of herpes simplex virus glycoprotein C with mammalian cell surface molecules." *J. Virol.* 69: 4471-4483, 1995; American Society for Microbiology.

Théodore, L. et al., "Intraneuronal delivery of protein kinase C pseudosubstrate leads to growth cone collapse." *J. Neurosci.* 15: 7158-7167, 1995; Society for Neuroscience.

Turner, A. et al., "Glycoproteins gB, gD, and gHgL of herpes simplex virus type I are necessary and sufficient to mediate membrane fusion in a Cos cell transfection system." *J. Virol.* 72: 873-875, 1998; American Society for Microbiology.

Visalli, R. J. et al., "The HSV-1 UL45 18 kDa gene product is a true late protein and a component of the virion." *Virus Res.* 29: 167-178, 1993; Elsevier Science Publishers B.V.

Vivés, E. et al., "A truncated HIV-1 tat protein basic domain rapidly translocates through the plasma membrane and accumulates in the cell nucleus." *J. Biol. Chem.* 272: 16010-16017, 1997; The American Society for Biochemistry and Molecular Biology, Inc.

Vivés, E. et al., "Structure-activity relationship study of the plasma membrane translocating potential of a short peptide from HIV-1 tat protein." *Lett. Pept. Sci.* 4: 429-436, 1997; Kluwer Academic Publishers (Netherlands).

Westra, D. F. et al., "Glycoprotein H of herpes simplex virus type 1 requires glycoprotein L for transport to the surfaces of insect cells." *J. Virol.* 7: 2285-2291, 1997; American Society for Microbiology.

Whitbeck, J. C. et al., "Glycoprotein D of herpes simplex virus (HSV) binds directly to HVEM, a member of the tumor necrosis factor receptor superfamily and a mediator of HSV entry." *J. Virol.* 71: 6083-6093, 1997; American Society for Microbiology.

White, J., "Membrane fusion." *Science 258*: 917-923, 1992.

Whitley, R. J., "Epidemiology of herpes simplex viruses," *The Herpesviruses—vol. 3*, B. Roizman (ed.), 1-44, 1982; Plenum Press (New York).

Wild, C. et al., "Peptides Corresponding to a Predictive α-Helical Domain of Human Immunodeficiency Virus Type 1 gp41 are Potent Inhibitors of Virus Infection." *Proc. Nat'l. Acad. Sci. USA 91*: 9770-9774, 1994.

Wild, C. et al., "Propensity for a Leucine Zipper-Like Domain of Human Immunodeficiency Virus Type 1 gp41 to Form Oligomers Correlates with a Role in Virus-Induced Fusion Rather than Assembly of the Glycoprotein Complex." *Proc. Nat'l. Acad. Sci. USA 91*: 12676-12680, 1994.

Wild, C. et al., "A synthetic peptide inhibtor of human immunodeficiency virus replication: Correlation between solution structure and viral inhibition." *Proc. Natl. Acad. Sci. USA 89*: 10537-10541, 1992.

WuDunn, D. et al., "Initial interaction of herpes simplex virus with cells is binding to heparan sulfate." *J. Virol.* 63: 52-58, 1989; American Society for Microbiology.

Yang, C. et al., "Analysis of the Murine Leukemia Virus R Peptide: Delineation of the Molecular Determinants Which are Important for Its Fusion Inhibition Activity." *Journal of Virology 71*(11): 8490-8496, 1997; American Society for Microbiology.

Yao, Q. et al., "Peptides corresponding to the heptad repeat sequence of human parainfluenza virus fusion protein are potent inhibitors of virus infection." *Virology 223*: 103-112, 1996; Academic Press, Inc.

Zhang, L. et al., "Preparation of functionally active cell-permeable peptides by single step ligation of two peptide modules." *Proc. Natl. Acad. Sci.*, vol. 95, pp. 9184-9189, Aug. 1998; The National Academy of Sciences.

International Search Report dated Oct. 27, 2005 for PCT/US2004/040119.

Rhoads, et al., "Alanine Enhances Jejunal Sodium Absorption in the Presence of Glucose: Studies in Piglet Viral Diarrhea," Pediatric Research, vol. 20, No. 9, 1986, pp. 879-883.

* cited by examiner

10 A.

10 B.

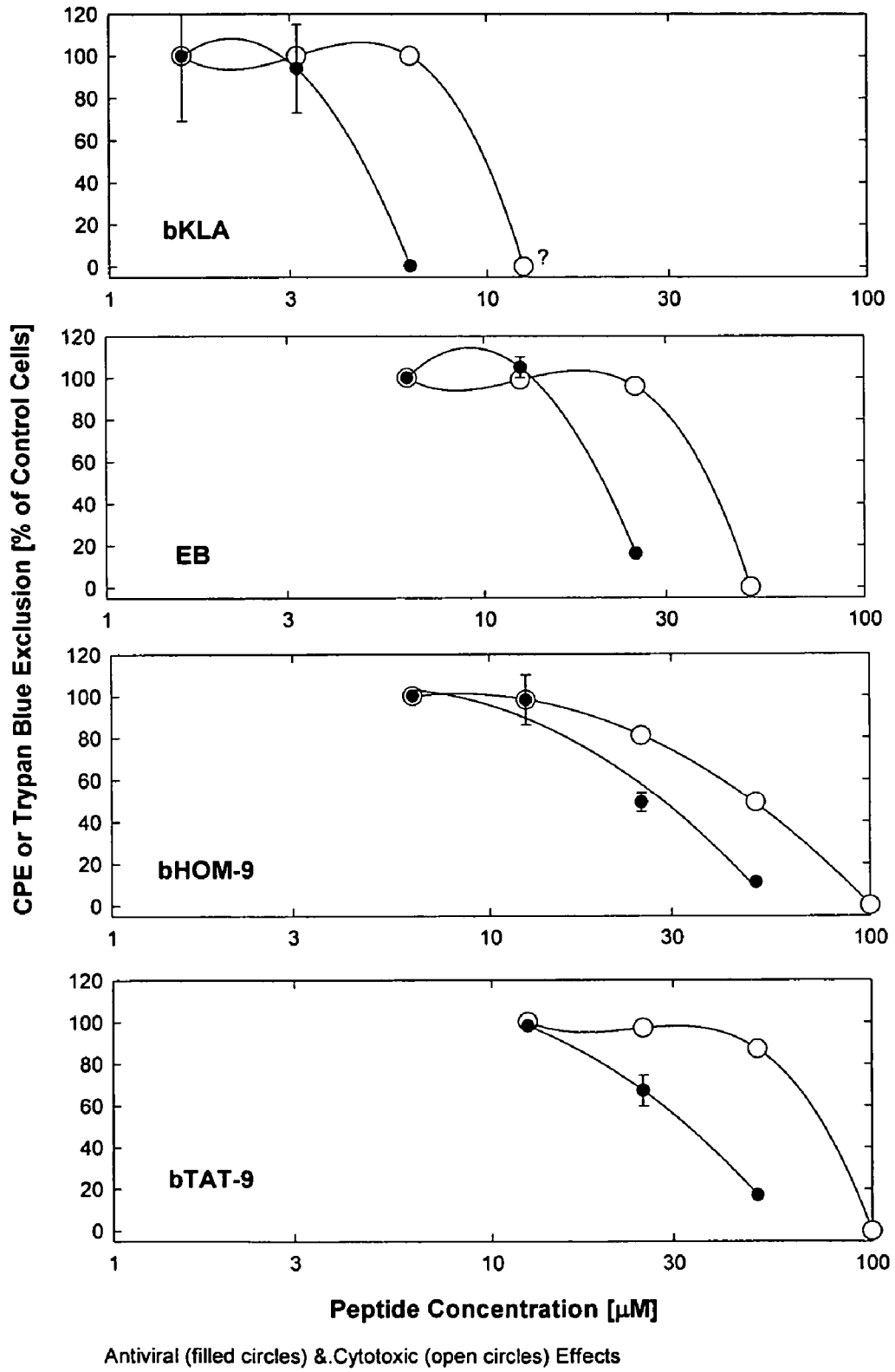
FIGS. 11A, 11B, 11C, and 11D

In vivo infectivity of influenza virus inactivated by EB or bKLA peptide

- □ No Peptide
- △ 6.1mM EB
- ○ 2.6mM bKLA

Y-axis: Survival [%]
X-axis: Days Postinfection

The bKLA peptide inhibits influenza virus in infected mice

- □ No Peptide
- ● 0.5mM bKLA delivered days 1 & 2 postinfection

Y-axis: Survival [%]
X-axis: Days Postinfection

FIGS. 13 and 14

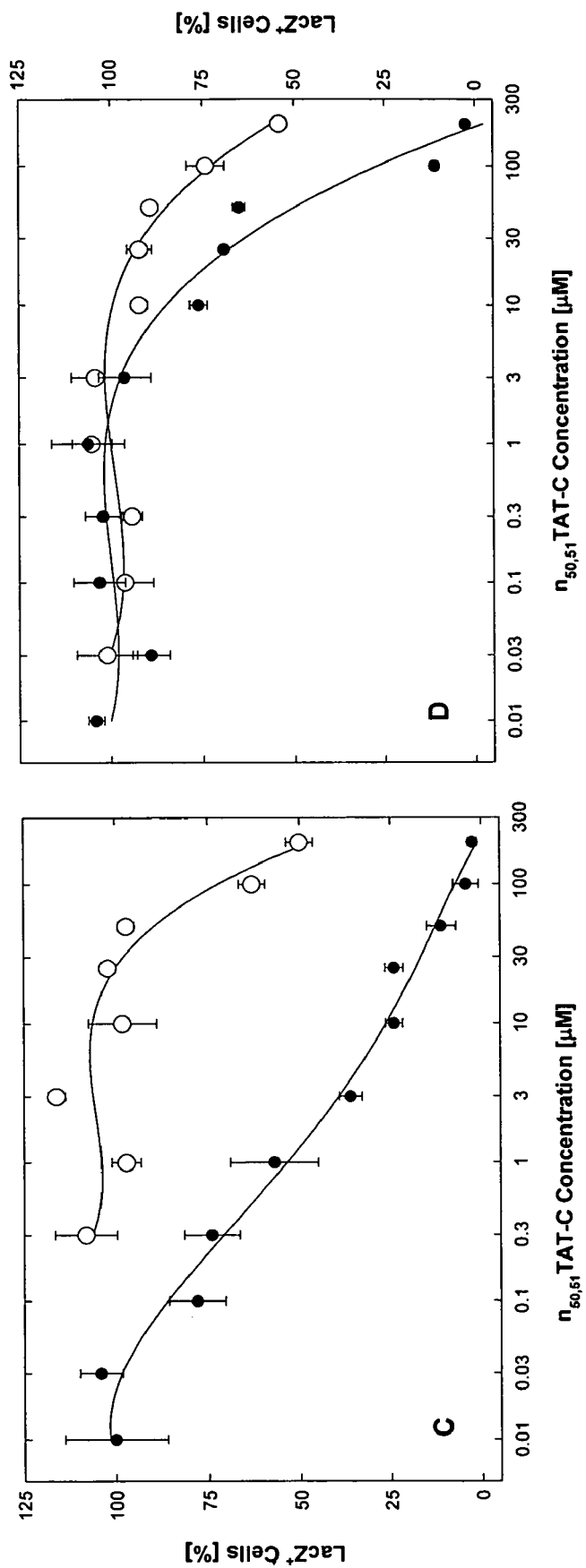
FIGS. 15C, and 15D

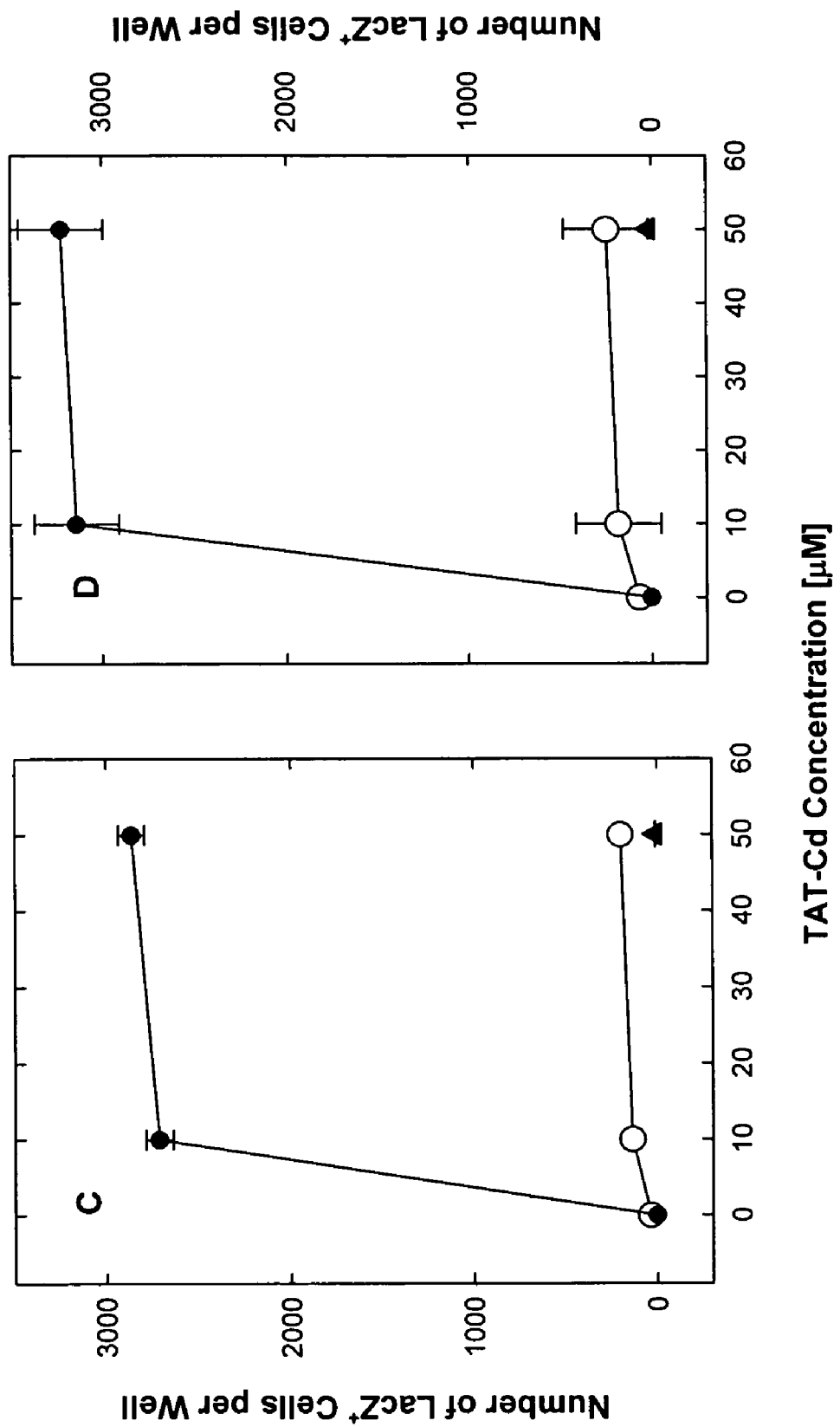
FIGS. 19C, and 19D

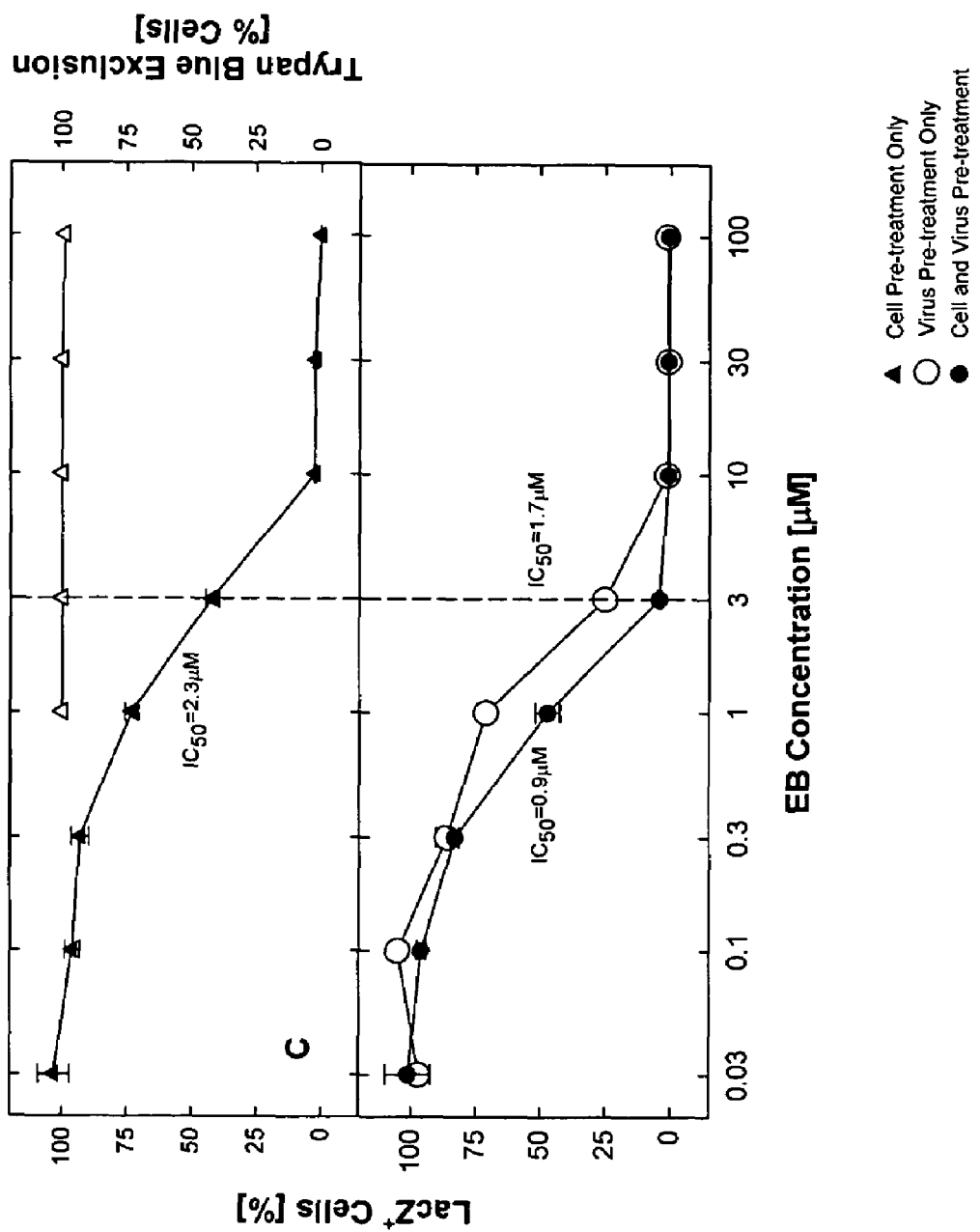
FIGS. 24C, and 24D

Curves (solid lines) are exponential rises to maxima (simple exponent, 2 parameters): $y=a(1-b^x)$ [did not seen any difference from $y=a(1-e^{-bx})$]

A: PBS
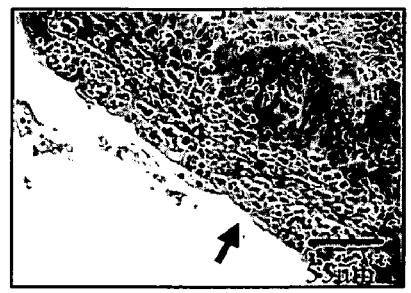
B: N-9 6.6%
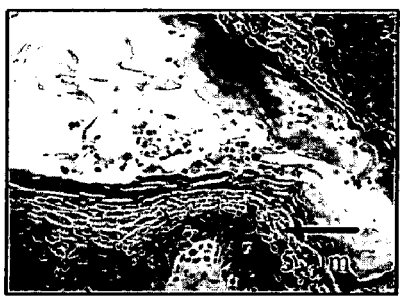
C: EB
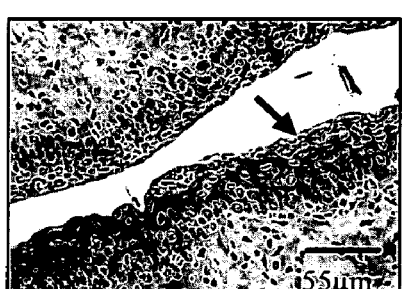
D: bHOMd
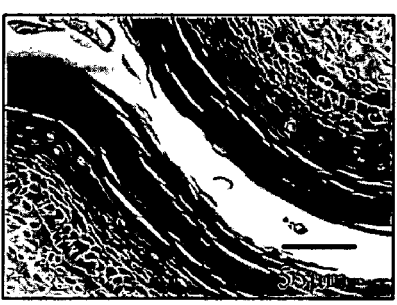
E: TAT-C

FIGS. 36A-E

SEQUENCE LISTING

<160> NUMBER OF SEQ ID NOS: 44

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Arg Lys Lys Ala Ala Val Ala Leu Leu Pro Ala Val Leu Leu Ala
 1               5                  10                  15

Leu Leu Ala Pro
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Arg Arg Lys Lys Ala Ala Val Ala Leu Leu Pro Ala Val Leu Leu Ala
 1               5                  10                  15

Leu Leu Ala Pro
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Arg Arg Lys Lys Ala Ala Val Ala Leu Leu Ala Val Leu Leu Ala Leu
 1               5                  10                  15

Leu Ala Pro Pro
            20

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Arg Arg Lys Lys Pro Ala Val Leu Leu Ala Leu Leu Ala
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Lys Leu Ala Leu Lys Leu Ala Leu Lys Ala Leu Lys Ala Ala Leu Lys
 1               5                  10                  15

Leu Ala

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Leu Ala Leu Lys Leu Ala Leu Lys Ala Leu Lys Ala Ala Leu Lys
 1               5                  10                  15

Leu Ala

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gln Ile Lys Ile Trp Phe Pro Asn Arg Arg Met Lys Trp Lys Lys
 1               5                  10                  15

Pro Gly Tyr Ala Gly Ala Val Val Asn Asp Leu
            20                  25

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gln Ile Lys Ile Trp Phe Pro Asn Arg Arg Met Lys Trp Lys Lys
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gln Ile Lys Ile Phe Phe Pro Asn Arg Arg Met Lys Phe Lys Lys
 1               5                  10                  15

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Arg Lys Lys Arg Arg Gln Arg Arg Arg Pro Gly Tyr Ala Gly
```

```
                1               5              10              15

Ala Val Val Asn Asp Leu
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Gly Arg Lys Lys Arg Arg Gln Arg Arg Pro Gly Asp Val Tyr
 1               5                  10                  15

Ala Asn Gly Leu Val Ala
            20

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Pro Lys Gly Asp Pro Lys Gly Val Thr Val Thr Val Thr Val Thr
 1               5                  10                  15

Val Thr Gly Lys Gly Asp Pro Lys Pro Asp
            20                  25

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: This region may be 3-10 residues, selected from
      one or more charged amino acid residues (e.g. Lys, Arg), or not
      present.
<220> FEATURE:
<221> NAME/KEY: MOD_RES
<222> LOCATION: (27)..(36)
<223> OTHER INFORMATION: This region may be 3-10 residues, selected from
      one or more charged amino acid residues (e.g. Lys, Arg), or not
      present.

<400> SEQUENCE: 14
```

```
Xaa Xaa Xaa Xaa Xaa Xaa Xaa Xaa Xaa Xaa Ala Ala Val Ala Leu Leu
 1               5                  10                  15

Pro Ala Val Leu Leu Ala Leu Leu Ala Pro Xaa Xaa Xaa Xaa Xaa Xaa
                20                  25                  30

Xaa Xaa Xaa Xaa
        35

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: This region may be 3-10 residues, selected from
      one or more charged amino acid residues (e.g. Lys, Arg), or not
      present.
<220> FEATURE:
<221> NAME/KEY: MOD_RES
<222> LOCATION: (20)..(29)
<223> OTHER INFORMATION: This region may be 3-10 residues, selected from
      one or more charged amino acid residues (e.g. Lys, Arg), or not
      present.

<400> SEQUENCE: 15

Xaa Xaa Xaa Xaa Xaa Xaa Xaa Xaa Xaa Xaa Pro Ala Val Leu Leu Ala
 1               5                  10                  15

Leu Leu Ala Xaa Xaa Xaa Xaa Xaa Xaa Xaa Xaa Xaa Xaa
                20                  25

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Lys Lys
 1

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Lys Lys Leu Ala Ala Leu Pro Leu Val Leu Ala Ala Pro Leu
 1               5                  10                  15

Ala Val Leu Ala
                20

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Arg Arg Lys Lys Ala Ala Val Ala Leu Leu Pro
1               5                   10
```

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Arg Arg Lys Lys Ala Val Ala Val Ala Val Pro Ala Val Leu Leu Ala
1               5                   10                  15

Leu Leu Ala Pro
            20
```

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Arg Arg Lys Lys Pro Ala Val Leu Leu Ala
1               5                   10
```

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Arg Arg Lys Lys Pro Ala Val Leu Leu Ala Leu Leu Ala Leu Leu Ala
1               5                   10                  15
```

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Arg Arg Lys Lys Ala Leu Leu Pro Ala Val Leu Leu Ala Leu Leu Ala
1               5                   10                  15

Pro
```

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Arg Arg Lys Lys Pro Ala Val Leu Leu Ala Leu Leu Ala Pro
1               5                   10
```

```
<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Lys Lys Leu Leu Ala Leu Leu Ala Pro
 1               5                  10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Lys Lys Leu Leu Ala Pro
 1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Lys Lys Ala Ala Val Ala Leu Leu Pro Ala Val Leu Leu Ala
 1               5                  10                  15

Leu

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Lys Lys Ala Ala Val Ala Val Val Pro Ala Val Leu
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Lys Lys Ala Ala Val Ala Val Val Pro
 1               5                  10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 29

Arg Arg Lys Lys Ala Ala Val Ala
 1               5

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Arg Lys Lys Arg Arg Gln Arg Arg Pro Leu Ala Ala Leu Pro
 1               5                  10                  15

Leu Val Leu Ala Ala Pro Leu Ala Val Leu Ala
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Gly Arg Lys Lys Arg Arg Gln Arg Arg Pro Leu Ala Ala Leu
 1               5                  10                  15

Pro Leu Val Leu Ala Ala Pro Leu Ala Val Leu Ala
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Ala Ala Leu Pro Leu Val Leu Ala Ala Pro Leu Ala Val Leu Ala
 1               5                  10                  15

Pro Gly Arg Lys Lys Arg Arg Gln Arg Arg Cys
            20                  25

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Val Leu Ala Ala Pro Leu Ala Val Leu Ala Pro Gly Arg Lys Lys
 1               5                  10                  15

Arg Arg Gln Arg Arg Arg Cys
            20

<210> SEQ ID NO 34
<211> LENGTH: 17
<212> TYPE: PRT
```

<210> SEQ ID NO 34
<211> LENGTH: (not shown)
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Leu Ala Val Leu Ala Pro Gly Arg Lys Lys Arg Arg Gln Arg Arg Arg
 1               5                  10                  15
Cys

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gly Arg Lys Lys Arg Arg Gln Arg Arg Arg Cys
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Arg Lys Lys Arg Arg Gln Arg Arg Arg
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Arg Lys Lys Arg Arg Gln Arg Arg Arg
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Arg Lys Lys Arg Arg Gln Arg Arg Arg Cys
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Gly Arg Lys Lys Arg Arg Gln Arg Arg Arg Cys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Norleucine

<400> SEQUENCE: 40

Gly Arg Xaa Xaa Arg Arg Gln Arg Arg Arg Cys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Norleucine

<400> SEQUENCE: 41

Gly Arg Lys Lys Arg Arg Gln Xaa Xaa Arg Cys
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Norleucine

<400> SEQUENCE: 42

Gly Arg Lys Lys Arg Arg Gln Xaa Xaa Arg Cys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Gly Tyr Ala Gly Ala Val Val Asn Asp Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 44

Pro Gly Asp Val Tyr Ala Asn Gly Leu Val Ala
1               5                   10
```

METHOD OF INHIBITING INFLUENZA INFECTION WITH ANTIVIRAL PEPTIDES

CROSS REFERENCES TO RELATED APPLICATIONS

This application claims priority to U.S. provisional application No. 60/526,252, filed Dec. 1, 2003, the entire contents of which are incorporated by reference herein.

GOVERNMENT RIGHTS

This invention was made with United States government support awarded by the following agencies: NIH AI52049. The United States has certain rights in this invention.

FIELD OF THE INVENTION

This invention relates to compositions for inducing cellular resistance to infection. More specifically, the invention relates to peptides exhibiting activity against a broad spectrum of viruses, to pharmaceutical compositions comprising the peptides, and to methods of using the peptides to prevent and/or treat viral infections, and specifically respiratory infections.

BACKGROUND OF THE INVENTION

In recent years, various groups of peptide derivatives having activity against viruses have been disclosed. Examples of these peptides are disclosed in U.S. Pat. No. 5,700,780, issued to Beaulieu et al.; U.S. Pat. No. 5,104,854, issued to Schlesinger et al.; U.S. Pat. No. 4,814,432 issued to Freidinger et al.; Dutia et al., Nature 321:439 (1986); and Cohen et al., Nature 321:441 (1986). However, many of the known antiviral peptides known in the art are hydrophobic, and therefore, not very bioavailable. Moreover, many of these known antiviral peptides show activity against only a few types of viruses, due to their particular mechanisms of action. Additionally, many of these synthetic peptides are not effective in preventing initial viral infection, particularly against some of the virus types that most affect individuals.

Influenza virus causes millions of infection each year worldwide and is responsible for up to 20,000 deaths per year in the United States. Human Parainfluenza virus types 1,2,3 and Respiratory syncytial virus types A and B are the major viral pathogens responsible for causing severe respiratory tract infections in infants and young children. It is estimated that, in the United States alone, approximately 1.6 million infants under one year of age will have a clinically significant RSV infection each year and an additional 1.4 million infants will be infected with PIV-3. Approximately 4000 infants less than one year of age in the United States die each year from complications arising from severe respiratory tract disease caused by infection with RSV and PIV-3.

Currently, no product exists which can effectively prevent infections from many respiratory viruses such as Respiratory Syncitial Virus and Human Parainfluenza virus. There remains a need for a treatment which is effective at preventing a wide range of cellular infections. There also remains a need for an antiviral peptide that can be easily and effectively administered to prevent infection from common respiratory viruses.

SUMMARY

Described herein are antiviral peptides and methods of treating viruses using the peptides. The peptides exhibit broad spectrum anti-viral activity and low toxicity. One embodiment provides a method of treating or preventing a viral respiratory infection in a mammal that includes administering an effective amount of an antiviral peptide to a mammal having, suspected of having, or at risk for a viral respiratory infection, wherein the antiviral peptide is selected from the group consisting of SEQ ID NOS: 1-15, SEQ ID NOS 18-42, fragments thereof, derivatives thereof, and combinations thereof, wherein when the antiviral peptide is SEQ ID NO:14, SEQ ID NO:15 (see paragraph [0057]), a fragment or derivative thereof, then X1 and X2 are selected from one or more charged amino acid residues such that each X1 and each X2 may be the same or different charged amino acid residue, further wherein n has a value of 0 or 3-10, and m has a value of 0 or 3-10. In some of these embodiments, either m=0 or n=0. In still other embodiments if m=0, n can have a value from 4 to 10, and if n=0, m can have a value from 4 to 10. In the above methods, the peptide is administered with a pharmaceutically acceptable carrier and/or the peptide can further include a solubility tag. In certain embodiments, the antiviral peptide is administered to the respiratory system, such as via inhalation or intranasally. The antiviral peptide can be administered prophylactically, after the mammal has been exposed to a virus that is capable of causing the viral respiratory infection and/or at about the time the mammal is exposed to a virus that is capable of causing the viral respiratory infection. Viral infections that can be treated or prevented include viral respiratory infection caused by a coronavirus, a rhinovirus, respiratory syncytial virus, a paramyxovirus, a parainfluenza influenza or an influenza virus. In some embodiments, the viral respiratory infection is not caused by an adenovirus. In the described methods, the peptides can be re-administered one or more times to the mammal, and such re-administrations can occur within about two to four hours of the previous administration and/or after there is substantially no free antiviral peptide present in the respiratory system. In certain embodiments, the antiviral peptide backbone consists of d-amino acids. Although these treatments can be used on any mammal, in some instances they are used on humans.

Also described is a method of inducing resistance to viral infection in a mammalian cell that includes:

(a) contacting one or more mammalian cells with an effective amount of at least one peptide selected from the group consisting of SEQ ID NOS: 1-15, SEQ ID NOS: 18-42, fragments thereof, derivatives thereof, and combinations thereof to the mammal, wherein when the antiviral peptide is SEQ ID NO:14, SEQ ID NO:15, a fragment or derivative thereof, then X1 and X2 are selected from one or more charged amino acid residues such that each X1 and each X2 may be the same or different charged amino acid residue, further wherein n has a value of 0 or 3-10, and m has a value of 0 or 3-10; and (b) removing free peptide from the presence of the mammalian cells, wherein at least a portion of the mammalian cells are resistant to viral infection after (b). This method can also include (c) contacting one or more infectious viruses with one or more of the mammalian cells; and/or (d) measuring the viral infection of the mammalian cells resulting from (c).

In these embodiments (b) can be performed by washing away the free peptide or can occur naturally such as through a biological process. These methods can be performed on mammalian cells that are in vitro or in vivo.

Additionally described is a method of inducing resistance to viral infection in a mammalian cell that includes:

(a) contacting one or more infectious viruses with an effective amount of at least one antiviral peptide in the absence of a mammalian cell thereby rendering the one or more infectious viruses less infectious, wherein the at least one antiviral peptide is selected from the group consisting of SEQ ID NOS: 1-15, SEQ ID NOS: 18-42, fragments thereof, derivatives thereof, and combinations thereof to the mammal, wherein when the antiviral peptide is SEQ ID NO:14, SEQ ID NO:15, a fragment or derivative thereof, then X1 and X2 are selected from one or more charged amino acid residues such that each X1 and each X2 may be the same or different charged amino acid residue, further wherein n has a value of 0 or 3-10, and m has a value of 0 or 3-10.

This method can further include contacting the one or more infectious viruses with one or more mammalian cells after (a). These and other methods can be performed on mammalian cells in vitro or in vivo.

Further described are antiviral peptides selected from the group consisting of SEQ ID NOS:30-42 as well as pharmaceutical compositions that contain these peptides. These peptides and compositions can be used to treat or prevent viral infections in mammals. Such methods can include those described above. These peptides and compositions can be used to treat a variety of viruses or infections, including those caused by enveloped viruses, non-enveloped viruses, human immunodeficiency virus, herpes simplex viruses, cytomegalovirus, or combinations thereof.

BRIEF DESCRIPTION OF THE DRAWINGS

I. Anti-Viral Activity of Peptides

FIGS. 1A, B, D and E are graphical representations showing the dose-dependent inhibition of HSV-1 by antiviral peptides of the present invention (SEQ ID NO:1), (SEQ ID NO:3) and (SEQ ID NO:4) compared to control peptides (SEQ ID NO:16 and SEQ ID NO:17). FIG. 1C shows the cytotoxic effects of SEQ ID NO:1 and SEQ ID NO:17. FIGS. 1A-D: ● EB; ○, EBX; ▲, RRKK. FIG. 1E: ●, EB; ○, LALA.

FIG. 2 is a graphical representation showing viral inhibition by a biotinylated antiviral peptide (SEQ ID NO:2) and the non-biotinylated analog of the present invention. Symbols: ●, bEB; ○, EB.

FIG. 3 is a graphical representation showing the dose-dependent inhibition of HSV-1 infection by an antiviral peptide of the present invention (SEQ ID NO:1) as compared to acylovir. Symbols: ●, EB; Δ, Acyclovir.

FIGS. 4A and 4B are graphs illustrating that an antiviral peptide of the present invention (SEQ ID NO:1) inhibits virus spreading. Panel A: ●, EB 1 hr post-infection; ○, EB pre- and post-infection; Δ size of plaques. Panel B: black bars, untreated virus, gray bars, EB treatment.

FIG. 5 is a graph illustrating that the antiviral activity of an antiviral peptide of the present invention (SEQ ID NO:1) is dependent on virus input. Virus per well: ○, 19 plaque forming units (pfu); ●, 210 pfu; Δ, 5,700 pfu.

FIGS. 6A and 6B are graphs illustrating the blocking of viral entry into cells by an antiviral peptide of the present invention (SEQ ID NO:1). See Example 7 for details. Panel A, 25 μM antiviral peptide: ●, EB; ▲, EBX; ○, mock. Panel B: ●, EB; ▲, EBX50 nM.

FIGS. 7A and 7B are graphs illustrating that the peptide does not inhibit steps post-entry and the dose response of an antiviral peptide of the present invention (SEQ ID NO:1). Panel A: ●, virus with 50 nM EB; ○, β-galactosidase expression; Panel B, ●, 50 nM, EB; ○, EBX.

FIGS. 8A and 8B are graphs illustrating the virucidal activity of an antiviral peptide of the present invention (SEQ ID NO:1). See Example 7 for details. Panel A: ●, EB; ○; EBX; Panel B: ●, EB; Δ, dialysed virions previously exposed to EB; ▲, virions exposed to EB and trapped with 0.22 nm filters.

FIGS. 9A and 9B are graphs illustrating the in vivo prophylactic activity against HSV-1 of an antiviral peptide of the present invention (SEQ ID NO:1).

FIGS. 10A and 10B are graphs illustrating the HIV p24 reduction caused by KLA and TAT-Cd, respectively.

FIGS. 11A, B, C, and D show that the present peptides block influenza virus A infection in cultured cells and compares the cytoxic effects of these peptides. Panel A: bKLA; Panel B: EB; Panel C: bHOM-9; Panel D: bTAT-9. Symbols: ●, antiviral; ○, cytotoxicity.

FIGS. 12A, B, C, and D compare measurements of cytopathic effects and hemagglutination for scoring antiviral effects of some of the present peptides against influenza A virus. Panels A and B: ○, no peptide; ●, 25 μM EB; Δ, 6 μM bKLA. Panels C and D: ○, no peptide; Δ6 μM bHOMd.

FIG. 13 shows that pre-treatment of influenza virus prior to infection results in protection in vivo.

FIG. 14 also shows protection from influenza virus in vivo when peptide is delivered post-infection.

II. Structural Changes Modify Antiviral Effects of Peptides

FIGS. 15A, B, C, and D show inhibition of entry and inactivation of pre-adsorbed virus by TAT peptides. Panel A, TAT-C; Panel B, bTAT-9X; Panel C, $n_{50,51}$ TAT-C, 31° C.; Panel D, $n_{50,51}$ TAT-C, 37° C.

FIGS. 16A and B show the temperature-dependence of the inhibitory effects of TAT peptides. Symbols: ▲, TAT-C; □, $n_{50,51}$ TAT-C; ■, $n_{50,51}$ TAT-C.

FIG. 17 depicts reversibility of the inhibitory effects of certain TAT peptides.

FIG. 18 illustrates inhibition of entry (●)and virus inactivation (○) by $TAT^{O}$.

FIGS. 19A, B, C, and D show the inhibition and release of pre-adsorbed infectious virus by heparin and TAT-Cd.

FIGS. 20A and B demonstrate inactivation of virions by the TAT-C peptide.

FIG. 21 shows the correlation between inactivation of pre-adsorbed virus and inactivation of virions in solution.

FIG. 22 demonstrates that inactivation of virions by TAT-Cd is not reversible over time or by high salt treatment FIG. 23A and B depict the effect of trypsin on (A) peptide-treated virions and on (B) peptides in solution.

III. Peptide Treatment Induces Cellular Resistance to Viral Infection

FIGS. 24A, B, C, and D show that cell pretreatments with TAT-Cd (SEQ ID NO:39) or EB (SEQ ID NO:1) inhibit viral infection even after washing the cells.

FIG. 25 demonstrates the rapidity of induction of cellular resistance to viral infection using the present peptides. The upper panel shows results with TAT-C and TAT-Cd peptides. The lower panel shows results with EBX and EB peptides.

FIG. 26 is a graph illustrating induction of cellular resistance to viral infection by variations of the present peptides.

FIG. 31A, B, and C show the temperature dependence, or lack thereof, for induction of cellular resistance to viral infection and of free and adsorbed virions.

Figure 32:
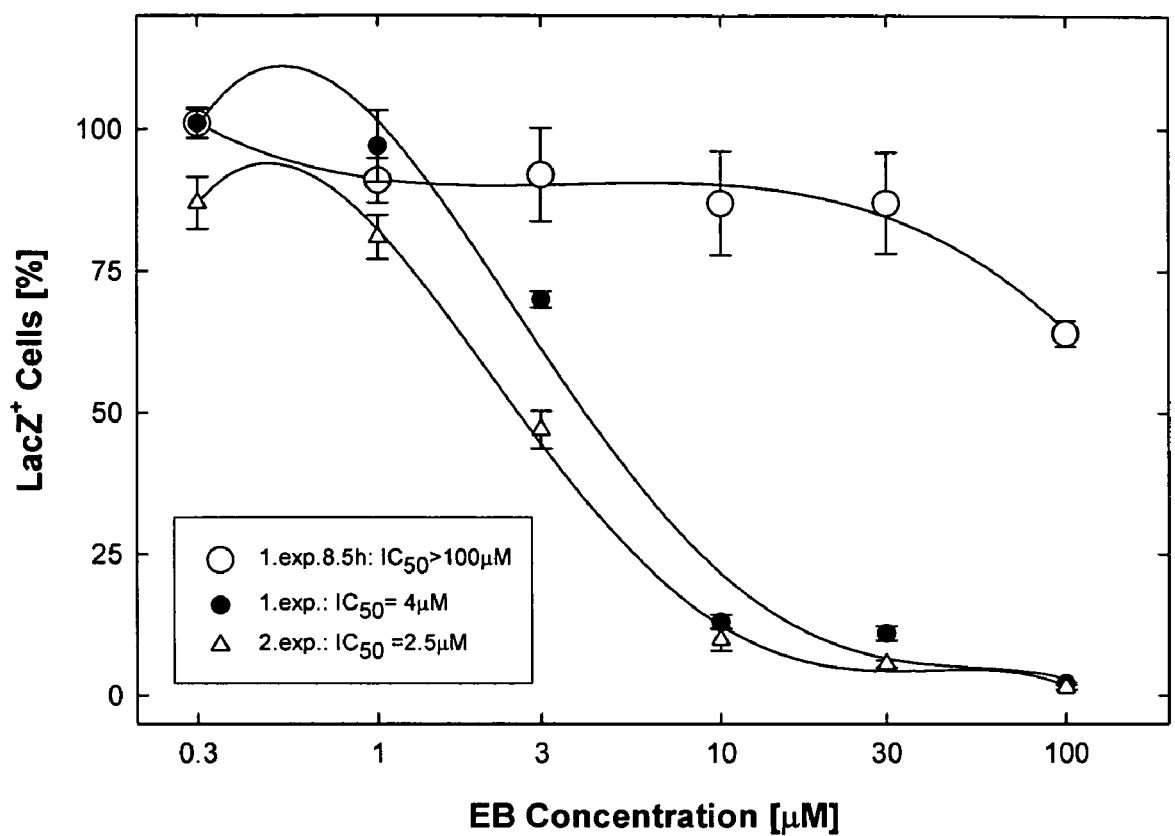
Figure 33A:
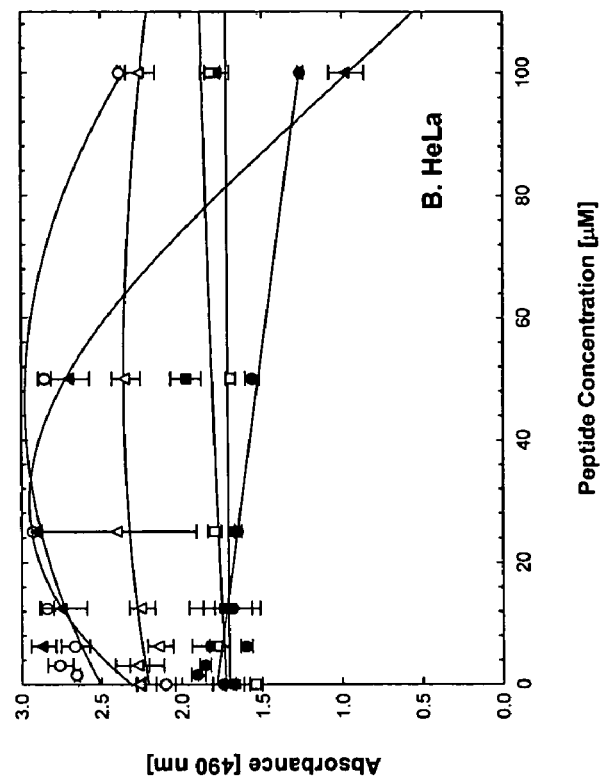
Figure 33B:
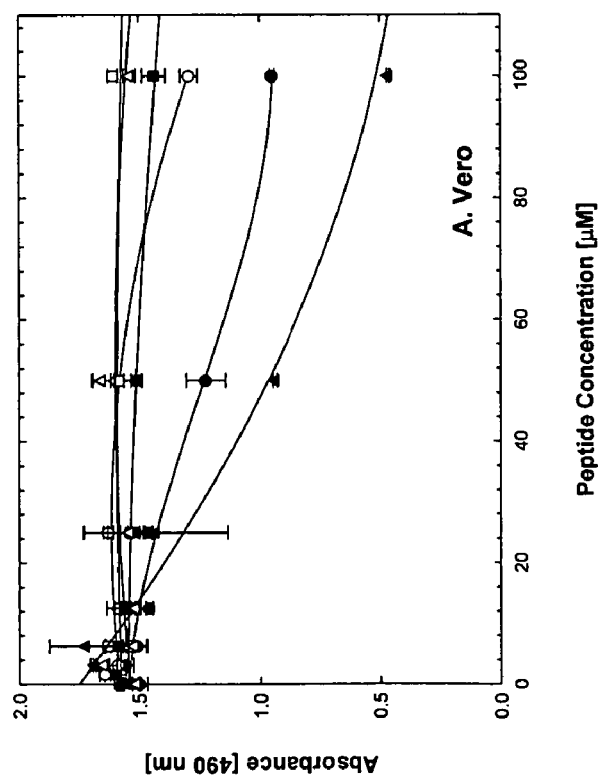
Figure 33C:
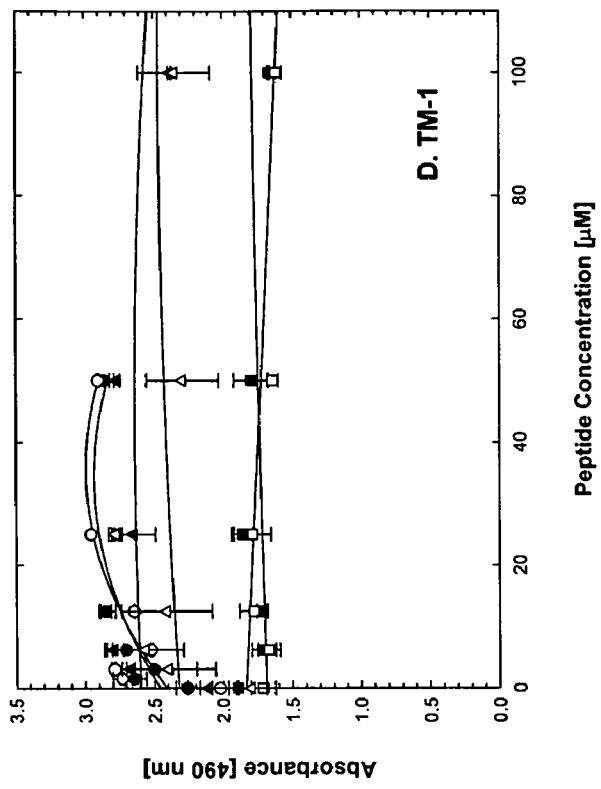
Figure 33D:
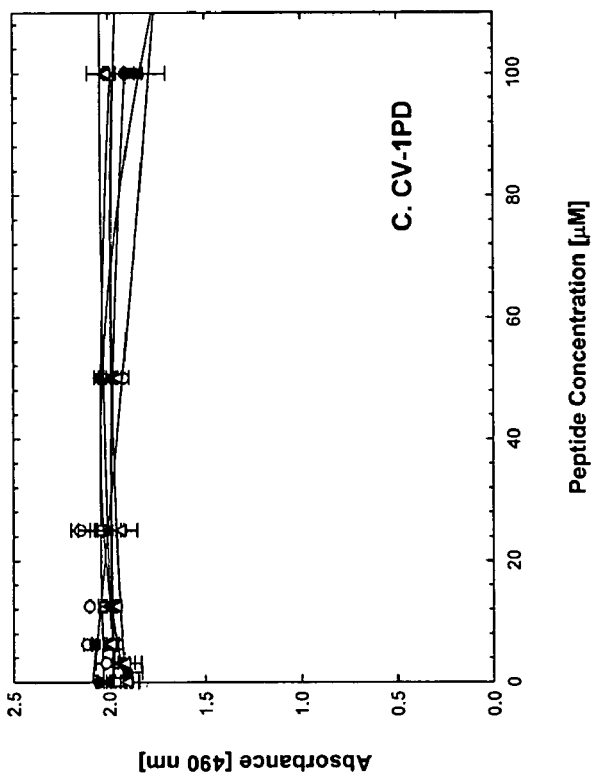
Figure 33E:
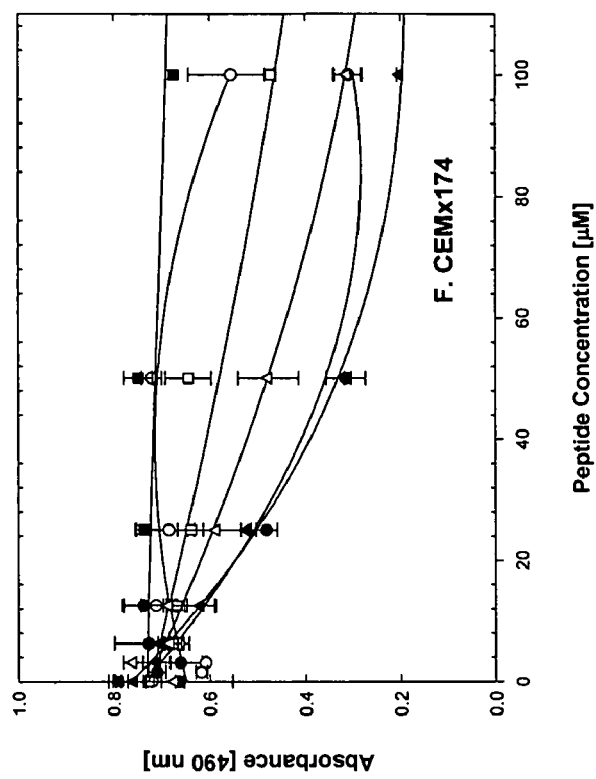
Figure 33F:
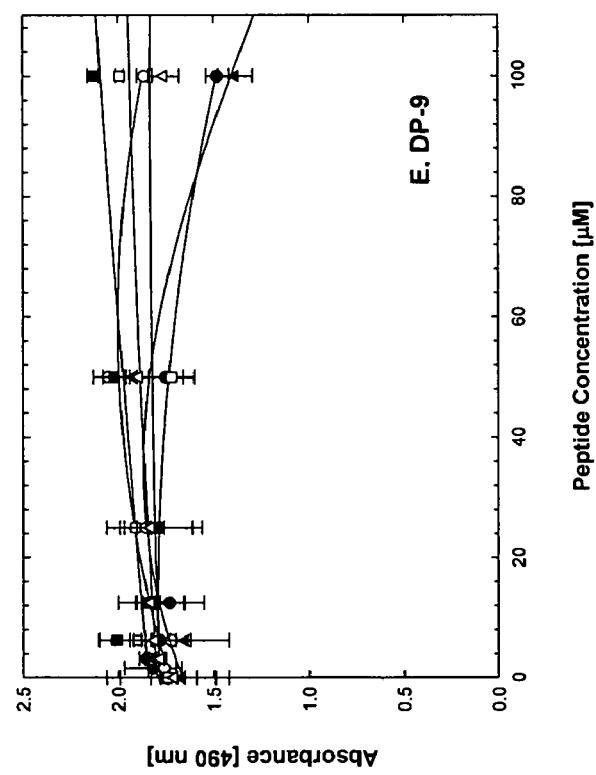
Figure 33G:
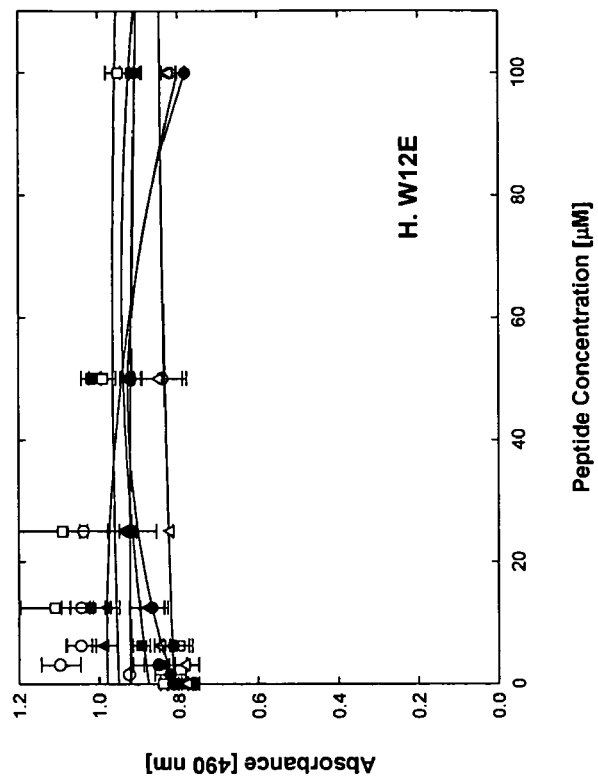
Figure 33H:
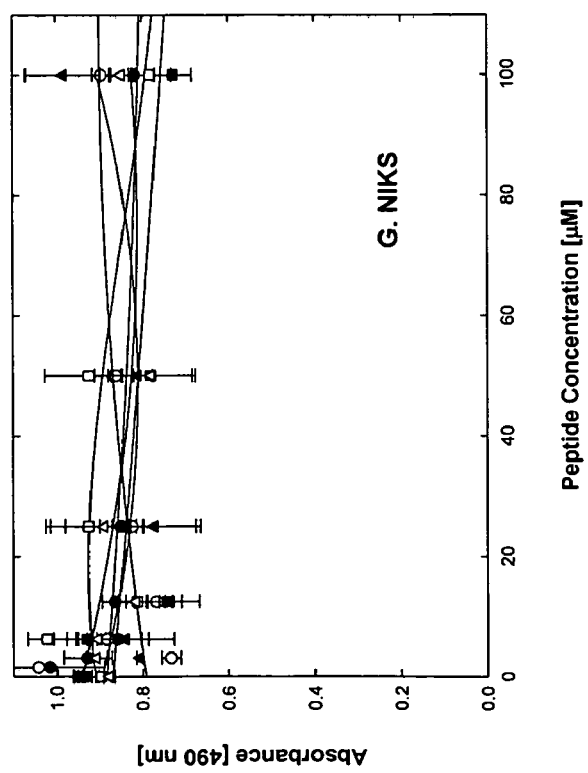

FIG. 32 shows that cellular resistance can be repeatedly induced in cells.

IV. Evaluation of Peptide Toxicity

FIGS. 33A-H show the toxicity of peptides tested against 8 different cell lines using the MTS assay, including (A) Vero; (B) HeLa; (C) CV-IPD; (D) TM-1; (E) DP-9; (F) CEMx174; (G) NIKS; (H) WIZE.

FIGS. 34A, B, C, and D show the lack of toxicity to mouse cornea following application of peptides four times per day for seven days.

FIGS. 35A-E show low magnification views of peptide toxicity in mouse vagina following two administrations in a 24 hour period.

Figure 35:
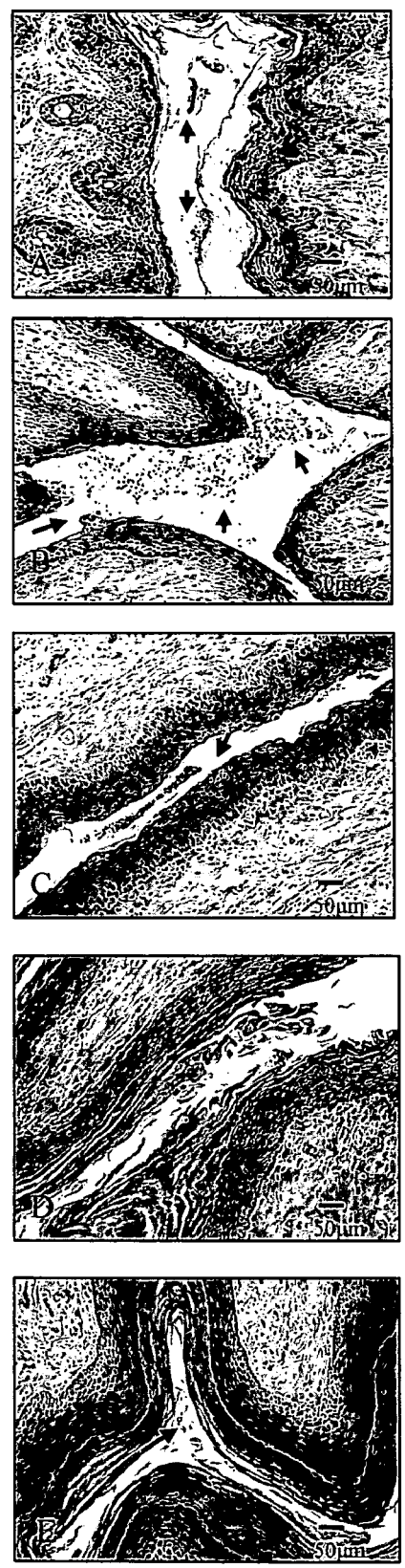

FIGS. 36A-E show high magnification views of the tissues from FIG. 35 showing a lack of peptide toxicity in a mouse vagina.

DETAILED DESCRIPTION OF THE INVENTION

In the description that follows, a number of terms are utilized extensively. Definitions are herein provided to facilitate understanding the invention.

Antiviral peptide: The antiviral peptide comprises at least in part a membrane transiting peptide, or a fragment or a derivative thereof, that is a pharmacologically effective antiviral agent when administered in an effective amount.

Membrane transiting peptide (membrane transiting motif): A peptide having a sequence of amino acids that renders the peptide capable of traversing lipid bilayer membranes to enter cells or subcellular compartments.

Pharmaceutically acceptable carrier: An acceptable vehicle for administering antiviral peptides to mammals comprising one or more non-toxic excipients which do not react with or reduce the effectiveness of the pharmacologically active antiviral peptide contained therein.

Solubility tag: A short peptide sequence comprised of charged amino acids which, when attached to a terminal residue of a longer insoluble peptide sequence, will improve solubility in an aqueous medium. In some embodiments the charged amino acids of the solubility tags are exclusively positively charged amino acids, including, but not limited to, ornithine, lysine, and arginine. Solubility tags may be 2 to 24 amino acids long or longer, and typically can be 4, 5, 6, 7, 8, 9, 10, 11, 12, 13, 14, 15, or 16 amino acids long. A solubility tag may be attached to either terminus or both termini of the longer insoluble peptide.

In this application, the standard one letter abbreviated names for the amino acids are used throughout. See Lehninger et al. "Principles of Biochemistry", Worth Publishers (New York, N.Y.) p. 113 (1983). All amino acid sequences in this application are depicted using standard nomenclature, with the left most amino acid residue at the end of each sequence being the amino-terminal residue and the residue at the right end of each sequence being the carboxyl-terminal residue. The amino acids of the peptides described herein may be either levo amino acids or dextro amino acids, as denoted "l" or "d" in the peptide designation (Table 1). Any of the peptides described herein can have peptide backbones made up of d amino acids. Surprisingly, it has been discovered that peptides made up of d-amino acids can be as effective as peptides having the same sequence that are made up of l-amino acids.

Some embodiments of the present invention relate to novel antiviral peptides which are based on membrane transiting peptides. Various membrane transiting peptides are well known in the art. It has been surprisingly and unexpectedly discovered that membrane transiting peptides exhibit a broad spectrum of antiviral activity, including such activity activity when applied topically or administered in vivo. Exemplary antiviral peptides of the present invention derived from membrane transiting peptides are described below Table 1, although any membrane transiting peptide known in the art may be used, see, e.g., Pooga et al., *FASEB J.,* 12:67 (1998) and Oehlke et al., *FEBS Lett.,* 415:196 (1997).

TABLE 1

Peptides

| Peptide | SEQUENCE ID NUMBER | Sequence |
|---|---|---|
| EB | SEQ ID NO:1 | $NH_2$ - RRKKAAVALLPAVLLALLAP-COOH |
| bEB | SEQ ID NO:2 | b - RRKKAAVALLPAVLLALLAP-COOH |
| EBPP | SEQ ID NO:3 | $NH_2$ - RRKKAAVALLAVLLALLAPP-COOH |
| LALA | SEQ ID NO:4 | $NH_2$ - RRKKPAVLLALLA-COOH |
| bKLA | SEQ ID NO:5 | b - KLALKLALKALKAALKLA-amide |
| bKLAd$_{11/12}$* | SEQ ID NO:6 | b - KLALKLALKA<u>L</u>KAALKLA-amide |
| bHOM-9 | SEQ ID NO:7 | b - <u>RQIKIWFPNRRMKWKK</u>-9 |
| bHOMd | SEQ ID NO:8 | b - <u>RQIKIWFPNRRMKWKK</u>-amide |
| bHOMFF | SEQ ID NO:9 | b - RQIKI F FPNRRMK F KK-amide |

TABLE 1-continued

Peptides

| Peptide | SEQUENCE ID NUMBER | Sequence |
|---|---|---|
| bTAT-9 | SEQ ID NO:10 | b - YGRKKRRQRRR-9 |
| bTAT-9x | SEQ ID NO:11 | b - YGRKKRRQRRR-9x |
| TAT-17 | SEQ ID NO:30 | NH$_2$-GRKKRRQRRRPLAALPLVLAAPLAVLA-COOH |
| bTAT-17 | SEQ ID NO:31 | b-YGRKKRRQRRRPLAALPLVLAAPLAVLA-COOH |
| b17TAT-C | SEQ ID NO:32 | b-LAALPLVLAAPLAVLAPGRKKRRQRRRC-amide |
| b12TAT-C | SEQ ID NO:33 | b-LVLAAPLAVLAPGRKKRRQRRRC-amide |
| b6TAT-C | SEQ ID NO:34 | b-LAVLAPGRKKRRQRRRC-amide |
| bTAT-C | SEQ ID NO:35 | b-GRKKRRQRRRC-amide |
| TAT⁻ | SEQ ID NO:36 | NH$_2$-GRKKRRQRRR-COOH |
| TAT° | SEQ ID NO:37 | NH$_2$-GRKKRRQRRR-amide |
| TAT-C | SEQ ID NO:38 | NH$_2$-GRKKRRQRRRC-COOH |
| TAT-Cd | SEQ ID NO:39 | NH$_2$-<u>GRKKRRQRRRC</u>-COOH |
| n$_{50,51}$TAT-C | SEQ ID NO:40 | NH$_2$-GRnLnLRRQRRRC-COOH |
| n$_{55,56}$TAT-C | SEQ ID NO:41 | NH$_2$-GRKKRRQnLnLRC-amide |
| n$_{55,56}$TAT-Cd | SEQ ID NO:42 | NH$_2$-GRKKRRQnLnLRC-amide |
| N$^{E13}$-biotinyl transportan | SEQ ID NO:12 | GWTLNSAGYLLGKINLKALAALAKKIL<br>                                          \|<br>                                          b |
| VT5 | SEQ ID NO:13 | fluor-DPKGDPKGVTVTVTVTVTGKGDPKPD |

Residues indicated in bold are positively charged residues
b = biotin-aminohexanoyl
d = peptide composed of all D amino acid residues
fluor = fluorescent label
-9 = PGYAGAVVNDL-COOH (SEQ ID NO:43)
-9x = PGDVYANGLVA-COOH (SEQ ID NO:44)
nL = norleucine (2-aminohexanoic acid)
*d residues are underlined The antiviral peptides of the present invention may be used alone in an effective amount. Although most membrane transiting peptides are soluble, some are not, although insoluble membrane transiting motifs may be utilized in antiviral peptides by the following method. If the antiviral peptide is insoluble in an aqueous pharmaceutically acceptable carrier, a solubility tag may be added to the antiviral peptide.

As shown in Table 1, SEQ ID NOS: 1-4 have had a solubility tag covalently attached. The present invention relates to such novel antiviral peptides which in part comprise a solubility tag covalently attached and have the following sequence:

(X1)$_n$-A-A-V-A-L-L-P-A-V-L-L-A-L-L-A-P—(X2)$_m$ (SEQ ID NO: 14) or (X1)$_n$—P-A-V-L-L-A-L-L-A-(X2)$_m$ (SEQ ID NO:15) wherein X1 and X2 are selected from one or more charged amino acid residues (e.g. K, R) where each X1 and each X2 may be the same or different charged amino acid residue; and wherein n has a value of 0 or 3-10, and m has a value of 0 or 3-10, wherein in one embodiment either m=0 or n=0. One example of a solubility tag is R-R-K-K (SEQ ID NO:16). In the preferred embodiment, all charged amino acid residues of the solubility tag are positively charged amino acid residues. The inventors have surprising and unexpectedly discovered that insoluble membrane transiting peptides, when coupled to a solubility tag, create antiviral peptides that exhibit strong antiviral activity against a broad spectrum of viruses.

Many membrane transiting peptides may function as antiviral peptides of the present invention without the need for solubility tags. See Table 1. Moreover, although solubility tags may improve the solubility of some membrane transiting peptides, these particular membrane transiting peptides may be suitable as antiviral peptides without incorporating solubility tags.

The antiviral peptides of the present invention may have various reactive tags attached to their terminal amino acid residues. Such tags may be useful in detection/removal of the synthetic peptides of the present invention. Such tags may include, by way of example only, biotin, as well as any other tags well-known in the art. SEQ ID NOS: 2, 5-12 and Example 2 demonstrate the inclusion of such reactive tags.

Derivatives of membrane transiting peptides of the present invention have also been found to be useful as antiviral peptides. Derivatives of inventive antiviral peptides are peptides that include a membrane transiting motif wherein one or more of the amino acid residues of the membrane transiting motif are deleted to yield fragments or are substituted for other amino acid residues. Substitutions may be conservative or may be sequence rearrangements. Conservative substitutions are well known to those of skill in the art; amino acids of similar or identical charge, size or hydrophobicity may be substituted for each other. For example, lysine and arginine are conservative substitutions for each other, as are aspartic and glutamic acids, phenylalanine, tyrosine, and tryptophan, and so forth. Rearranged sequences are those in which one or more amino acids are moved from their original position to a new position within the sequence of the inventive peptide. For example, SEQ ID NO:3 (see Table 1) is a derivative of SEQ ID NO:1. SEQ ID NO:3 differs from SEQ ID NO:1 only in that both proline amino acid residues have been placed at the carboxy terminus of the peptide. Antiviral peptide fragments of the invention can have deletions of 1, 2, 3, 4, 5, 6, 7, 8, 9, 10, 11, 12 or more amino acids, and substituted derivatives can have 1, 2, 3, 4, 5, 6, 7, 8, 9, 10 or more substitutions. In some embodiments, derivatives of inventive antiviral peptides have both deletions and substitutions.

Substituted or fragment membrane transiting motifs must retain antiviral activity to remain within the scope of the invention. The antiviral peptides according to the present invention comprising a substituted membrane transiting motif or derivative thereof can be tested for antiviral activity via the methodology described in the following Examples. Example 2 demonstrates that antiviral peptides comprising substituted membrane transiting motifs retain antiviral activity, as shown by SEQ ID NO:3, a derivative of SEQ ID NO:1 as described above. Table 2 lists potential active fragments and other derivatives of an antiviral peptide according to the present invention. Such derivatives and fragments are within the scope of the present invention.

ing Examples. Any method for peptide synthesis well known in the art may be used, for example, Schroeder and Lubke, in "The Peptides", Vol. 1, Academic Press, New York, N.Y., pp. 2-128 (1965); "The Peptides: Analysis, Synthesis, Biology", (E. Gross et al., Eds.), Academic Press, New York, N.Y., Vol. 1-8, (1979-1987); Stewart and Young, in "Solid Phase Peptide Synthesis", 2nd Ed., Pierce Chem. Co., Rockford, Ill. (1984); Wild et al., *Proc. Natl. Acad. Sci. USA,* 89: 10537 (1992); and Rimsky et al., *J Virol,* 72: 986 (1998); Chan & White in "Fmoc Solid Phase Peptide Synthesis: A Practical Approach", Oxford University Press, (2000).

As demonstrated in the following Examples, the antiviral peptides of the present invention show antiviral activity against a wide range of enveloped and non-enveloped viruses. Examples of enveloped viruses include, but are not limited to, human immunodeficiency virus (HIV), vesicular stomatitis virus (VSV), herpes simplex viruses (HSV-1 and HSV-2), and other herpes viruses, for example, varicella-zoster virus (VZV), EBV, equine herpes virus (EHV), influenza virus and human cytomegalovirus (HCMV). Examples of non-enveloped viruses include, but are not limited to, papilloma virus (PV) and adenoviruses (AV).

The present peptides have also been found to effective against respiratory viruses, including influenza A. The present peptides are expected to have activity against a wide range of respiratory viruses including those that cause upper respiratory tract infections and lower respiratory tract infections. Specific examples of viruses that may be treated by the present peptides include coronaviruses, rhinoviruses, Respiratory Syncytial Virus, paramyxoviruses, such as parainfluenza viruses, for example HPIV-1, HPIV-2, HPIV-3, HPIV-4, HPIV-4a and HPIV-4b, and other influenza viruses, such as influenza B. In some of the present embodiments, the respiratory virus treated by the disclosed methods is not an aden-

TABLE 2

Potential Active Fragments and Other Derivatives of Antiviral Peptides

| Peptide | Sequence | Purpose |
| --- | --- | --- |
| P11 (SEQ ID NO:18) | RRKKAAVALLP | activity of n-terminal half |
| P12 (SEQ ID NO:19) | RRKKAVAVAVPAVLLALLAP | spacing of LLA motif |
| Peptides testing role of LLA motif | | |
| P13 (SEQ ID NO:20) | RRKKPAVLLA | One LLA |
| P14 (SEQ ID NO:4) | RRKKPAVLLALLA | Two LLAs |
| P15 (SEQ ID NO:21) | RRKKPAVLLALLALLA | Three LLAs |
| Peptides for testing sequential removal of aa triplets | | |
| P16 (SEQ ID NO:22) | RRKKALLPAVLLALLAP | -3N-terminus |
| P17 (SEQ ID NO:23) | RRKKPAVLLALLAP | -6N-terminus |
| P18 (SEQ ID NO:24) | RRKKLLALLAP | -9N-teminus |
| P19 (SEQ ID NO:25) | RRKKLLAP | -12N-terminus |
| P20 (SEQ ID NO:26) | RRKKAAVALLPAVLLAL | -3C-terminus |
| P21 (SEQ ID NO:27) | RRKKAAVAVVPAVL | -6C-terminus |
| P22 (SEQ ID NO:28) | RRKKAAVAVVP | -9C-terminus |
| P23 (SEQ ID NO:29) | RRKKAAVA | -12C-terminus |

The peptides of the present invention can be prepared by processes which incorporate methods commonly used in peptide synthesis such as classical solution coupling of amino acid residues and/or peptide fragments, and, if desired, solid phase techniques. Such methods are described in the followovirus. Illnesses resulting from infections by these viruses, such as common colds, influenza, bronchiolitis, pneumonia, croup, bronchitis, pharyngitis, laryngitis, otitis media and sudden acute respiratory system (SARS), can also be treated according to some of the present methods.

A method for demonstrating the inhibitory effect of the antiviral peptides of the present invention on viral replication is the well-known cell culture technique as taught in the following Examples. Such methods are well known in the art. See Wild et al., *Proc. Natl. Acad. Sci. USA*, 89: 10537 (1992).

The therapeutic efficacy of the antiviral peptides as antiviral agents can be demonstrated in laboratory animals, for example, by using a murine model.

Additionally, the therapeutic effect of the pharmacologically active peptides of the present invention can be shown in humans via techniques well-known in the art. See, for example, Kilby et al., *Nature Medicine* 4: 1302 (1998).

As used herein, free peptide, free protein or the like, refers to peptide that is not bound to a cell, bound to a virus, or internalized within a cell. The cell that binds or internalizes the peptide can be the cell that is being treated for viral infection or the cell can be uninfected. In a similar manner, the virus the peptide binds to can be the cause of the infection being treated or prevented or can be unrelated. Typically, free antiviral peptide that is contacted with a cell or administered to a subject will eventually be removed by washing, degradation or other biological processes. As such, only the peptide that has bound to the cell or virus, or has been internalized by the cell, will be available for anti-viral activity and no free peptide will be present to provide additional anti-viral activity.

The present peptides have also been shown to have unexpected antiviral properties as demonstrated in the examples. Thus, it has been determined that no free external peptide is required to be present during viral infection in order to confer viral resistance to the treated cell. In fact, viral resistance afforded to cells by treatment with some peptides is on the order of several hours, up to six hours, or more. This is important because it is often difficult to provide a constant supply of available peptides to cells because administered peptides are removed by natural processes prior to viral infection. Thus, the interval between dosages of the peptides can be longer intervals than would be required if peptide was constantly required to be present in order to provide resistance.

Without limiting the scope of the invention, it is believed that the antiviral peptide, or breakdown product of the peptide, is in contact with the cell and confers viral resistance to the cell. In addition, it is believed that the peptide or breakdown product thereof may target carbohydrate chains on the surface of the cell (as well as the surface of the virus) rather than compete for binding of virus to the cell. As such, free peptide in solution may not be required to confer viral immunity as long as the cell has been contacted with peptide. It is also contemplated that after peptide exposure the peptide may trigger a cascade of cellular events that confers viral immunity to the cell and that this cascade of events may provide effective viral resistance.

Additionally, many of the present peptides have been shown to provide effective antiviral properties at low concentrations.

Several of the present peptides have also shown to rapidly induce cellular resistance to viral infection so that only a short peptide exposure is needed to induce resistance. As such, the present peptides can be administered prior to, simultaneous with, or shortly after, viral exposure and still provide effective protection against viruses. Because the peptides rapidly induce viral resistance and free peptide is not required to be present to prevent viral infection, even short-lived or readily removed peptides can be effective for treating or preventing viral infection.

The present peptides have also been found to induce viral resistance in a cell-type independent fashion. Accordingly, a large variety of cell types, such as fibroblasts, tissues, epithelial cells, endothelial cells, immune cells and infected cells could be treated with the present peptides. Some peptides (e.g. EB) that bind to, or are internalized by, cells are difficult to remove from the treated cell. The resistance afforded by such peptides is therefore not readily reversible.

Without limiting the scope of the present invention, experimental results suggest that the peptides can confer viral resistance to treated cells by different mechanisms. The present peptides effectively induce resistance directly in treated cells. Presumably, the peptides can bind to the cell surfaces at, e.g., the carbohydrates of glycosylated proteins, or receptors and prevent viral entry, and/or the peptides can be internalized by the cells thereby conferring viral resistance. The present peptides have also been shown to be able to directly act on virus and inactivate virus in the absence of cells, again possibly by targeting carbohydrates of glycosylated proteins. Because the peptides can directly reduce the infectivity of virus in the absence of cells, the peptides can be used to treat surfaces or objects that have been contaminated with virus or are suspected of being contaminated to help prevent spread of the viral infection.

An antiviral peptide of the present invention would be employed as an antiviral agent by administering the peptide topically to a warm-blooded animal, e.g., humans, horses, other mammals, etc. The peptide may be administered in a vehicle comprising one or more pharmaceutically acceptable carriers, the proportion of which is determined by the solubility and chemical nature of the peptide, chosen route of administration and standard biological administration. Suitable vehicles or carriers for the formulations of the peptide are described in the standard pharmaceutical texts. See "Remington's Pharmaceutical Sciences", 18$^{th}$ Ed., Mack Publishing Company, Easton, Pa. (1990). Because inventive peptides may target carbohydrates on the surfaces of the virus and/or the cell, to ensure efficacy, the vehicle (carrier) in such formulations should be free or substantially free (e.g., better than 90, 95, 98, or 99 wt %) of carbohydrates that bind to the peptides.

For topical administration, the antiviral peptide can be formulated in a pharmaceutically accepted vehicle containing an effective amount of the antiviral peptide, typically 0.01 or 0.1 to 10%, of the antiviral peptide. Such formulations can be in the form of a solution, cream or lotion. The antiviral peptides of the present invention may be used for treating viral infections of the skin or part of the oral cavity or genital or respiratory tract. The antiviral peptides can be used individually or in combination, to treat a wider variety of viruses. Such topical applications could be applied to barrier materials to protect the wearer, such as gloves, condoms and other barriers known in the art.

For systemic administration, the antiviral peptides of the present invention may be administered by either intravenous, subcutaneous, or intramuscular injection, alone or in compositions with pharmaceutically accepted vehicles or carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present invention can be obtained in the form of therapeutically acceptable salts that are well-known in the art.

Because the present peptides have shown activity against respiratory viruses, the present peptides can be delivered locally to the respiratory system, for example to the nose, sinus cavities, sinus membranes or lungs. The present peptide(s), or pharmaceutical compositions containing one or more peptides, can be delivered to the respiratory system in any suitable manner, such as by inhalation via the mouth or intranasally. The present compositions can be dispensed as a powdered or liquid nasal spray, suspension, nose drops, a gel or ointment, through a tube or catheter, by syringe, by packtail, by pledget, or by submucosal infusion. The compounds of the preferred embodiments of the present invention may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Examples of intranasal formulations and methods of administration can be found in PCT publications WO01/41782, WO00/33813, WO91/97947, and U.S. Pat. Nos. 6,180,603; 6,313,093; and 5,624,898. The latter-cited U.S. patents are incorporated herein by reference and for all purposes. A propellant for an aerosol formulation may include compressed air, nitrogen, carbon dioxide, or a hydrocarbon based low boiling solvent. The compound or compounds of the present invention are conveniently delivered in the form of an aerosol spray presentation from a nebulizer or the like. In some aspects, the active ingredients are suitably micronised so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. One embodiment provides one or more of the present peptides packaged into a device that can deliver a predetermined, and generally effective, amount of the peptide via inhalation, for example a nasal spray or inhaler.

The optimal concentration of the peptide or peptides will necessarily depend upon the specific peptide(s) used, the characteristics of the patient, and the nature of the viral infection for which the treatment is sought. These factors can be determined by those of skill in the medical and pharmaceutical arts in view of the present disclosure. Generally, a therapeutically effective dose is desired. A therapeutically effective dose refers to that amount of the compound that results in a degree of amelioration of symptoms relative to the status of such symptoms prior to treatment. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

Treatment is preferably commenced before or at the time of infection and continued until virus is no longer present or active in the respiratory tract. However, the treatment can also be commenced when given post-infection, for example after the appearance of established symptoms.

Suitable treatment is given 1-4 times daily and continued for 3-10, e.g. 8 days post infection depending upon the particular compound used.

The desired dose may be presented in a single dose or as divided doses administered at appropriate intervals, for example as two, three, four or more sub-doses per day.

The compound is conveniently administered in unit dosage form, for example, containing 10 to 1500 mg, conveniently 20 to 1000 mg, most conveniently 50 to 700 mg of active ingredient per unit dosage form, e.g. 1 mg/kg equates to 75 mg/75 kg of body weight.

The present peptides can also be provided as pharmaceutically acceptable salts. A "pharmaceutically acceptable salt" includes a salt with an inorganic base, organic base, inorganic acid, organic acid, basic amino acid, or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The dosage of the antiviral peptides of the present invention will vary with the form of administration and depend upon the particular antiviral peptide(s) chosen for the combination. Furthermore, it will vary with the particular host under treatment. In general, the antiviral peptides are most desirably administered at a concentration level that will generally afford antiviral effective results against the selected virus(es) without causing any harmful or deleterious side effects.

The present invention is further described with reference to the following illustrated Examples. Unless defined otherwise, all technical and scientific terms used herein have the same meaning as commonly illustrated by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well-known to one of ordinary skill in the art. The materials, methods and Examples are illustrative only and not limiting. All references cited herein are incorporated by reference.

EXAMPLES

I. Anti-Viral Activity of Peptides

Example 1

Protocols and Materials

Cell culture and virus: The procedures for growing Vero cells and preparing high titer stocks of HSV-1 KOS as described in Grau et al., *Invest. Ophthal. and Vis. Sci.* 30: 2474 (1989) were utilized. Vero cells were maintained in carbonate-buffered DMEM supplemented with 5% calf serum and 5% fetal bovine serum (regular medium). For some studies, cells were switched to serum-free DMEM buffered with 25 mM HEPES (pH 7.4) and allowed to adapt to that medium for 30 min prior to experimental treatments. Vero cells were seeded into wells (0.28 cm$^2$) of microtiter plates either at $3.5 \times 10^4$ cells/well for use 1 day later ($8 \times 10^4$ cells/well) or at $1 \times 10^4$ cells/well for use 3 days later ($2 \times 10^5$ cells/well).

Examples 10-20 were carried out in Vero cells cultured in Dulbecco's Modified Eagle's Medium (DMEM) supplemented with 5% defined supplemented calf serum and 5% fetal bovine serum (Hyclone, Inc., Ogden, Utah) and grown to confluence in 96-well plates ($2 \times 10^5$ cells/well). For the duration of each experiment, the medium was buffered with 25 mM HEPES (pH 7.3). The HSV-1 KOS mutant hrR3, which expresses *E. coli* β-galactosidase from the early ICP6 promoter (Goldstein, et al. (1988) Virology 166, 42-51.), was used for all studies. The virus was preadsorbed to cells by infecting pre-cooled cultures for 1 h at 4° C. (m.o.i.=0.02-0.03) and any free virus was rinsed off.

Madin-darby canine kidney (MDCK) cells were grown in modified Eagle's Medium (MEM) supplemented with 10% fetal bovine serum, 2 mM glutamine, and antibiotics as described above for Vero cells.

The PR8 strain of Influenza was obtained from Dr. Stacy Schultz-Cherry (Department of Medical Microbiology and Immunology, University of Wisconsin Medical School) and was propogated in the allantoic cavities of 11-day-old embryonated chicken eggs for 48 to 72 hrs. at 35° C. The allantoic fluid was harvested, centrifuged at 2,000×g for 10 minutes and stored at −80° C. Virus was titered by serial dilution and titers are reported as Tissue Culture Infectious Doses (TCID$_{50}$) fifty percent. The Influenza A virus strain A/Sydney/05/97, H$_3$N$_2$, was obtained from the Wisconsin State Laboratory of Hygiene (Madison, Wis.) and was prepared by infecting MDCK cells at a multiplicity of infection of 0.01, harvesting the infected cells when the cytopathic effect in the plates was 90%, centrifuging the solution at 2,000×g for 10 minutes and storing the virus supernatants at −80° C. The method for Influenza virus preparation is described in Schultz-Cherry and Hinshaw J. Virol. 70, 8624-8629 (1996).

Plaque reduction assay: Confluent Vero cell cultures in microtiter plates were infected for 1 hour at 37° C. in 40 µL of medium. Except where indicated, peptide treatments in 40 µL of medium lasted from 1 hour before through 1 hour after infection. At the end of the adsorption period, the cultures were re-fed with 100 µL of regular medium. Plaque formation was scored 2 days later and the number of plaques scored per well was normalized to the number counted in the absence of peptide. Using an ocular micrometer, plaque size ($\pi/2 \times L \times S$) was determined by measuring the largest plaque diameter (L) and the diameter at a 90° angle to that (S). The size of each of the first 40 scored plaques was measured except when a plaque included less than 10 rounded cells or touched the side of the well.

Yield reduction assay: Three days post-infection, Vero cell cultures in microtiter plates were frozen (−80° C.) and thawed (37° C.) three times. Cells were suspended by repeated pipetting and microtiter plates were spun for 10 min at 700×g in a Beckman model TJ-6 tabletop centrifuge. The virus-containing supernatants were serially diluted in regular medium and titered on Vero cells. Plaques were counted after staining the monolayers with crystal violet as taught by Grau et al., *Invest. Ophthalmol. Vis. Sci.* 30:2474 (1989).

Attachment assay: HSV-1 KOS was labeled with [$^{32}$P]-orthophosphate to a specific activity of 0.01 cpm/pfu. Briefly, Vero cells were infected at a m.o.i. of 5.0 and at 6 hours post-infection, [$^{32}$P]-orthophosphate (0.5 mCi/mL) was added. At 18 hours post-infection, the cells and culture medium were harvested separately. The cells were subjected to 3 freeze-thaw cycles and cell debris was pelleted by centrifugation at 2000×g for 10 min. The freeze-thaw supernatant was combined with the media and virus was pelleted by centrifugation through a 26% sucrose gradient cushion as taught by Visalli et al., *Virus Res.* 29:167 (1993). The viral pellet was resuspended in PBS for use. Confluent Vero cell cultures in microtiter plates were switched to serum-free DMEM, chilled on ice, and maintained at 4° C. After 30 min, peptides were added and 60 min later, cells were incubated for 2 hours with $^{32}$P-virus ($2 \times 10^4$ cpm/well). After labeling, cells were rinsed with ice-cold medium. Bound $^{32}$P was then quantitatively extracted with 1% SDS and 1% Triton X100 in PBS and counted in a Beckman LS5801 liquid scintillation counter.

Release of preadsorbed virus into the culture medium: Virus preadsorbed to Vero cells (m.o.i.=0.02) was exposed to heparin (porcine intestinal mucosa; Sigma-Aldrich Co., St. Louis Mo.; #H9399) or to peptides in 40 µL of serum-supplemented DMEM. After 1 h at 4° C., the culture medium and two 40 µL rinses were collected and pooled from eight identically treated wells. Pooled samples were centrifuged at 14,000×g in an Eppendorf 5415 centrifuge for 99 min at 4° C. or they were first adjusted to 0.5 M NaCl by adding 2 M NaCl dissolved in serum-supplemented DMEM prior to centrifugation. Supernatants were aspirated, the pellets were resuspended in 120 µL serum-supplemented DMEM and duplicate 50 µL aliquots were assayed for infectivity in Vero cell cultures. Calculations of the amount of released virus assumed 47% virus recovery in the centrifugation step, since control experiments had established that 47% of virus input was recovered regardless of whether the virus was sedimented in the presence or absence of 0.5 M NaCl.

Inactivation of virions: To assess the ability of peptides to inactivate virions, $3-4 \times 10^6$ pfu/mL of virus was mixed on ice with peptide in serum-free DMEM and incubated for 1 h at 4 or 37° C. Aliquots (10 µL) were diluted 1000-fold into peptide-free serum-supplemented DMEM at 23° C. and 50 µL aliquots were assayed in triplicate for infectivity in Vero cell cultures (dilution assay). Alternatively, 10 µL aliquots were diluted into 1 mL of ice-cold peptide-free serum-supplemented DMEM and the virus was pelleted as described above (centrifugation assay). Viral pellets were then resuspended in 250 µL serum-supplemented DMEM and 50 µL aliquots were assayed in triplicate for infectivity in Vero cell cultures.

Trypsinization of virions: Peptide-treated pelleted virions (see 'inactivation of virions') were resuspended in 250 µL serum-free DMEM and exposed to 0.005 or 0.01% trypsin (BioWhittaker #17-160E) for 1 h at 37° C. Trypsin was then inactivated by adding a 1.3-fold molar excess of soybean trypsin inhibitor (Sigma Chemical Co., St. Louis, Mo., #T-9003) and incubated for 10 min at 37° C. before 50 µL aliquots were assayed in triplicate for infectivity in Vero cell cultures. In controls, trypsin was inactivated before it was added to resuspended virions.

Trypsinization of peptides: Peptides dissolved in serum-free DMEM were exposed to 0.005 or 0.01% trypsin for 1 h at 37° C. The trypsin was then inactivated with a 1.3-fold molar excess of soybean trypsin inhibitor and the ability of the peptides to inactivate virions was tested as described above (centrifugation assay). In controls, trypsin was inactivated before it was added to the peptides.

LacZ$^+$ virus (hrR3) entry assay: Confluent Vero cell cultures in 96-well microtiter plates were switched to Hepes-buffered serum-free DMEM, cooled on ice to 4° C. for 30 min, and infected with hrR3 for 1 hour at 4° C. in 40 µL of medium. Unattached virus was removed by rinsing with ice-cold medium. Treatments with antiviral peptide SEQ ID NO:1, referred to as EB, or a control peptide which comprised the RRKK tetra-peptide (SEQ ID NO:16) attached to a scrambled version of the membrane transiting peptide R-R-K-K-L-A-A-L-P-L-V-L-A-A-P-L-A-V-L-A (SEQ ID NO:17) (referred to as EBX), or mock-treatments with peptide-free medium were carried out in serum-free DMEM as indicated. Virus entry was initiated by transferring cultures to 37° C. To inactivate any remaining extracellular virus, cultures were rinsed with PBS and exposed to low pH citrate buffer (40 mM citric acid, 10 mM KCl, 135 mM NaCl, pH 3.0, according to Highlander et al., *J. Virol.* 61:3356 (1987), for 1 min at 23° C. The citrate was rinsed off with PBS and cultures were maintained in serum-supplemented DMEM until they were fixed with 0.5% gluteraldehyde in 5×PBS for 30 min at 23° C., stained for β-galactosidase activity for 1 hour or overnight at 23° C. with X-gal (Fisher Biotech; BP1615-1) in 1×PBS containing 2 µM $MgCl_2$, 1.3 mM $K_4Fe(CN)_6$, and 1.3 mM $K_3Fe(CN)_6$, and scored for the presence of blue lacZ$^{30}$ cells.

Virucidal assay: HrR3 ($1.2 \times 10^6$ pfu/mL) was incubated with various concentrations of EB or EBX for 1 hour at 37° C. in 70 µL serum-free DMEM (pH 7.4). The treated virus was diluted 200-fold with serum-supplemented DMEM and assayed for infectivity approximately 1 hour later in microtiter wells seeded with Vero cells ($3.5 \times 10^4$ cells/well) 1 d earlier. Forty or 100 microliter volumes of diluted virus were adsorbed for 1 or 2 h at 37° C. and lacZ$^+$ cells were scored 8 hours later. In some experiments, aliquots of diluted virus were first dialyzed (Spectra/Por; MWCO 12-14,000) overnight at 4° C. against a 60-fold excess volume of Hepes-buffered serum-supplemented DMEM or forced by syringe through 0.22 µm membranes (Millex-GV; Millipore) before the remaining infectious virus was assayed.

Trypan-blue exclusion assay: Uninfected Vero cells in serum-free or serum-supplemented DMEM were treated for 1 hour at 37° C. with antiviral peptide SEQ ID NO:1 or control peptide EBX (SEQ ID NO:17), rinsed with PBS, stained for 5 min at 23° C. with 0.4% trypan-blue in PBS, rinsed again with PBS and air dried.

Electron microscopy: Purified HSV-1 KOS virions ($2.5 \times 10^7$ pfu/mL) according to Visalli et al., *Virus Res.* 29:167 (1993) were treated with 25 µM antiviral peptide SEQ ID NO:1 or the control peptide EBX (SEQ ID NO:17) in 40 µL serum-free DMEM buffered with 25 mM Hepes (pH 7.4) for 5 to 60 min at 4° or 23° C. Aliquots (10 µL) were adsorbed to pioloform poly-L-lysine-coated grids for 5 min at 23° C. Grids were rinsed with PBS, stained with 2% phosphotungstic acid (PTA) in water adjusted to pH ~6, and air dried. Alternatively, virus was pre-adsorbed to grids and treated with peptides thereafter. A total of $4 \times 10^9$ pfu/mL of purified HSV-1 KOS in 5 µL PBS was applied to the coated grids for 5 min at 23° C., and the grids were rinsed once with serum-free DMEM buffered with 25 mM Hepes (pH 7.4) and treated with 15 µL of 5 mM EB or EBX in the same medium for 30 min at 37° C. The pH of highly concentrated solutions of antiviral peptide SEQ ID NO:1 and EBX was re-adjusted to 7.4 with NaOH prior to use. To prevent evaporation of the peptide-containing solutions, each grid was held in a Hiraoka flexible staining plate and covered with a miniature bell jar made from an 0.5 mL polypropylene micro-centrifuge tubes, small enough for the 15 µL to fill half of the bell jar facing the coated surface of the grid. The entire assembly was then incubated in a moist chamber for 30 min at 37° C. After treatment, grids were rinsed twice with DMEM and once with PBS before they were stained with PTA and dried. Grids were examined in a JEOL JEM-1200EX electron microscope at magnifications of 15,000 and 40,000×.

Peptide Synthesis: Synthesis and analysis of peptides was done at the Biotechnology Center of the University of Wisconsin-Madison. Synthesis was carried out at a 25 pmole scale using an automated synthesizer (Applied Biosystems Model 432A "Synergy") following the principles initially described by Merrifield, *J. Am. Chem. Soc.* 85:7129 (1963) with modifications by Meienhofer et al., *Int. J. Peptide Protein Res.* 13:35 (1979) and Fields et al., *Peptide Res.* 4:95 (1991). The cleaved peptides were precipitated with cold t-butylmethylether, dissolved in water, and examined by analytical HPLC (purity) and electrospray ionization mass spectroscopy (molecular mass, see Table 1). Peptide concentrations in solution were determined by analytical HPLC and from absorbance readings at 215 and 225 nm as taught by Segel, *Biochemical Calculations*, $2^{nd}$ ed. John Wiley & Sons, Inc., New York, N.Y. (1976).

Peptides

In vivo activity against Herpes virus: The antiviral peptides according to the present invention demonstrate in vivo activity when topically applied, e.g. in a prophylactic manner. HSV-1 strain KOS was incubated in vitro for 1 hour with either the EB peptide or the EBX peptide at a concentration of 25 µM at room temperature in PBS. Groups of ten mice each were then infected via corneal scarification with $5.0 \times 10^5$, plaque forming units as described previously (Brandt et. al., J. Virol. Meth. 36, 209 (1992). This example demonstrates that virus treated in vitro with peptide had reduced activity in vivo.

Briefly, the mice were anesthetized with halothane, the cornea was scratched 3 times horizontally and 3 times vertically, and a 5 µL drop containing virus was placed on the cornea. The mice were then returned to their cages and allowed to recover. A control group infected with KOS but not exposed to peptide was also included. The mice were not treated with peptide after infection.

Repeated induction of cellular resistance to viral infection by successive exposures to the EB peptide. Confluent Vero cell cultures in microtiter plates ($2 \times 10^5$ cells/well) were exposed to EB for 1 h at 37° C. The peptide was rinsed off and some cultures were infected in the absence of peptide with untreated virus (9100 pfu/well hrR3) either immediately (●) or after an 8.5 h incubation in peptide-free medium (○). Additional cultures were exposed to EB for a second time (1 h at 37° C.) 8.5 h after the first exposure before they were infected (Δ). In all cultures infectivity was scored 8 h after infection by staining with X-gal and means of triplicate determinations with S.E. of the means are indicated. No cytotoxic effects were seen in mock-infected cultures stained with trypan blue. Throughout the experiment cells were kept in Hepes-buffered serum-supplemented DMEM.

In vitro activity against Human Immunodeficiency Virus: Stock preparations of HIV strain IIIb were prepared as taught by (Bartz, S. R., Pauza, CD, Ivanyi, J, Jindal, S, Welch, W J, Malkovsky M, 1994. J. Med. Primatol. 23, 151-154.) The CEMX174 cells were cultured as taught by (Bartz et. Al. see above). A total of $1.0 \times 10^6$ TCID$_{50}$ were mixed with various concentrations of KLA or TAT-Cd and then used to infect a $5.0 \times 10^4$ CEMX174 cells. The cultures were incubated for 3 days at 37° C. at which time the supernatants were collected. The amount of virus replication was then measured using a commercially available ELISA specific for p24 antigen. The IC$_{50}$ values were defined as the concentration of peptide that reduced the p24 antigen signal by 50% compared to untreated infected control cells.

In vitro Peptide Toxicity

Cell Lines

African Green Monkey kidney cells (Vero) were maintained in Dulbecco's Modified Eagles Medium (DMEM) supplemented with 10% serum (1:1 mixture of fetal bovine serum (FBS) and defined supplemented calf serum (CS), Hyclone, Inc. Ogden, Utah) as we described previously (Grau et al., 1989). The African Green Monkey kidney cell line CV-IPD was kindly provided by Dr. Janet Mertz (Dept. of Oncology, University of Wisconsin-Madison) and was grown in DMEM supplemented with 5% FBS. Human trabecular meshwork cells (TM-1) were grown in DMEM supplemented with 5% serum (1:1 mixture of FBS and CS). The HeLa cervical carcinoma cell line was obtained from Dr. Youngsook Lee (Dept of Anatomy, University of Wisconsin-Madison) and was cultured in DMEM medium supplemented with 10% FBS. The Human Foreskin Fibroblast cell line (DP-9) was provided by Dr. Donna Peters (Dept. of Pathology and Laboratory Medicine, University of Wisconsin-Madison) and was cultured in DMEM supplemented with 10% FBS. The T-B hybridoma cell line, CEMx 174 was maintained in RPMI medium supplemented with 10% FBS. Normal immortalized keratinocytes (NIKS, originally called Bcl-Ep/SL) and W12E (cervical carcinoma cell line with extra chromosomal copies of the HPV-16 genome) are available from Dr. Lynn Allen-Hoffmann (Dept. of Pathology and Laboratory Medicine, University of Wisconsin-Madison) and were maintained in F media supplemented with 5% FBS and 1% 1 OOX epidermal growth factor (Flores et al., 1999). All eight cell lines were incubated at 37° C. in a humidified 5% CO$_2$ atmosphere.

MTS Assay

The eight cell lines described above were plated in 96-well tissue culture plates at a concentration of $1.5 \times 10^4$ cells per well for Vero, HeLa, and TM-1 cell lines; $5 \times 10^4$ cells per well for CEMx 174, CV-1PD, NIKS, and W12E cell lines; and $2.5 \times 10^4$ cells per well for DP-9 cells. The cells were incubated in 37° C. atmosphere for overnight. Then, 20 µL of different concentrations (2 fold dilution) of peptides were added into the wells with the maximum concentrations of 100 µM for EB and EBX, 200 λM for bHOM and bHOM-FF, and 400 µM for TAT-C and $n_{55,56}$ TAT-C. The assays were done in duplicate. For control wells, 20 µL of peptide-free media were added. The plates were then incubated at 37° C. overnight. The next morning, 20 µL of the Celititer 96® AQ$_{ueous}$ One Solution Cell Proliferation Assay reagent (Promega, Madison, Wis.) was added to each well in 120 µL of culture medium with peptide. The plates were further incubated for 2 hrs at 37° C. in a humidified, 5% CO$_2$ atmosphere and the absorbance at 490 nm was recorded using a 96-well plate reader (Biotek Instruments, Winooski, Vt.).

In vivo Peptide Toxicity (i) Cornea: Four-6-week-old female BALB/C mice (Harlan Sprague Dawley, Indianapolis, Ind.) were anesthetized by halothane inhalation (3-5%). A 2.0 µL drop of serum-free 5×DMEM solution containing 6.1 mM EB, 6.1 mM EBX, 7.5 mM TAT-C, 7.5 mM $n_{50,51}$ TAT-C, 7.5 mM TAT-Cd, or 11.2 mM bHOMd or serum-free DMEM only (control) was then placed on the cornea and the mice were returned to their cages. Each group consisted of 5 mice, except for 11.2 mM bHOMd, and 7.5 mM TAT-Cd, which consisted of 4 mice. Only the right eye in each mouse received the peptide. Treatments were given 4 times per day at least 2 hrs apart for 7 days. On days 1, 5, and 7, the mice were examined microscopically for evidence of blepharitis, punctate keratopathy, dendrite ulceration and geographic ulceration. Damage to the corneal epithelium was assessed by staining with 1.0% calcein and examination under a microscope with blue light. Blepharitis was scored: 1+ for noticeable puffy eyelids, 2+ for puffy eyelids with moderate crusting, 3+ for eye 50% swollen shut with severe crusting, and 4+ for eye totally swollen and crusted shut (Brandt et al., 1992). Punctate keratopathy, dendrite ulceration, and geographic ulceration were scored: 1+ for <25% of the cornea involved, 2+ for 25-50% involved, 3+ for 50-75% involved, and 4+ for >75% involved. The mean disease score for each group of mice on each day was calculated by the sum of disease scores in each group on each day divided by the numbers of mice in that group. On day 7, following the last treatment, the mice were sacrificed and the eyes were removed, fixed in 10% formalin, embedded in paraffin, sectioned (5µ each), and stained with hematoxylin and eosin as we have described previously (Brandt et al., 1996). Sections were then examined for evidence of damage to the cornea, sclera, lens, and retina.

(ii) Vagina: The same strain of mice and anesthesia procedures were used for the intravaginal study. Twenty-five µl of 6.1 mM EB, 7.5 mM TAT-C, 11.2 mM bHOMd peptides, 6.6% nonoxynol-9 (N-9), and PBS (control) were instilled to the vagina twice a day at least 4 hrs apart. Each group consisted of 5 mice. The following day, the mice were sacrificed by injection of 0.5 mL of 2.5% avertin (1:1 w/v of tribromoethyl alcohol and tertiary amyl alcohol, respectively) intraperitoneally. The entire reproductive tract was dissected, fixed in 4% paraformaldehyde for at least 24 hrs, embedded in paraffin, sectioned, and stained with hematoxylin and eosin. Sections including the vagina, cervix, uterus, fallopian tubes and ovary, were then examined for evidence of damage and inflammatory response.

In vivo activity against Influenza virus: Mice were lightly anesthetized with 3% Halothane and fifty microliters of virus ($1 \times 10^5$ TCID$_{50}$ per mL) in DMEM was given intranasally. The mice were returned to the cages and then monitored daily for mortality. The mice were weighed every other day to record weight loss. To measure viral titers, mice were infected as described above and at various times post-infection, the lungs were removed and viral titers determined by serial dilution and infection of chicken eggs as described above for preparation of viral stocks. All peptides were tested by incubating virus plus peptide for 60 minutes at 37° C. and then infecting the mice. The bKLA peptide was also tested in a separate group of mice for activity post-infection. For this group, the mice were infected as described above with virus that had not been exposed to peptide. At 24 hours post-infection and once at 48 hours, the mice were given a single dose of 50 microliters of bKLA peptide in phosphate buffered saline (0.5 mM) and mortality and weights were monitored as described above.

Example 2

Antiviral Activity of Antiviral Peptides

Figure 1A:
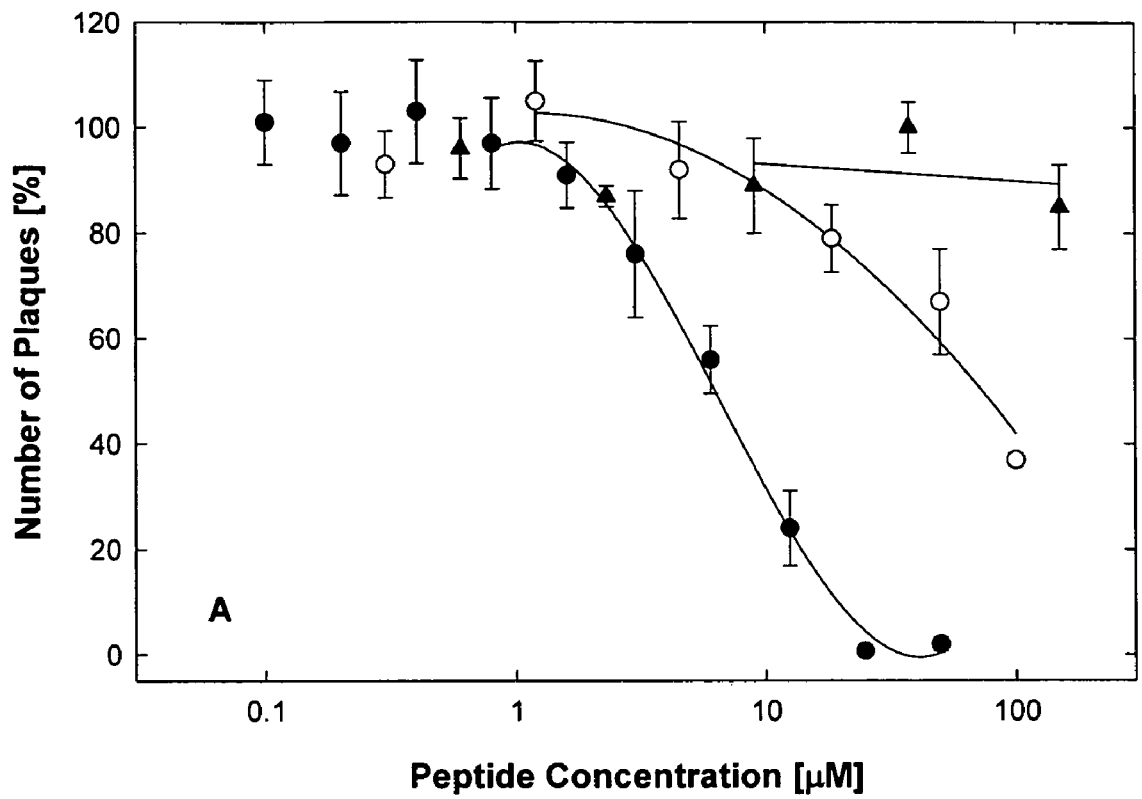
Figure 1B:
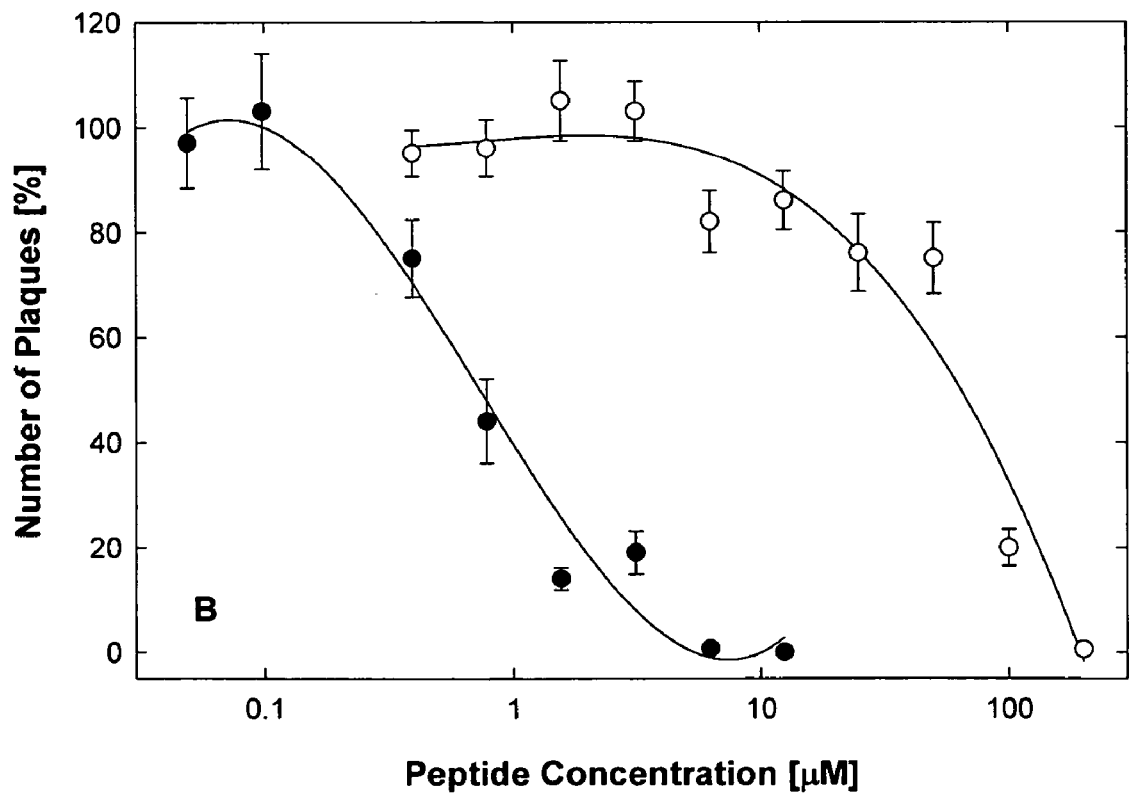
Figure 1C:
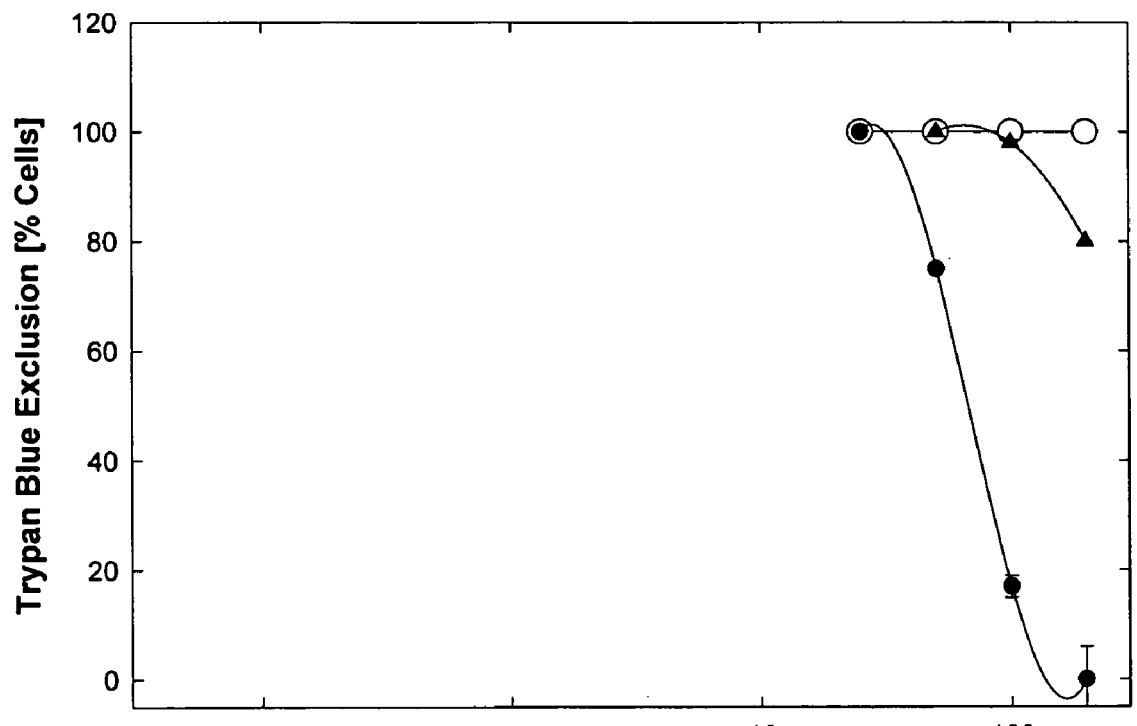
Figure 1D:
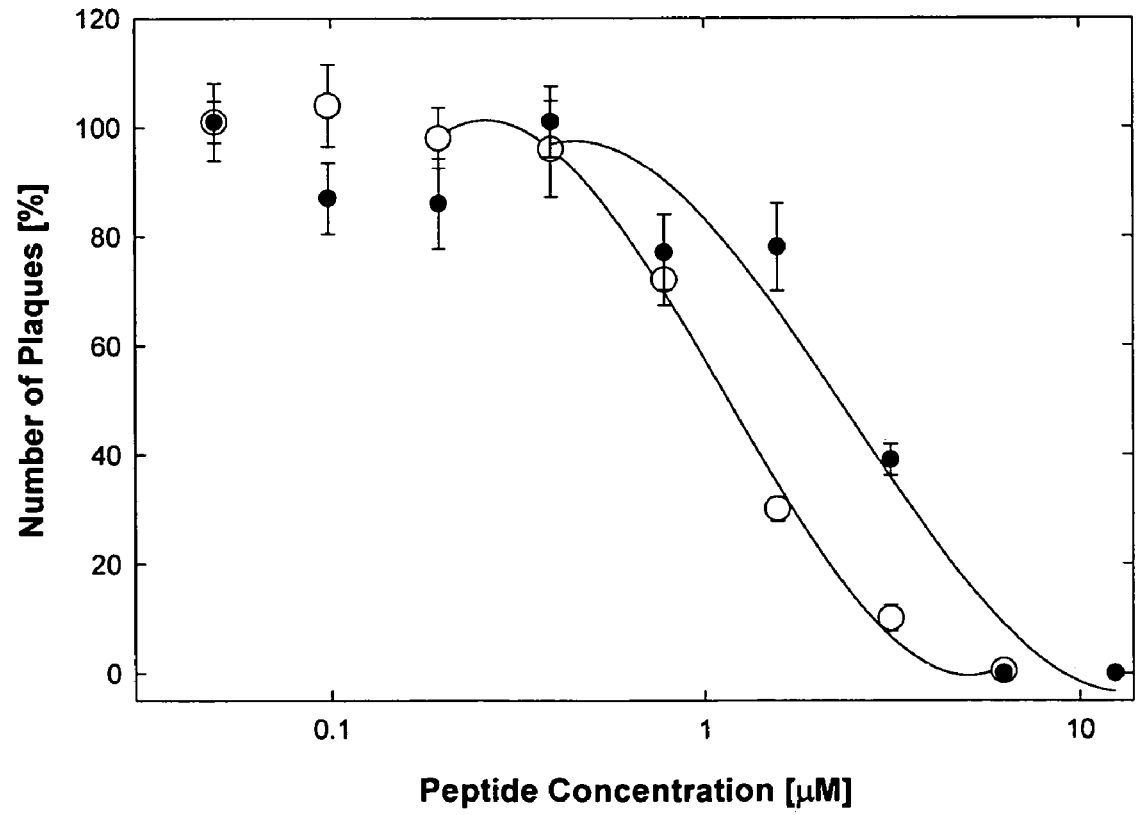
Figure 1E:
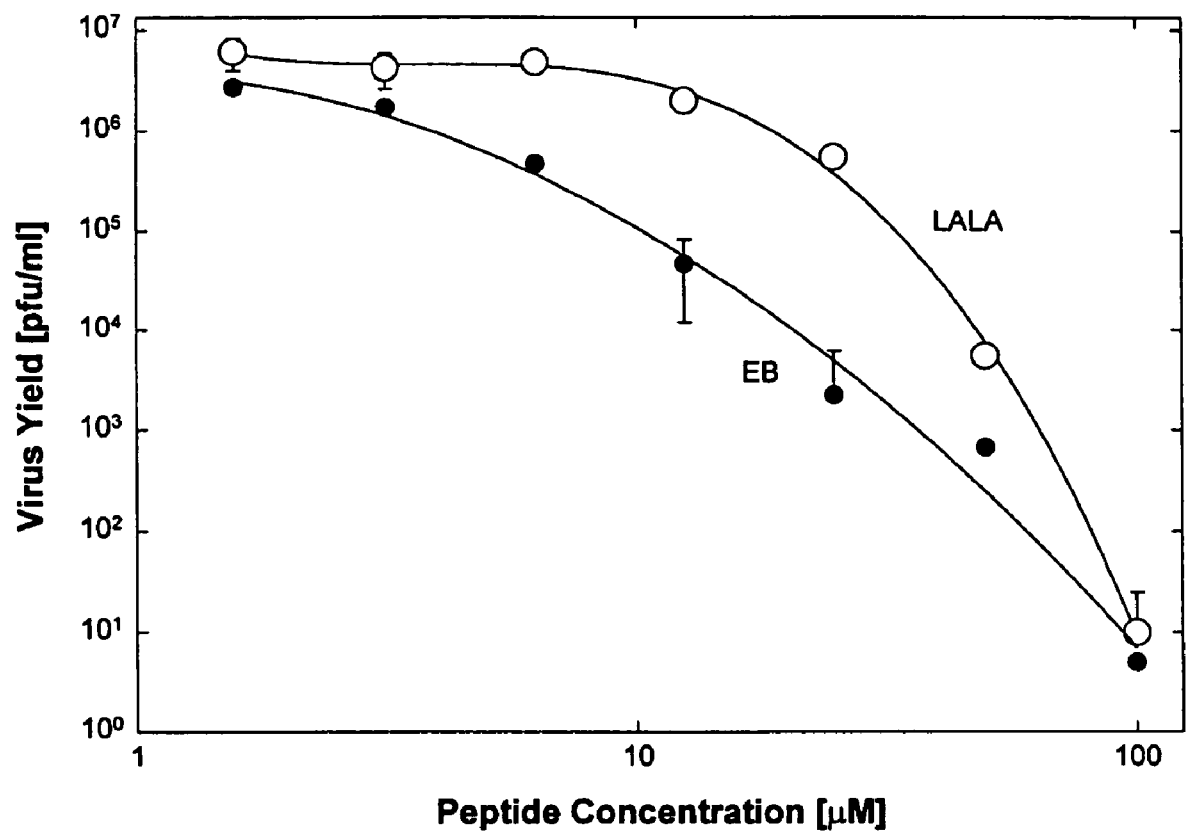

The antiviral peptide EB (SEQ ID NO:1), was an effective antiviral agent when present during infection of Vero cell cultures with HSV-1 KOS, blocking plaque formation as shown in FIG. 1A (●), FIG. 1B (●) and FIG. 1D (○); and reducing virus yields by up to eight orders of magnitude depending on concentration (see FIG. 1E). Compared to a control peptide FIG. 1A (○) nd FIG. 1B (○) EBX, the antiviral peptide EB was a far more effective antiviral, blocking infections at 10 or 100-fold lower concentrations depending on the presence (FIG. 1A) or absence (FIG. 1B) of serum.

The cytotoxic effects of antiviral peptide EB, as measured by trypan-blue exclusion in the absence of serum, were seen only at concentrations 100-fold higher (FIG. 1C, (●); $IC_{50}$=68 µM) than antiviral concentrations (FIG. 1B, (●); $IC_{50}$=0.7 µM). In the presence of serum, cytotoxic effects were seen first at 200 µM EB (FIG. 1C, (△)). No cytotoxic effects were associated with the control peptide EBX (SEQ ID NO:17) (FIG. 1C, (●)).

The charged amino-terminal R-R-K-K tetramer (SEQ ID NO: 16) was found to be useful for enhancing the solubility of the otherwise hydrophobic antiviral peptide EB, but does not have any important antiviral activity by itself. In the presence of serum, no antiviral activity was associated with the free R-R-K-K tetramer (SEQ ID NO: 16) at concentrations as high as 200 µM (FIG. 1A, (▲)).

In separate experiments, it was discovered that free R-R-K-K tetramer (SEQ ID NO:16) inhibited hrR3 infection of Vero cells under serum-free conditions at an $IC_{50}$ value of 1.3 mM (data not shown). It was also found that high (up to 100-fold molar excess), but non-antiviral concentrations of the free R-R-K-K peptide (SEQ ID NO:16) did not compete with antiviral peptide EB activity and could not relieve inhibition of hrR3 infections due to the antiviral peptide EB (data not shown).

To inquire whether derivatives of a membrane transiting protein sequence exhibited antiviral activity, a modified antiviral peptide (SEQ ID NO:3) referred to as EBPP, in which the central proline residue was moved to the carboxy-terminal end, was tested. This EBPP-peptide (Table 1) was twice as active as the original EB peptide in both, plaque (FIG. 1D) and yield reduction assays (data not shown).

Figure 2:
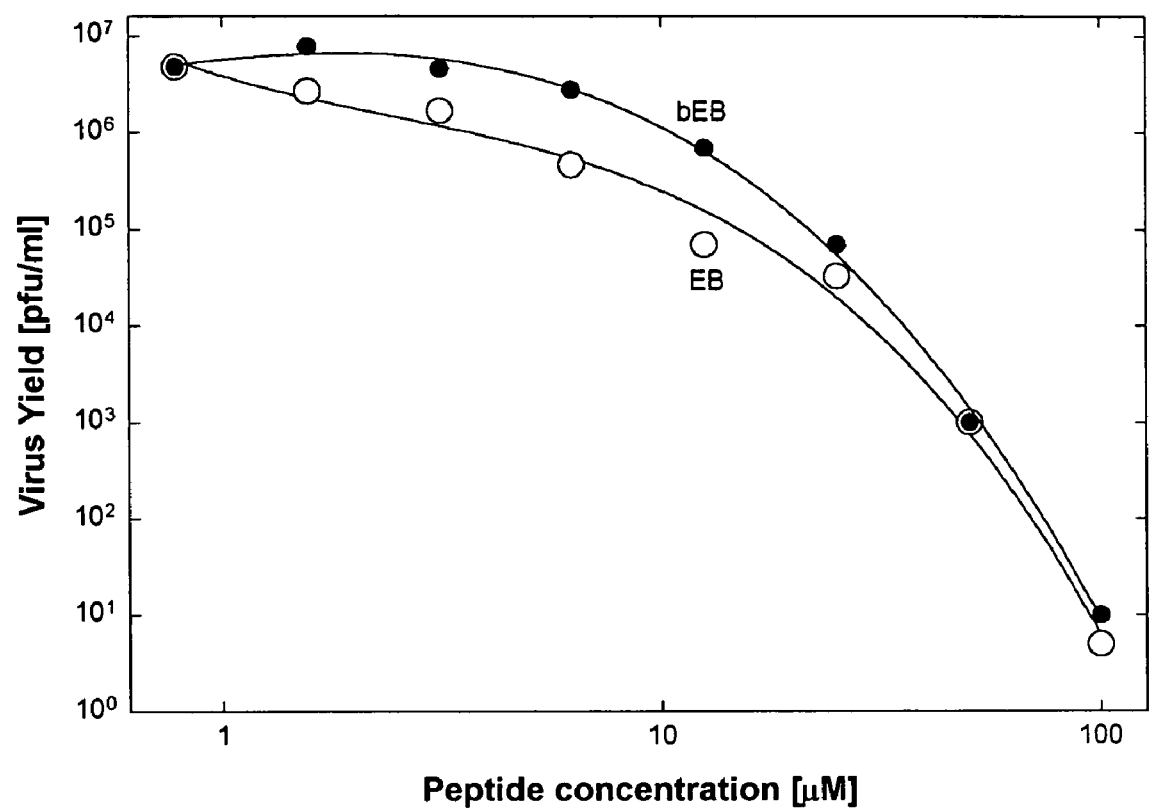

The EB peptide was modified to carry biotin (SEQ ID NO:2), and tested for activity as described above. As shown in FIG. 2, the biotinylated EB was essentially as effective as EB. Thus biotinylation of the peptide had a negligible effect on activity.

The antiviral activity of a number of other antiviral peptides and controls according to the present invention were determined as described above. The results are shown below in Table 3. As shown in FIG. 1E, antiviral peptide SEQ ID NO:4, referred to as "LALA", demonstrates similar antiviral activity as EB.

TABLE 3

Antiviral Activity of Antiviral Peptides

| Peptide | Entry Blocking Activity[1] | Virucidal Activity[1] 37° C. | Virucidal Activity[1] 4° C. | Anti-Free Virus Activity[1] | Cytotoxicity[1] |
|---|---|---|---|---|---|
| EB (SEQ ID NO:1) | 15-26 | 44 | 89 | | |
| bEB (SEQ ID NO:2) | 15 | 35 | 110 | 21 | 100 |
| EBX (SEQ ID NO:17) | None | None | None | | |
| bKLA (SEQ ID NO:5) | 11 | 15 | 45 | 4.5 | 15 |
| bKLAd$_{11,12}$ (SEQ ID NO:6) | 23 | 61 | 300 | | |
| bHOM-9 (SEQ ID NO:7) | 9-12 | 115 | None | 6 | 50 |
| bHOMd (SEQ ID NO:8) | 7 | 115 | None | | |
| bHOMFF (SEQ ID NO:9) | 40 | None | None | 34 | >>100 |
| bTAT-9 (SEQ ID NO:10) | 26 | None | None | 8 | ~200 |
| bTAT-9x (SEQ ID NO:12) | 67 | None | None | | |

[1]$IC_{50}$ values for all peptides in µm concentrations

Example 3

Comparison of Antiviral Activity of Antiviral Peptide vs. Acyclovir

Figure 3:
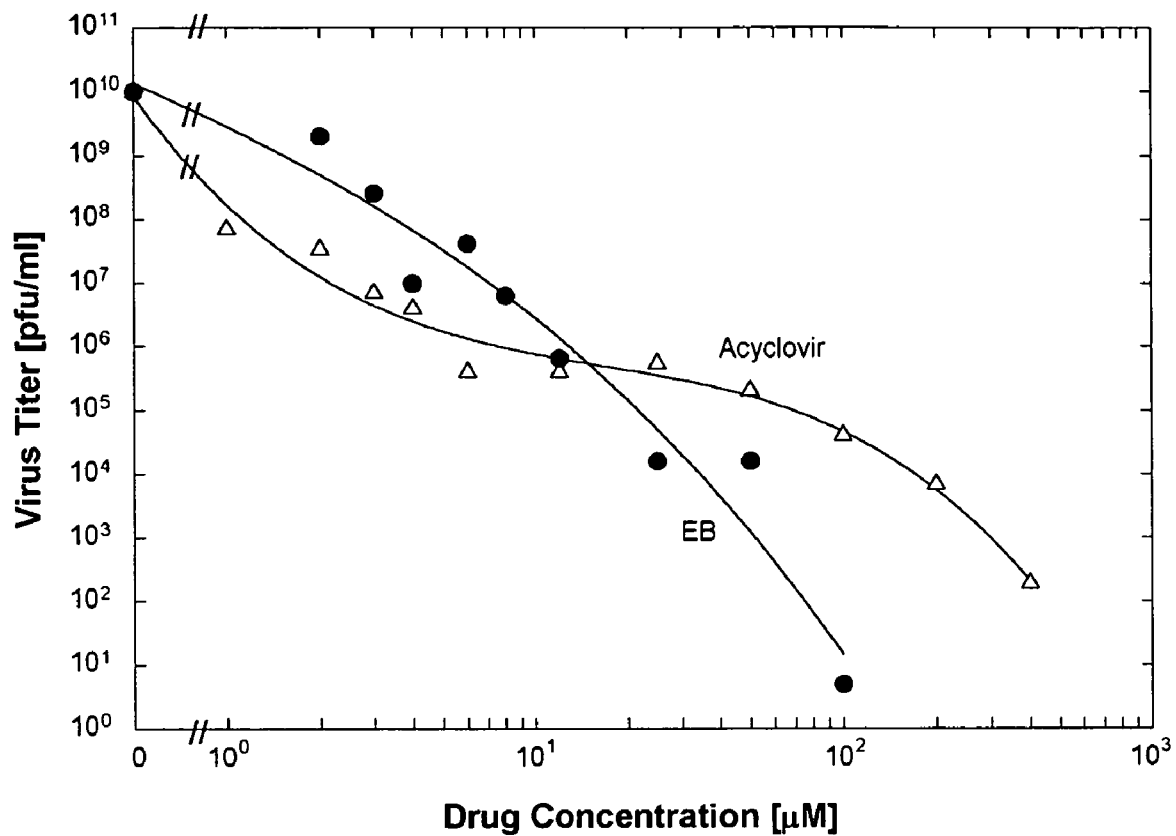

Vero cell cultures as prepared in Example 1 were infected with HSV-1 and assayed for virus production as described in Example 1. The antiviral activity of an antiviral peptide according to the present invention EB (SEQ ID NO:1) was compared to the antiviral activity of the current HSV antiviral nucleoside standard, acyclovir. The two inhibitors were added to the Vero cells one hour prior to infection with HSV. As FIG. 3 illustrates, although acyclovir shows the highest antiviral activity at low dosages, at high concentrations, i.e., those exceeding 10 µM of the active ingredient, EB showed the greatest antiviral activity.

Example 4

Early Effects and Effects on Plaque Size

Figures 4A, 4B:
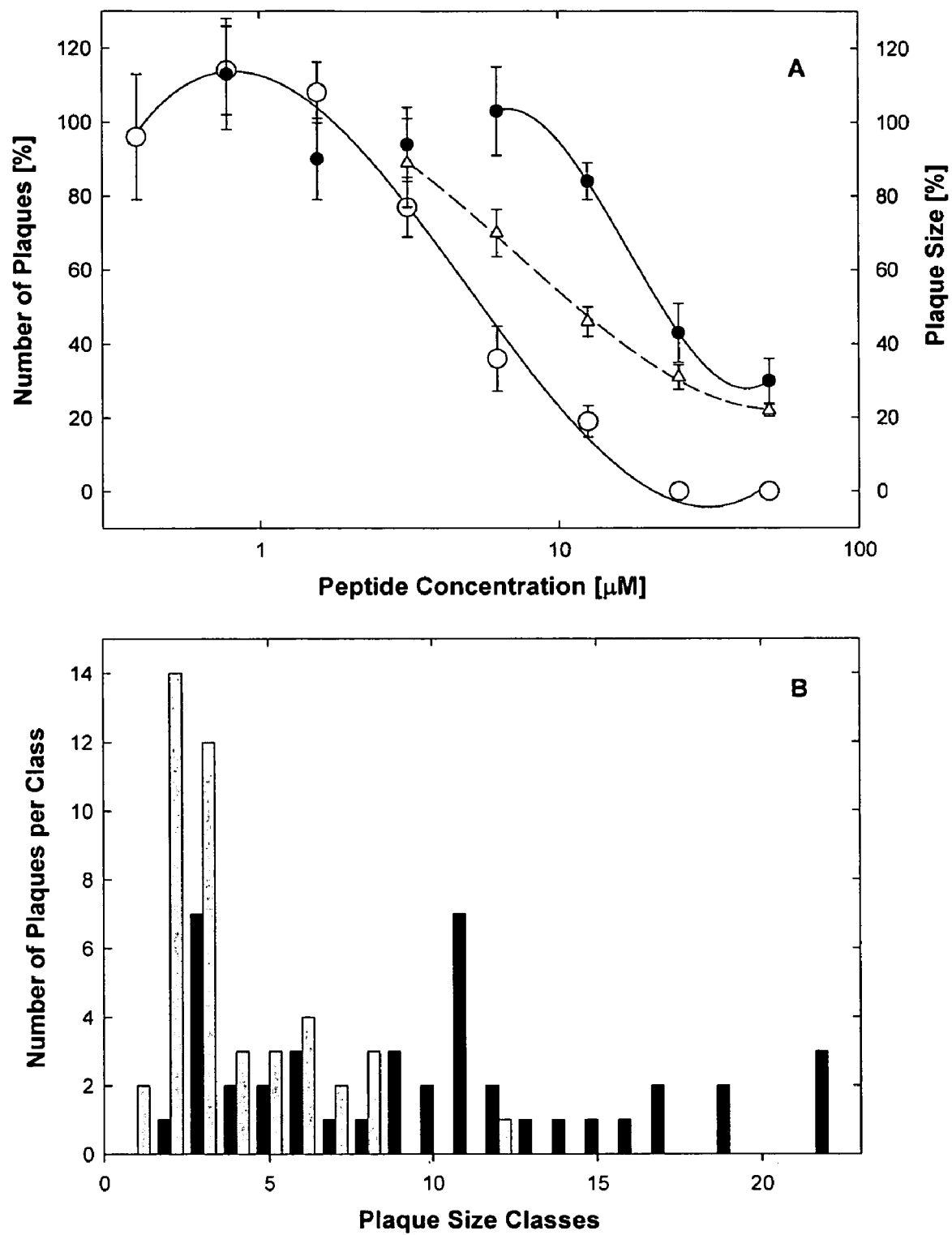

It was determined that antiviral peptides according to the present invention act early in the viral life cycle. As shown in FIG. 4A, EB was substantially more effective, when present during infection with HSV and 1 hour pre- and post-infection, than when present continuously starting 1 hour post-infection ($IC_{50}$=5.5 µM, (○) vs. $IC_{50}$=24 µM, (●)), respectively). Furthermore, when present before and during adsorption, EB had no effect on plaque size. When the EB peptide was present continuously after infection, plaque expansion was inhibited in a dose-dependent manner (FIG. 4A, (Δ); $IC_{50}$=12 μM). To ensure that individual plaques were measured reliably, cell cultures were infected at very low multiplicity (m.o.i. <0.01) and plaque sizes were measured microscopically very early (1 day post-infection). As shown in FIG. 4B, in untreated control wells, plaque size was broadly distributed (black bars; mean: 66,000±6200 μm$^2$), whereas addition of increasing concentrations of EB 1 hour post-infection progressively shifted the distribution towards smaller size classes (e.g., 25 μM EB significantly reduced the mean plaque size by 70% to 6900±2600 μm$^2$; t=6.88; shaded bars). In contrast, the presence of EB up to 1 hour post-infection had no effect on plaque size, even though the number of plaques was severely reduced compared to post-infection treatment. Thus, the combined mean plaque size after transient treatments with 6 and 12 μM EB (68,000±11,000 μm$^2$), was indistinguishable from the controls. EB appeared to act at an early stage of viral infection and reduced plaque size when added after infection.

Example 5

Aggregation of Virus by Antiviral Peptide

Antiviral peptides of the present invention were shown to aggregate virus by electron microscopy. Purified virus particles at high concentrations, as required for efficient visualization, were incubated with 25 μM EB, adsorbed to coated grids and stained with PTA. The results showed nearly all of the particles were seen in relatively few large aggregates. In contrast, untreated virus, or virus particles treated with 25 μM EBX were nearly all found individually and uniformly scattered over the grid surface. The individual PTA-stained virus particles within aggregates were virtually indistinguishable from control particles, indicating that EB did not induce gross structural abnormalities in the virus particles. The EB-induced aggregates were formed rapidly (<5 min) at room temperature as well as at 4° C.

Example 6

Antiviral Activity of Antiviral Peptide with Respect to Virus Input

Figure 5:
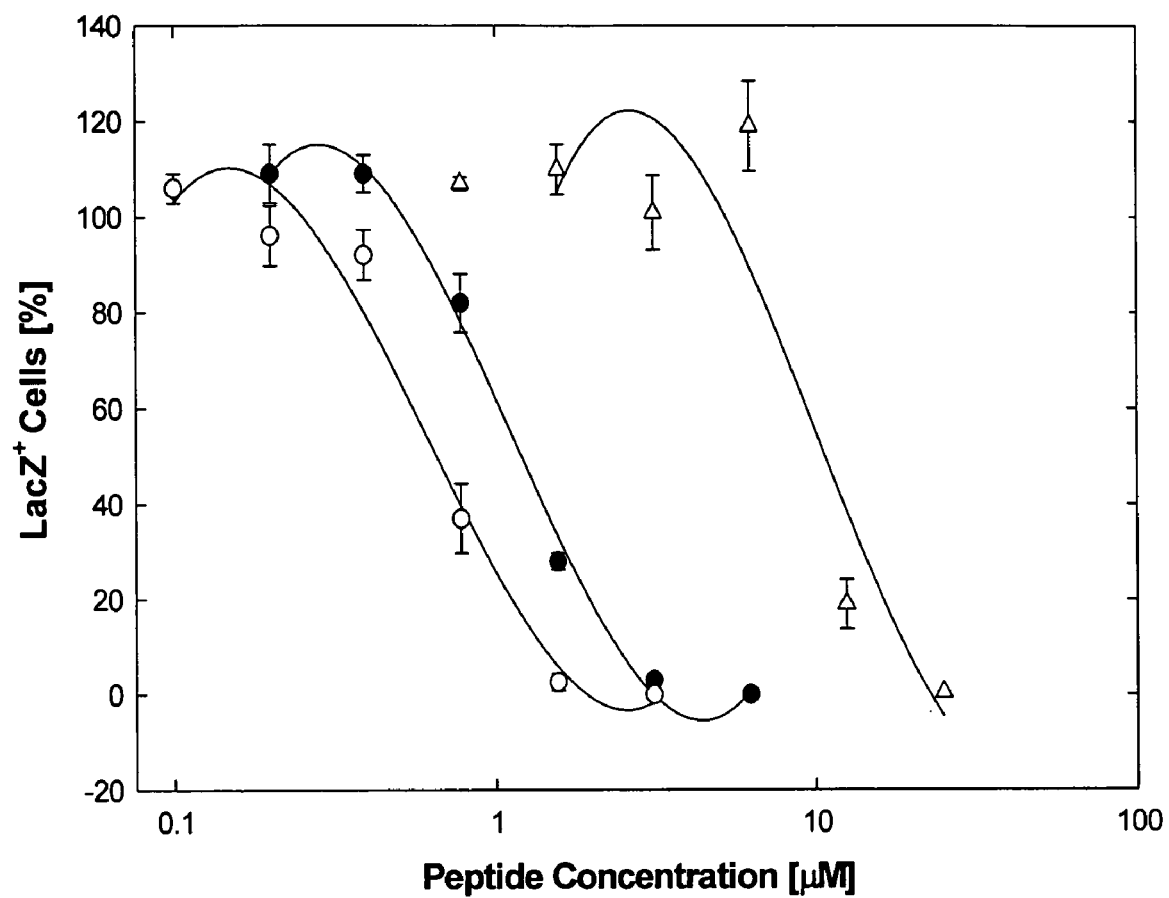

Cultures were infected with hrR3 at inputs of 19, 210, and 5700 pfu/well in the presence of various concentrations of EB and scored 8 hours later for lacZ$^+$ cells. The $IC_{50}$ values obtained were 0.66, 1.2, and 11 μM, respectively, as shown in FIG. 5.

Significantly, above the intermediate input of 210 pfu/well, there was a greater increase in the $IC_{50}$ with increasing virus titer than below that input, as shown in the inset in FIG. 5. The inverse relationship between $IC_{50}$ and virus titer would be expected if EB merely acted as an aggregation agent, which should operate more efficiently, i.e., with lower $IC_{50}$, at the higher virus input. Thus, viral aggregation does not make any major contribution to the antiviral activity of EB in these experiments. Furthermore, the fact that the antiviral activity of EB strongly depended on virus concentrations, suggests that that the antiviral peptides of the present invention interact with viral components.

Example 7

Inhibition of Viral Entry

Additional studies with pre-adsorbed hrR3 virus demonstrated that the antiviral effect or effects of an antiviral peptide of the present invention are related neither to virus adsorption nor to virus aggregation, but rather to inhibition of virus entry. In these studies, the hrR3 virus was pre-adsorbed to cells for 1 hour at 4° C. before ice cold 25 μM EB or EBX were added in serum-free DMEM. After an additional 1 hour at 4° C., cultures were shifted to 37° C. to initiate virus entry. At 15 min intervals following the temperature shift, any virus remaining outside the cells was inactivated by washing the cultures with low pH citrate buffer. Cultures were then rinsed and returned to peptide-free serum-supplemented DMEM until they were fixed and stained for β-galactosidase 8 hours after the temperature shift.

Figures 6A, 6B:
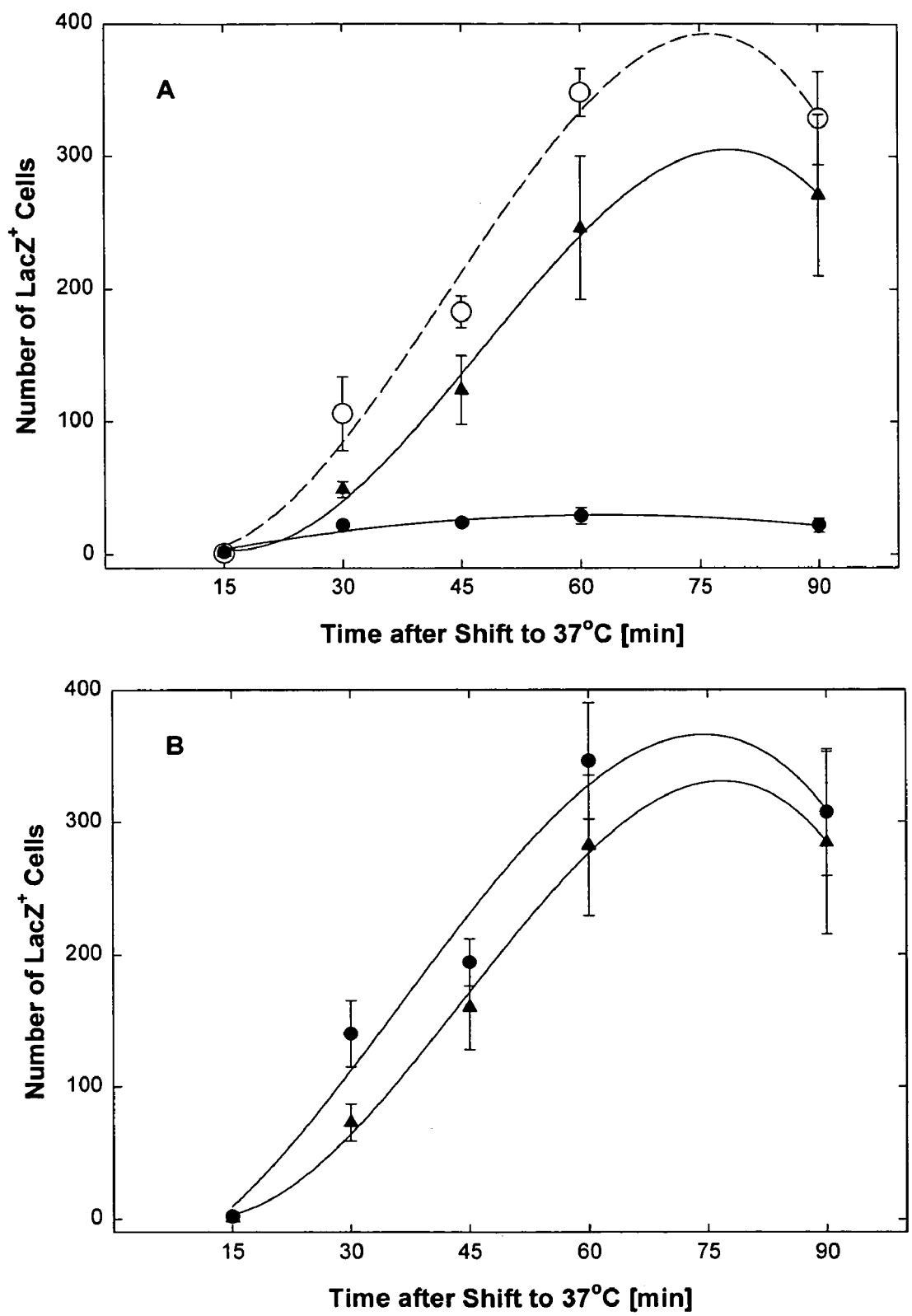

As shown in FIG. 6A, virus entry in mock-treated control cultures (○) was initiated 15-30 min after transfer to 37° C. and completed by about 60 min at a level of about 340 lacZ$^+$ cells per 6.5 mm$^2$ (or 1450 lacZ$^{30}$ cells/well). In cultures treated with the EB peptide, the number of lacZ$^+$ cells was reduced by >90% (●). The EBX peptide did not significantly reduce the number of lacZ$^+$ cells (▲). Essentially the same results were obtained when EB and EBX were added prior to virus adsorption (data not shown). When peptide was added immediately after each citrate treatment, EB no longer had any effect on the development of lacZ$^{30}$ cells (FIG. 6B, (●); cf. FIG. 6A, (○)). EBX also did not significantly inhibit the development of lacZ$^{30}$ cells when added immediately after the citrate treatments (FIG. 6B, (▲)). Thus, EB had no effect on the expression of the lacZ gene from the early ICP6 promoter, but selectively blocked viral entry.

Figures 7A, 7B:
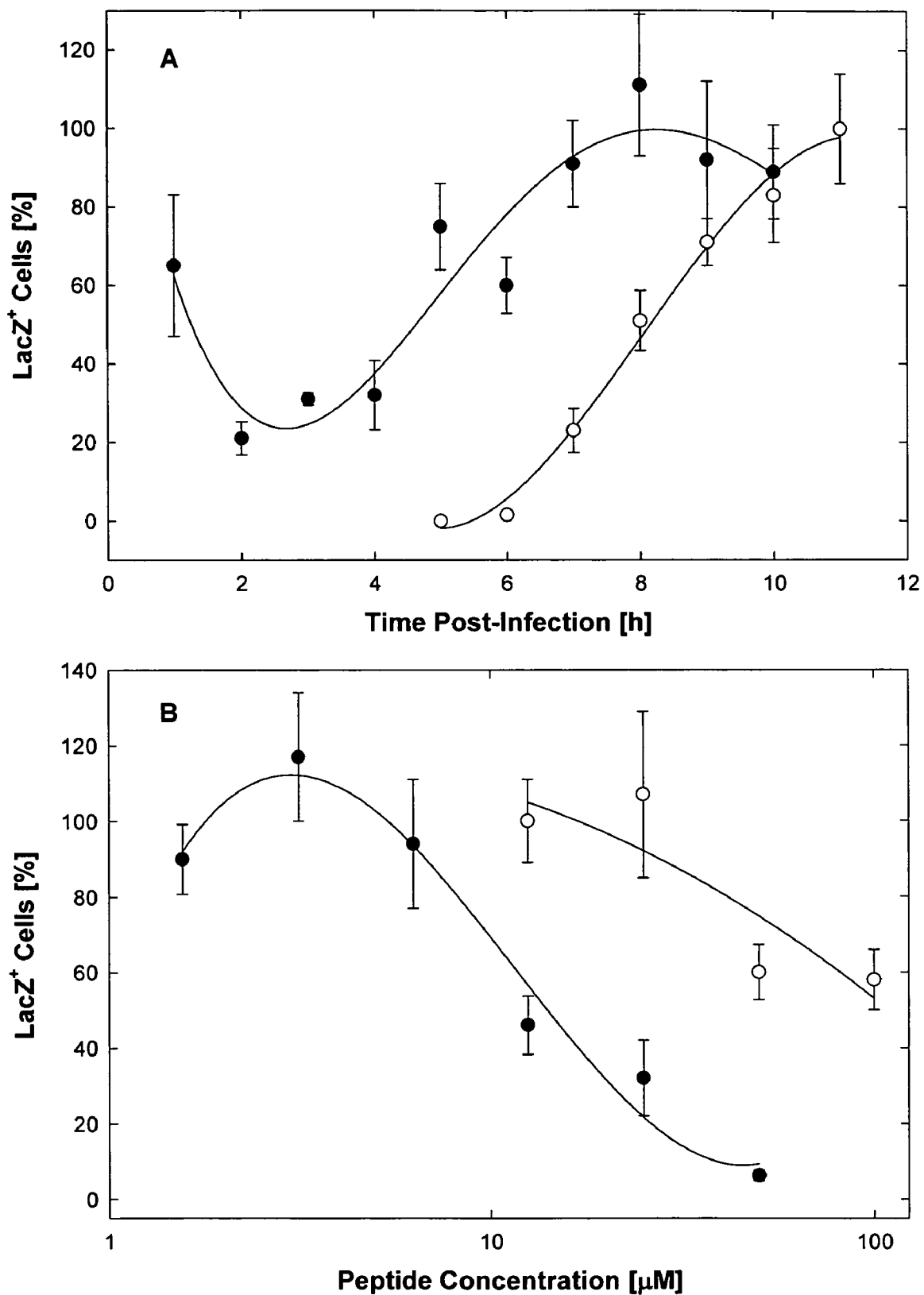

This conclusion is strengthened by the finding that the EB-sensitive phase of infection with pre-adsorbed virus clearly precedes expression of lacZ genes in hrR3 infected cells (FIG. 7A). Again, hrR3 was pre-adsorbed to cells for 1 hour at 4° C., unattached virus was rinsed off, and cells were kept for an additional hour at 4° C. Cultures were then transferred to 23° C. for 30 min before they were switched to 37° C. The more gradual change to 37° C. allowed cell layers to remain intact through subsequent frequent medium changes. Immediately following viral adsorption, cells were treated with 50 μM EB for 1 hour periods at consecutive 1 hour intervals. Between 1 and 4 hours post-infection, virus entry was inhibited by 70-80%. Thereafter, infection was no longer significantly inhibited (FIG. 7B, (●)). Parallel cultures were immediately fixed after mock-treatments and stained with X-gal. In these cultures, blue (lacZ$^+$) cells first appeared 7 hours post-infection and their number increased nearly linearly for the next 3 hours (FIG. 7A, (○)). By 7 hours post-infection, EB ceased to be inhibitory. Thus, EB only blocked virus entry during an early brief sensitive period and had no effect on the expression of the lacZ gene and the development of β-galactosidase activity once the virus had entered the cell. As shown in FIG. 7B, EB inhibited entry of pre-adsorbed virus in a dose-dependent manner with an $IC_{50}$=15 μM (●), whereas EBX was less effective ($IC_{50}$~100 μM; (○)).

Example 8

Virucidal Effects of Antiviral Peptide

Figures 8A, 8B:
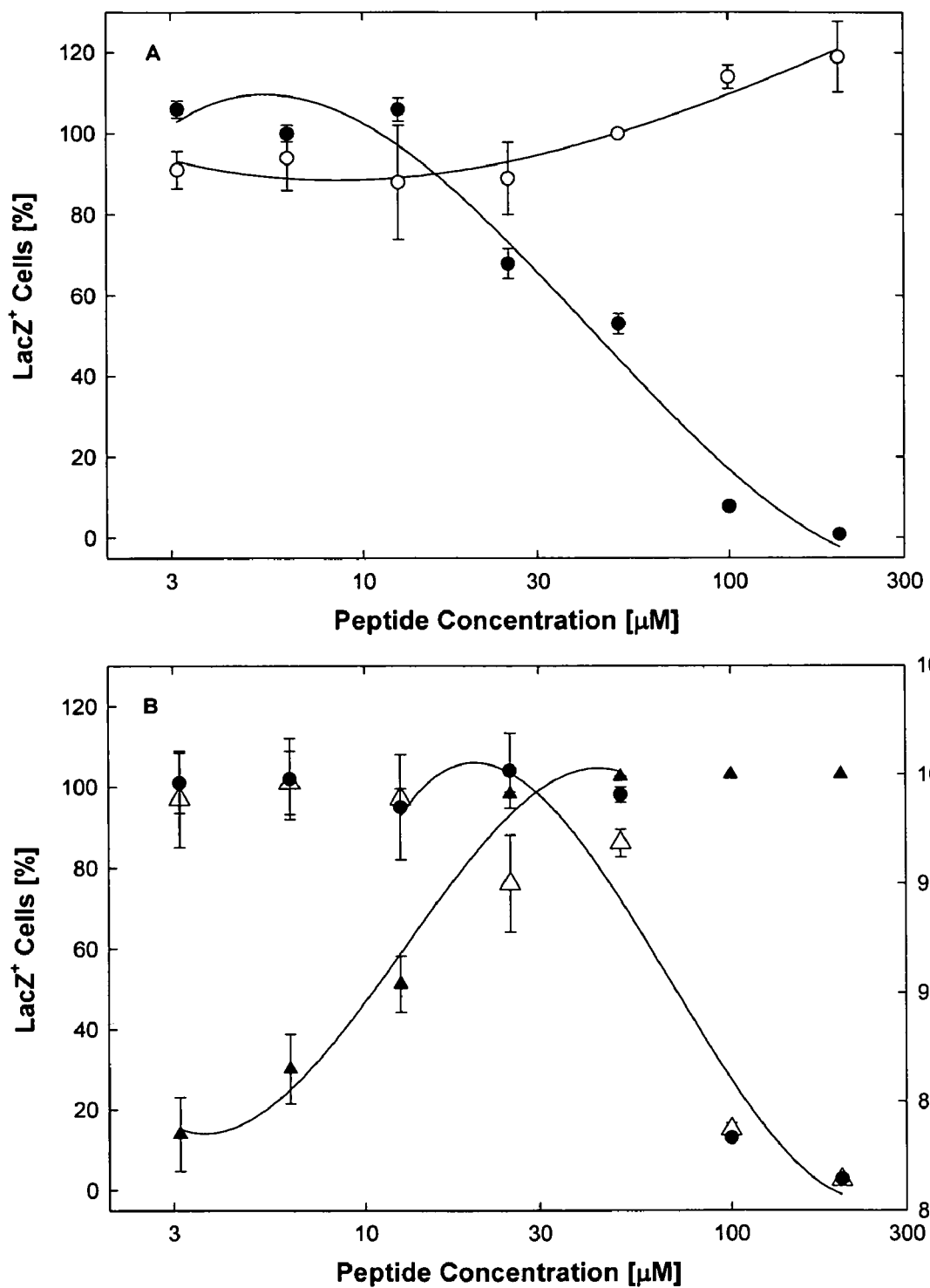

It was found that the binding of antiviral peptides of the present invention to virus particles leads to irreversible virus inactivation. Virucidal assays were performed with hrR3. In the first experiment (FIG. 8A), EB inhibited the infectivity of virions in a concentration-dependent manner with an $IC_{50}$=44 μM (●), whereas EBX had no inhibitory effect (○). In the second experiment, in which slightly higher concentrations of EB were required to achieve inhibition (FIG. 8B, (●); $IC_{50}$=69 μM), it was also found that the treated virions were irreversibly inactivated. That is, aliquots of EB-treated and then diluted virions could not be re-activated during overnight dialysis against serum-containing medium that could have trapped any reversibly-bound EB (cf. FIG. 1, (●); A vs. B). Instead, virions recovered after dialysis (31% at any EB concentration) remained inactivated exactly like the non-dialyzed controls (FIG. 8B, (Δ) vs. (●)).

To assess possible contributions of viral aggregation to viral inactivation, additional aliquots of EB-treated and subsequently diluted virions were filtered through 0.22 μm membranes before they were assayed for remaining infectivity. In the absence of, or at low concentrations of EB ($\leq 3$ μM), 80-85% of the virions were trapped on the membranes. The remaining virions, however, were retained only once exposed to higher EB concentrations, which enhanced membrane adhesion and/or caused viral aggregation (FIG. 8B, (Δ)). Such changes in the adhesive properties of virions were induced well below EB concentrations required for virus inactivation (FIG. 8B, (▲) vs. (●), (Δ)).

The effects of the most severe EB treatments were examined by electron microscopy of PTA-stained virions that had been pre-adsorbed to grids (to avoid aggregation) and exposed to 5 mM peptide. The EB-treated virions looked essentially the same as mock-treated virions, except that contours of the viral envelopes in the EB-treated particles were less pleomorphic, suggesting EB stabilized virions. At 5 mM, EBX had the same effect as EB.

Example 9

In vivo Activity of Antiviral Peptide

HSV-1 strain KOS was incubated for 1 hour with either the EB peptide or the EBX peptide at a concentration of 25 μM at room temperature in PBS. Groups of ten mice each were then infected via corneal scarification with 5.0×10⁵ plaque forming units as described previously (Brandt et. al., J. Virol. Meth. 36, 209 (1992)).

Figures 9A, 9B:
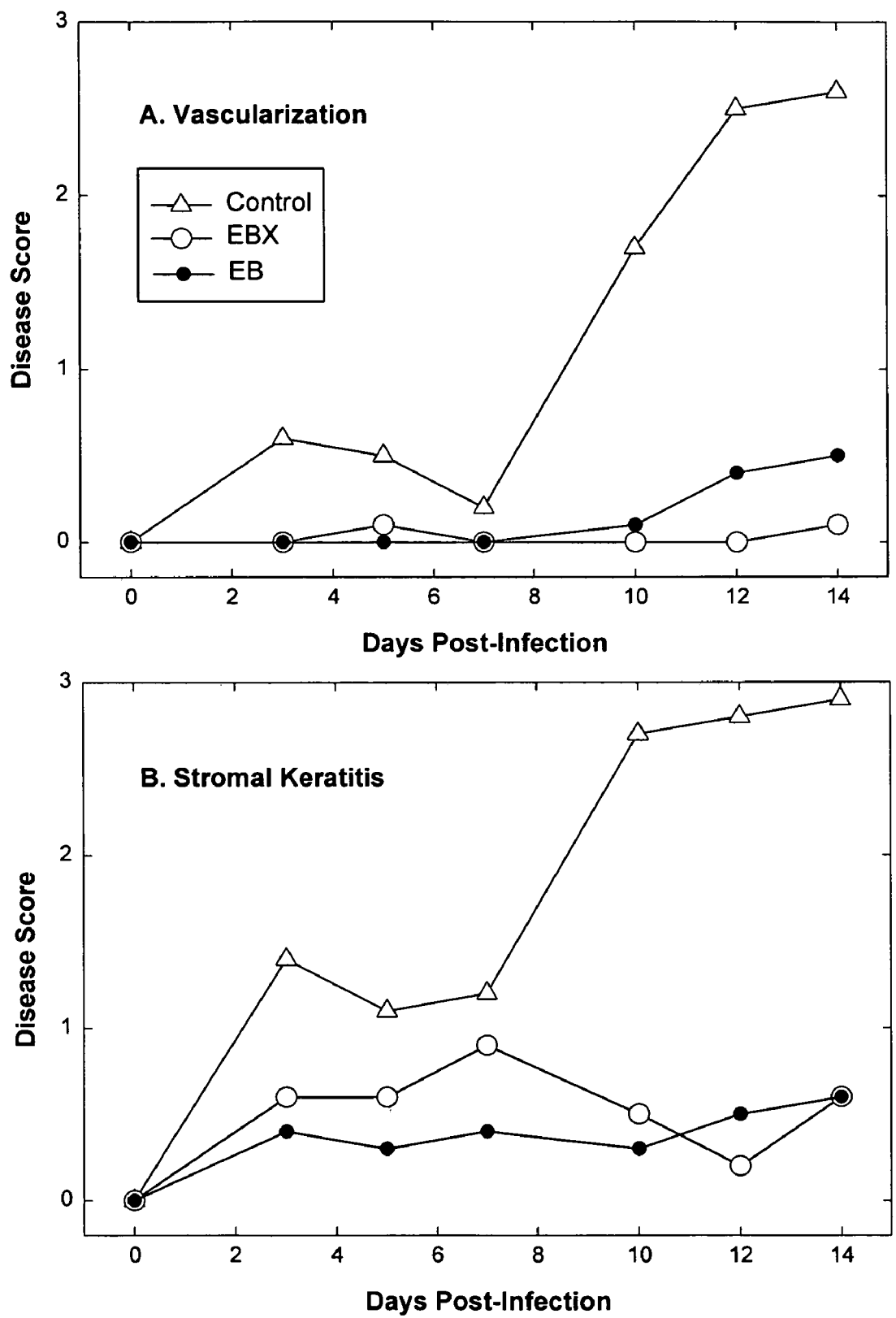

At various times post-infection, the severity of ocular disease was measured as described previously. Briefly, vascularization was scored: 0, no vascularization; 1+<25% of the cornea involved; 2+25-50% involvement; and 3+>50% involvement. Keratitis was scored: 0 no corneal clouding; 1+ cloudiness, some iris detail visible; 2+ cloudy, iris detail obscured; 3+ cornea totally opaque; 4+ cornea perforated and cloudy. Data are reported as the mean disease score on each day for each of the three groups. The results are illustrated in FIG. 9.

Example 10

Antiviral Activity Against Human Immunodeficiency Virus (HIV)

Figure 10A:
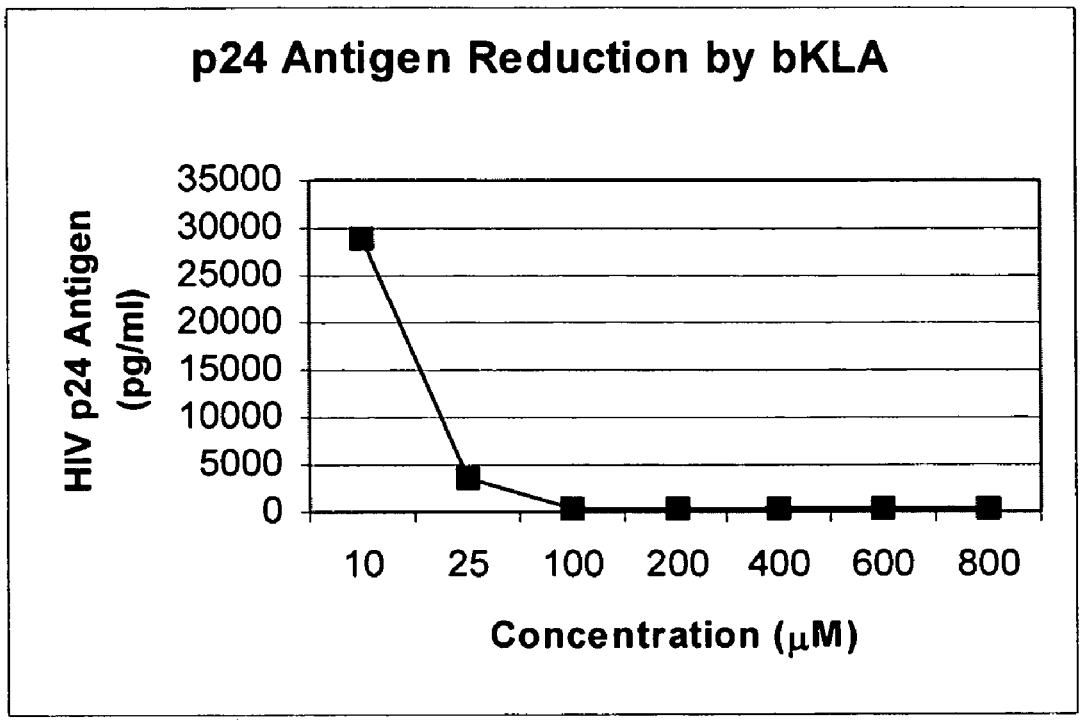
Figure 10B:
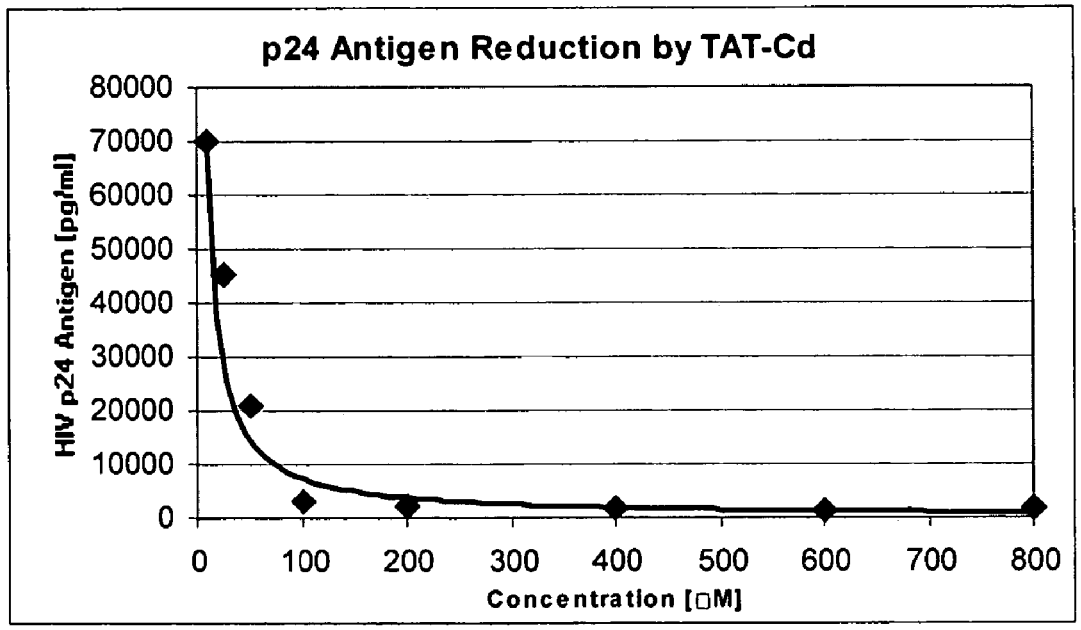
Figures 12A, 12B:
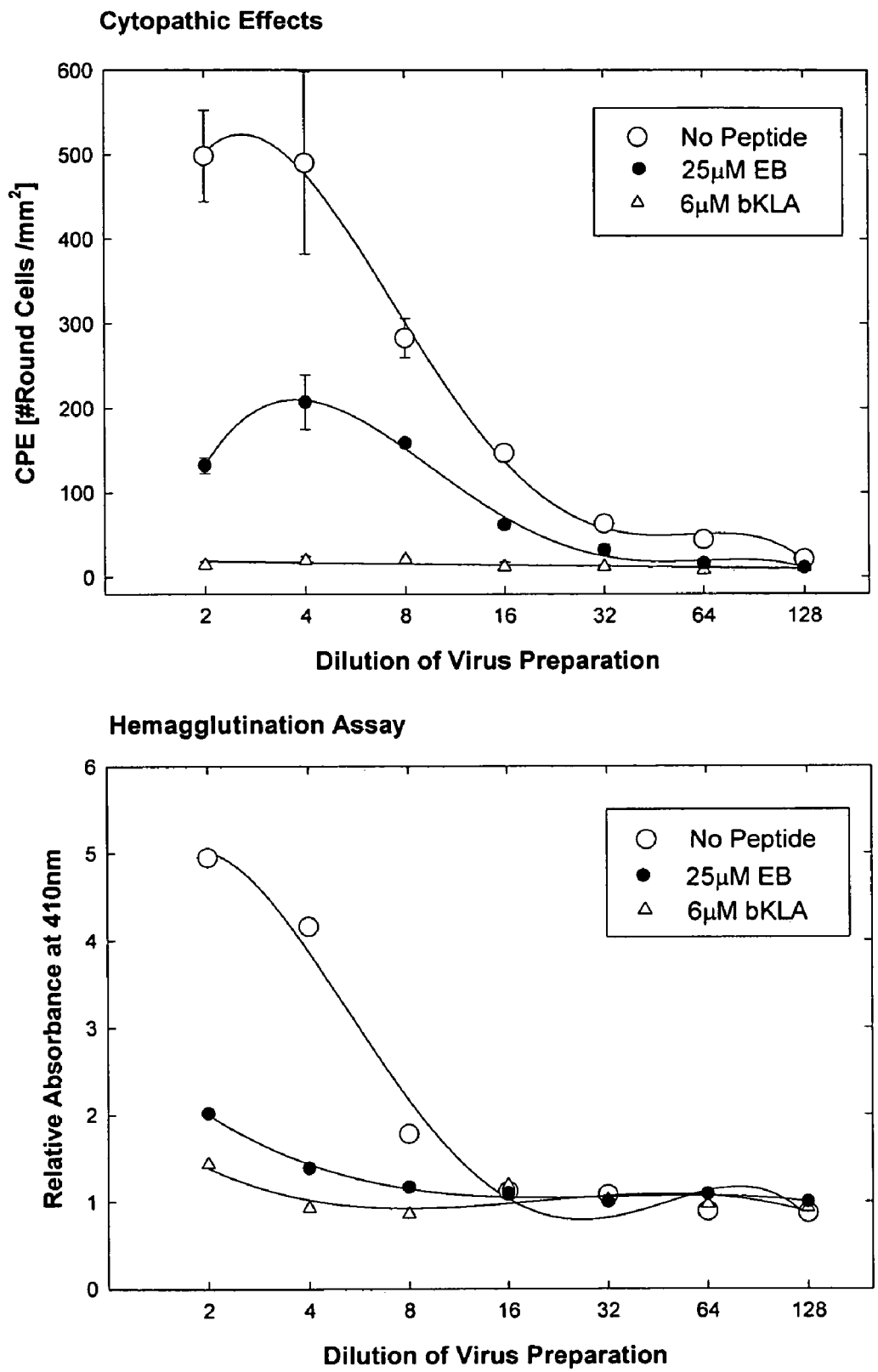
Figures 12C, 12D:
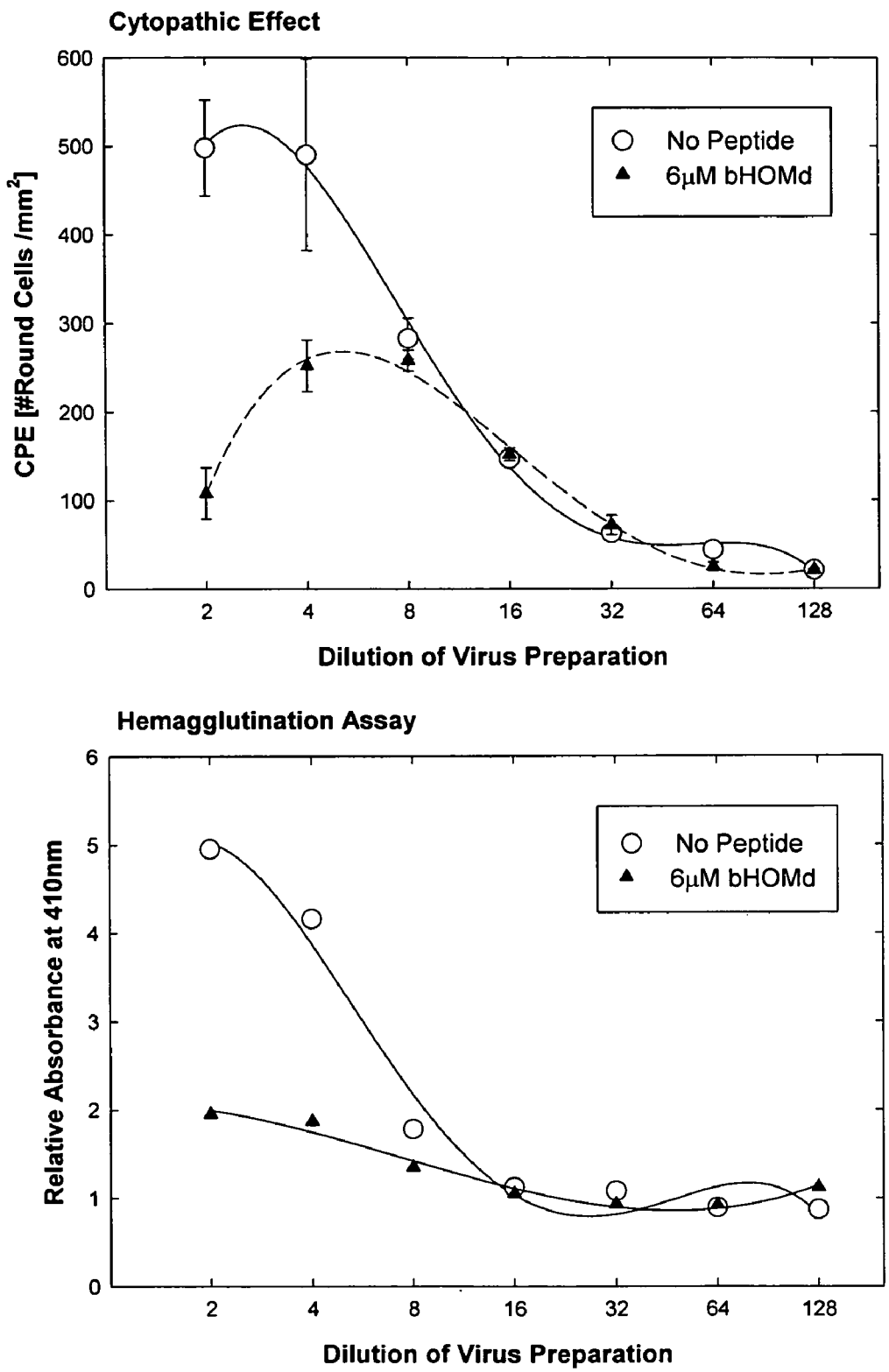

To test the activity of the peptides against HIV, HIV IIIb strain was mixed with various concentrations of either the KLA peptide or the TAT-Cd peptide and then mixed with CEMX174 cells. Three days post-infection, the amount of virus was quantitated by using a commercially available ELISA that measures p24 antigen amounts. As shown in FIGS. 10A and 10B, both KLA and TAT-Cd displayed antiviral activity with $IC_{50}$ values of 20 to 25 μM. We also tested HIV strains with differing co-receptor specificities (eg., X4, X5, or X4X5) and found that both peptides were active with $IC_{50}$ values of 20 μM or lower (data not shown). These results confirm that the peptides inhibit HIV.

Section I.B.—Influenza and Respiratory Infection

Example 11

Antiviral and Cytotoxic Effects of Peptides in MDCK Cells

Confluent layers of MDCK cells in 96-well plates were switched to Hepes-buffered serum-free DMEM and infected by adding a clinical isolate of influenza A virus (Sydney 05/97,$H_3N_2$, from the Wisconsin State Laboratory of Hygiene in Madison Wis.) in the absence of trypsin. The plates were centrifuged at 2000 rpm in a Beckman Model TJ6 centrifuge for 45 min at ~23° C., the medium was replaced with virus-free medium, and cytopathic effects and cytotoxic effects (trypan blue exclusion) were scored 1 day later. Peptides at the indicated concentrations were added to cells 2 h before infection and remained present throughout the experiment. Virus was exposed to the peptides 1 h prior to infection. Cytopathic effects were scored by counting rounded cells on top of the normal cell layer in an area of 0.25 mm² (100% corresponds to 175 rounded cells counted in control cultures). Scores are means of triplicate determinations with standard errors of the means.

Three of the tested peptides (bKLA, EB and bTAT-9) blocked infection with influenza A virus by >80% in the absence of cytotoxic effects. For the fourth peptide (bHOM-9), antiviral and cytotoxic effects were inseparable. The results for this Example are shown in FIGS. 11A, 11B, 11C and 11D.

Example 12

Antiviral Effects of Peptides Against Influenza A Virus and H5 Avian Influenza Virus MDCK cells were infected with serially diluted influenza A virus as described in the legend to FIGS. 12A, 12B, 12C, and 12D. Peptides (25 μM EB, 6 μM bKLA or 6 μM bHOMd) were added to cells and virus preparations 1 h before infection and remained present throughout the experiment. Eighteen hours after infection, cytopathic effects and trypan blue exclusion were scored and 100 μL supernatants were collected for hemagglutination tests. No cytotoxic effects were indicated by trypan blue staining. For the hemagglutination tests, 100 μL supernatants were mixed with 100 μL 1% Guinea Pig erythrocytes in PBS in 0.6 mL conical tubes and incubated at 4° C. until the erythrocytes had precipitated to the bottom and the sides of the tubes. The two precipitates were separated, lysed in 1% SDS and quantified by adsorbance readings at 410 nm. Relative adsorbance readings measure the fraction of erythrocytes slowly accumulating on the sides of the tubes. Antiviral activity against an H5 Avian Influenza virus was tested by mixing virus with various concentrations of EB or TAT-Cd, infecting MDCK cells, and then measuring viral induced cytotoxicity (release of LDH into the medium) using a commercially available ELISA for lactate dehydrogenase (LDH).

Alternative assays (scoring cytopathic effects and hemagglutination) provide similar estimates of the antiviral effects of peptides in MDCK cells infected with influenza A virus.

A representative of the HOM peptides (bHOMd) also blocks influenza A virus in the absence of cytotoxic effects. The results for this Example are shown in FIGS. 11A and 11B.

An example of the antiviral effect against an H5 Avian Influenza virus strain is shown in FIG. 12. The EB peptide was effective at inhibiting cell cytotoxicity as measured by lactate dehydrogenase release with an $IC_{50}$ value of 0.5 μM. The TAT-Cd peptide was not active against the H5 strain even at concentrations up to 100 μM.

Example 13

Protection of Mice from Lethal Infection with Influenza Virus Strain PR8 by Antiviral Peptides Mice were lightly anesthetized with 3% halothane and infected with strain PR8 by intranasal instillation of 50 microliters of virus in DME ($1 \times 10_5$ $TCID_{50}$ per mL.). Each group consisted of 20, 4-6 week old female BALB/C mice. The PBS group received vehicle (phosphate buffered saline) only. The PR8 group was infected with virus that had not been treated with peptide. The mice were checked twice daily and animals that were moribund (lying on cage bottom and not moving spontaneously) were euthanized and scored as positive for mortality.

As shown in FIG. 13, several of the peptides were able to protect the animals from Influenza virus infection. All of the mice infected with PR8 died from the infection. For the bKLA peptide, 80% of the mice were protected. The EB and EBX peptides protected 90% and 100% of the mice respectively. The TAT-C and $n_{51,51}$ peptide protected 90% of the mice while the less active TAT-$Cn_{50,51}$ peptide protected 90% of the mice. FIG. 14 shows that the bkLA peptide protects mice even when given after infection. Mice were infected with PR8 virus as noted above except the virus was not exposed to peptide for infection. The mice were then given a single dose of bkLA then at 6 hours post-infection, and again at 24 hours post-infection (0.5 mM bKLA). The data show that for bKLA post-infection, there was a delay in the onset of death and that on day 8 after infection, 40% of the mice were still alive. These results demonstrate that the peptides can protect mice from Influenza infection both prophylactically and even when given after infection. These results demonstrate that the peptides are active against Influenza virus in an animal model of infection.

Discussion of Examples 2-12

Examples 2-12 show that members of all 4 classes of membrane transiting peptides have antiviral activity against one or more viruses including HSV, Hi Influenza A, H5 Avian Influenza, and HIV in cell culture, and HSV and H1 Influenza A viruses in mouse models of infection.

The ability of the peptides to inhibit preadsorbed virus indicates that they act subsequent to viral attachment to cells. The inhibition of the preadsorbed virus was irreversible, or at least not fully reversible during the first 8 hours following rinsing of the cells to remove the peptide. In all of the assays, the inhibition of infection was independent of any cytotoxic effects of the peptides. The data also show, at least for some peptides, cytotoxicity is greater in serum free medium suggesting that one or more of the peptides bind serum components. The shift to higher $IC_{50}$ values for the antiviral activity for at least some peptides, also suggests that binding to serum components in the medium is occurring. This is most likely due to direct interactions of the peptides with serum proteins.

Many of the peptides that inactivated virions did so in a way, or ways, that are not readily reversible by dilution of the peptide or by dialysis (EB peptide). In addition, peptide exposure does not disrupt virion integrity, at least for the EB peptide (Bultmann et. al., J. Virol. 75, 2634-2645, 2001). Inactivation of virions was, however, not solely responsible for the antiviral effect since peptides that differ by 10-fold in their ability to inactivate virions inhibited infection at similar concentrations, even when not structurally related. Inactivation of virions was temperature dependent for some peptides but did not correlate with the effects of temperature on membrane transiting activities. These data show that viral inactivation, inhibition of infection, and membrane transiting activity are not always correlated.

Comparisons of the effects of sequence modifications demonstrated that for each of the four types of peptides, the presence of the membrane transiting motif was critical for the antiviral activity. All D-isoforms of at least some of the peptides (e.g. HOM derivatives) displayed antiviral activity regardless of whether they were unmodified, or modified by either biotinylation or acetylation. Thus antiviral activity does not appear to depend on chirality, at least for some peptides.

The data also show that membrane transiting derived peptides, or peptides derived from the MTP peptides inhibit Influenza A virus and Avian H5 Influenza virus infection in cell culture. The antiviral activities were apparent in the absence of toxicity as measured by trypan blue staining. For many of the peptides, many of the features noted above for HSV-1 were retained with Influenza including the ability to modify the activity of the peptide through structural modifications.

Finally, the data show that the peptides can inhibit infection with both HSV-1 and Influenza A virus in widely accepted and used mouse models of infection. For HSV-1, this was reflected in the reduction in severity of HSV induced keratitis following ocular infection and for Influenza A virus by both protection from lethal infection and by reducing or preventing the weight loss associated with the infection. Although not shown, the peptides also significantly reduced the titer of infectious virus in the eyes and the lungs of the infected mice indicating an antiviral effect is occurring in vivo.

In summary, the examples above demonstrate the utility of these peptides as antivirals in both cell culture and relevant animal models. They show that members of each of 4 classes of membrane transiting peptides have activity and that the activity can be modified through structural changes. The inhibition of infection appears to be primarily that of blocking entry of virus into cells but at higher concentrations, some or all of the peptides also inactivate virus particles. For the majority of the peptides, the inactivation is irreversible by dilution suggesting permanent inactivation has occurred. The availability of broad spectrum agents that prevent viral infection of cells would present a substantial advantage in therapy, particularly for viruses that cause persistent infections.

II. Modification of Activity by Structural Change in Peptides

Example 13

Inhibition of Entry and Virus Inactivation

Two assays were used to assess the ability of the TAT peptides to inhibit infection of Vero cells with the hrR3 virus. In both assays, the virus was preadsorbed to cells at 4° C. and entry was initiated in the presence of peptide by shifting the cultures to a permissive temperature (30-37° C.). One hour later, the peptide was rinsed off. The entry blocking activity was measured in half of the cultures, in which any extracellular virus remaining after the peptide treatment was inactivated with low pH citrate buffer. The rest of the cultures were exposed to PBS instead of citrate buffer and used to measure virus inactivation. Virus inactivation depended on persistent effects of the peptide lasting for a period of eight hours. At the end of that period, all cultures were fixed and infected cells were detected by staining with X-gal.

Figures 15A, 15B:
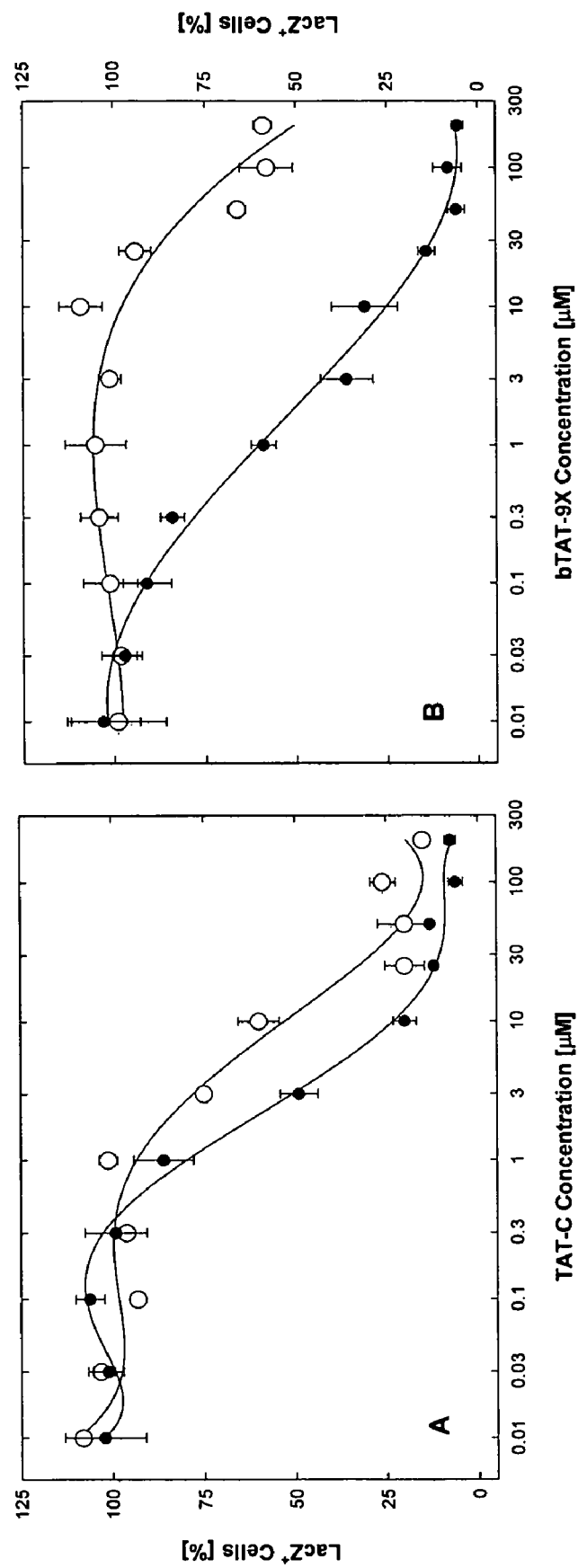

As shown in FIG. 15A, the TAT-C peptide consisting of the TAT-MTP with the addition of a single cysteine residue at its C-terminus, was not a selective entry blocker. That is, inhibition of entry (●; $IC_{50}$=3 μM) and virus inactivation (○; $IC_{50}$=11 μM) occurred at widely overlapping peptide concentrations. In contrast, a modified bTAT-9 peptide, bTAT-9X, including a scrambled version of the peptide (Table 5 #2), was clearly a selective entry blocker inhibiting entry by nearly 90% (FIG. 15B: ●; $IC_{50}$=2 μM) in the absence of virus inactivation (FIG. 15B: ○; $IC_{50}$=200 μM). The bTAT-9X peptide thus blocked entry as efficiently as TAT-C, whereas virus inactivation required approximately 20-times higher peptide concentrations. The third peptide, a modified TAT-C peptide with norleucine residues replacing K50 and K51 ($n_{50,51}$TAT-C), was a selective entry blocker at 31° C. (FIG. 15C) but not at 37° C. (FIG. 15D). That is, entry was efficiently blocked at 31° C. (FIG. 15C: ●; $IC_{50}$=1.3 μM) but not at 37° C. (FIG. 15D: ●; $IC_{50}$=48 μM), whereas virus inactivation was ineffective at both temperatures ($IC_{50}$s>200 μM). The inhibitory effects ($IC_{50}$s) of these and additional TAT-peptides are summarized in Tables 4 and 5. The fact that changes in temperature differentially affected entry blocking activities and that different TAT peptides differentially interfere with virus inactivation suggests that two independent processes are inhibited and seems to rule out the possibility that inhibition of entry is merely a consequence of virus inactivation.

TABLE 4

| Peptide | Entry Block | | Inactivation of Pre-Adsorbed Virus | | Inactivation of Virions |
|---|---|---|---|---|---|
| | 33° C. | 37° C. | 33° C. | 37° C. | 37° C. |
| TAT-C | 3 | 3.1 | 11 | 5.2 | 100 |
| $n_{50,51}$TAT-C | 5.9 | 41 | 215 | 210 | >600 |
| $n_{55,56}$TAT-C | 37 | 49 | 240 | 160 | >600 |
| TAT-Cd | 1.5 | 2.5 | 7.3 | 9.5 | 150 |
| $n_{55,56}$TAT-Cd | 3.9 | 5.3 | 16 | 13 | 250 |
| bTAT-9 | 2.1 | 5.4 | 110 | 53 | ~600 |
| bTAT-9X | 2 | 8.7 | 200 | 63 | >1200 |

Entry blocking activity and inactivation pre-adsorbed virus were measured as shown in FIG. 15. Inactivation of virions in solution was measured as described herein. All activities are expressed as micromolar $IC_{50}$s. Data for bTAT-9 are from Bultmann, H., and Brandt, C. R. (2002) J. Biol. Chem. 277, 36108-36023. Three of the peptides, $n_{50,51}$TAT-C, bTAT-9, and bTAT-9X, were selective entry blockers inhibiting entry at 33° C.>30-times as efficiently as they inhibited pre-adsorbed virus; the other peptides blocked entry <10-times as efficiently.

Virus (m.o.i.=0.025) was preadsorbed to Vero cells for 1 h at 4° C. before cultures were exposed to TAT-C (FIG. 15A), bTAT-9X (FIG. 15B), or $n_{50,51}$TAT-C (FIGS. 15C, 15D) for 1 h at 33 (FIGS. 15A, 15B), 31 (FIG. 15C), or 37° C. (FIG. 15D). Peptides were rinsed off and cultures were treated with either citrate buffer (pH 3) or PBS (pH 7.4) before they were returned to regular medium and stained with X-gal 8 h later. Inhibition of entry was measured in the citrate-treated cultures, in which any remaining external virus was inactivated immediately following exposure to peptide (●). Persistent virus inactivation lasting, at least in part, for the 8 h period following exposure to peptide, was measured in the PBS-treated cultures (○). The $IC_{50}$s measured in these experiments are included in Table 5.

Example 14

Post-entry and Cytotoxic Effects of Peptides

All of the peptides were also tested for possible post-entry and cytotoxic effects. Post-entry effects were measured in infected cultures, in which peptide was added immediately after the citrate treatments and kept in the medium throughout the following 8 h incubation period. Post-entry effects were seen with only four of the peptides: b12TAT-C ($IC_{50}$=100 μM), b6TAT-C ($IC_{50}$=190 μM), bTAT-C ($IC_{50}$=175 μM) and bTAT-9 ($IC_{50}$=210 μM). None of these, nor any of the other TAT peptides had any post-entry effects at concentrations inhibiting entry or at concentrations inactivating virus by ≧50%. Only in case of the bTAT-9 peptide was there some overlap in concentrations with post-entry effects and concentrations that inactivated virus. These findings rule out the possibility that any of the TAT peptides (with the possible exception of bTAT-9) directly interfered with the expression and activity of β-galactosidase during inhibition of entry and during virus inactivation.

Cytotoxic effects were measured in mock-infected cultures treated with peptide for 1 h and exposed to PBS rather than citrate buffer and stained with trypan blue rather than X-gal. The most cytotoxic peptides were those with twelve or more additional amino acids attached to the TAT-MTP (see below: Table 5 #3-6). These peptides (bTAT-17, TAT-17, b1TAT-C and b12TAT-C) displayed cytotoxicity at $IC_{50}$s of approximately 200 μM. For all other peptides the $IC_{50}$s for cytotoxicity were >300 μM. In no case was entry blocking activity or virus inactivation limited by cytotoxic effects.

Example 15

Temperature Effects

Figures 16A, 16B:
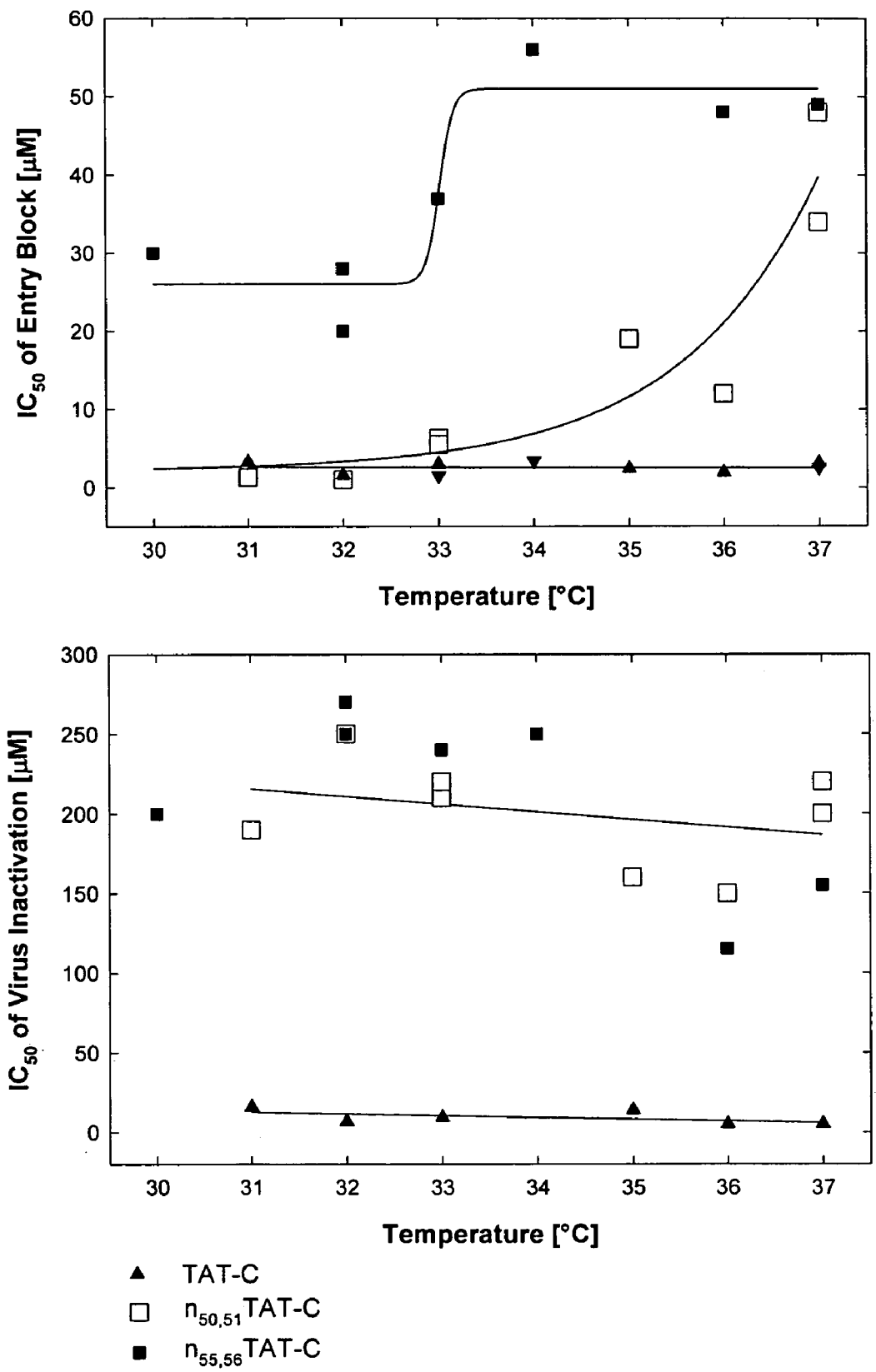

The temperature effects noted above were further investigated for three different TAT peptides (FIG. 16). Entry blocking activity (Panel A) and virus inactivation (Panel B) were measured as described in the legend to FIG. 15. $IC_{50}$s (in μM) were measured after treating pre-adsorbed virus at various temperatures with TAT-C (▲) or the two norleucine-substituted peptides $n_{50,51}$TAT-C(○) and $n_{55,56}$TAT-C(○). These studies confirmed that the inhibition of entry by the $n_{50,51}$TAT-C peptide was strongly temperature-dependent and was decreased 50-fold between 31 and 37° C. as reflected in the approximate 50-fold increase in $IC_{50}$s (FIG. 16A: ○) whereas virus inactivation remained invariant with $IC_{50}$s scattered around 200 μM (FIG. 16B: ○). In contrast, both, inhibition of entry and virus inactivation by TAT-C, were completely temperature-independent (FIGS. 16A, B: ▲). This demonstrated that substitution of $K_{50}$ and $K_{51}$ by norleucine residues specifically and selectively limited entry-blocking activity in a temperature-dependent manner. Alternative norleucine substitutions at $R_{55}$ and $R_{56}$ in the TAT-C peptide ($n_{55,56}$TAT-C) also limited entry blocking activity (FIG. 16A: ●) in addition to limiting virus inactivation (FIG. 16B: ●). Entry-blocking activity of the $n_{55,56}$TAT-C peptide was curtailed both above and below 330, but the effect was less severe at the lower temperatures. Temperature changes also affected antiviral activities of the bTAT-9 and bTAT-9X peptides. When the temperature was increased from 33 to 37° C., these peptides lost at least half of their entry-blocking activity but became more efficient in the inactivation of virus (Table 5). The non-coordinate effects of temperature confirmed that inhibition of entry and virus inactivation depend on separate processes.

Example 16

Reversibility of Antiviral Effects

Figure 17:
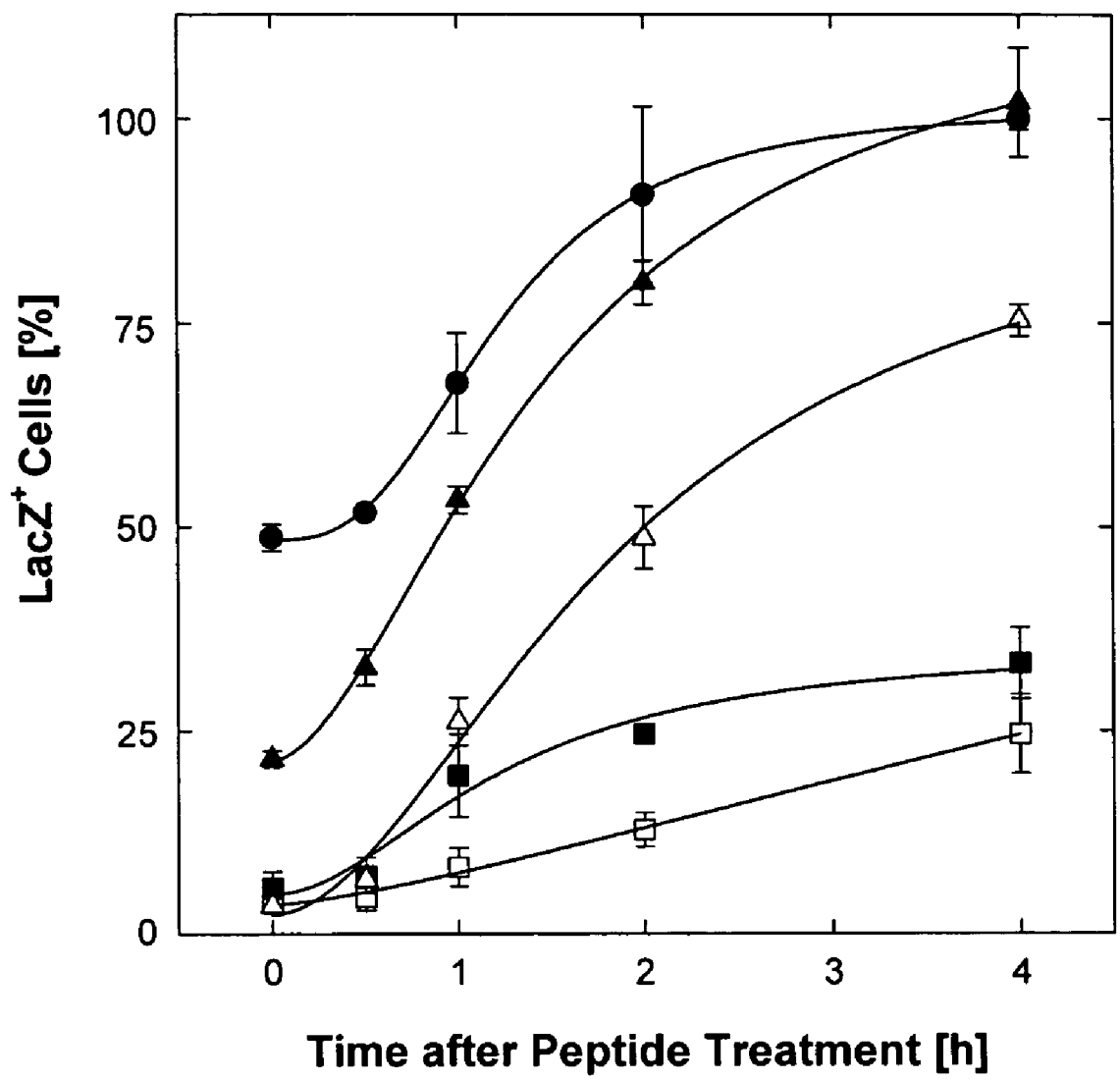

Virus (m.o.i.=0.028) was pre-adsorbed to Vero cells for 1 h at 4° C. and exposed to TAT-C (■: 10 μM; □: 100 μM) or $n_{50,51}$TAT-C (▲: 10 μM; ∆: 100 μM) for 1 h at 32° C. Controls (●) were incubated without peptide. The results of this example are shown in FIG. 17. Peptides were rinsed off and cultures were switched to 37° C. At the indicated times following the temperature switch, any remaining external virus was inactivated with low pH citrate buffer and cultures were returned to regular medium at 37° C. and stained with X-gal 8 h later. The number of LacZ+ cells counted in control wells (195/mm$^2$) was set to 100%.

The conclusion that the peptides can affect two different processes was independently supported by the finding that the inhibitory effects of peptides that primarily act as entry blockers were largely or completely reversible whereas the inhibitory effects of peptides with less selective effects were not. This was shown in experiments, in which virus entry was allowed to proceed in a two-step fashion for 1 h at 32° C. and for up to 4 h at 37° C. Entry at 37° C. was followed by treating cultures at various times with low pH citrate buffer to inactivate any remaining extracellular virus (FIG. 17). Peptides were present only during the first hour at 32° C. Without addition of peptide, approximately 50% of the virus entered cells at 32° C. (0-time), the rest entered subsequently at 37° C. (●). In the presence of 10 μM $n_{50,51}$TAT-C, entry at 32° C. was blocked by about 60% and only approximately 20% of the virus was internalized. The inhibitory effect at this low peptide concentration was fully reversible, since all of the remaining virus entered cells at 37° C. after removal of peptide (▲). At 10-fold higher concentrations of $n_{50,51}$TAT-C, entry at 32° C. was inhibited by about 90% and 75% of the virus eventually entered cells (∆). In contrast, the inhibitory effects of 10 or 100 μM TAT-C (~90% after 1 h at 32° C.) were largely irreversible allowing only 25-33% of the virus to become internalized after the cultures were rinsed and shifted to 37° C. (■ and □, respectively). Given that overlapping peptide concentrations were required for blocking entry and for virus inactivation (cf. FIG. 15), these data suggest that inhibition of entry was fully reversible whereas virus inactivation was irreversible.

Example 17

Effects of D-isomers

Since it had previously been shown that antiviral activities, like membrane-transiting activities of the HOM-MTP, did not depend on chirality, the antiviral effects of TAT peptides composed of D-isomers was also examined. By all criteria, the TAT-Cd peptide was as effective an antiviral agent as the TAT-C peptide (Table 4) but surprisingly, its effects seemed to lack the same sequence specificity. That is, a TAT-Cd peptide in which D-$R_{55}$ and D-$R_{56}$ were replaced by D-norleucine ($n_{55,56}$TAT-Cd), only lost about half the antiviral activity, whereas the similarly substituted TAT-C peptide ($n_{55,56}$TAT-C) lost >90% of its activity (Table 4). The antiviral activity of the $n_{55,56}$TAT-Cd peptide thus far exceeded the residual activity of the $n_{55,56}$TAT-C peptide indicating that chirality was not irrelevant even though no stereochemical differences in activity could be detected between the non-substituted peptides.

Example 18

Effects of Peptide Extensions

The presence of the peptide extensions in the bTAT-9 and bTAT-9X peptides did not substantially limit entry-blocking activities but clearly limited virus inactivation (FIG. 15B; Tables 4 & 5). Thus, the peptides did not behave like inert cargo but mimicked one of the effects of L-norleucine substitutions within the TAT-MTP. The fact that the native peptide and the scrambled version of this peptide acted similarly (Table 4) suggested that unrelated peptides may have similar effects. Alternatively, different peptides might modify antiviral activities of the TAT-MTP in novel ways. These possibilities were examined by replacing the peptides with a scrambled version of the membrane-transiting h-region of the FGF4 signal peptide previously incorporated into the EBX peptide (6). The antiviral activities of the resulting peptide (bTAT-17; Table 5 #3) closely matched those of the TAT-C peptide (Table 5 #10) rather than those of the bTAT-9 or bTAT-9X peptides (Table 5 # 1, 2). Truncation of the biotinylated Y47 present in bTAT-17 as in bTAT-9 and bTAT-9X, had no effect (TAT-17; Table 5 #4). A second set of peptides was synthesized carrying only the biotin-ε-aminohexanoyl group or progressively longer biotinylated segments of the scrambled h-region at the N-terminal side of the TAT-MTP (Table 5 #5-8). Again, the antiviral activities of all these peptides differed little from those of the TAT-C peptide. Thus none of the peptide additions derived from the scramble sequence of the h-region regardless of their lengths and regardless of their placement at the N- or C-terminus, had any substantial effect on the antiviral activities of the TAT-MTP. This emphasized that modification of antiviral activities of the TAT-MTP requires some specific but not strictly sequence-dependent feature(s) in peptide extensions.

TABLE 5

(SEQ ID NOS: 10, 11, 30-38, respectively, in order of appearance.)

| Peptide | Sequence* | Purity (%) | Entry Block | Virus Inactivation |
|---|---|---|---|---|
| bTAT-9 | $^b$-Y GRKKRRQRRRPGYAGAVVNDL$^{COOH}$ | 79 | 2.1 | 110 |
| bTAT-9X | $^b$-Y GRKKRRQRRRPGDVYANGLVA$^{COOH}$ | 90 | 2.0 | 200 |
| TAT-17 | $^{NH2}$GRKKRRQRRRPLAALPLVLAAPLAVLA$^{COOH}$ | 84 | 2.4 | 8.3 |
| bTAT-17 | $^b$-Y GRKKRRQRRRPLAALPLVLAAPLAVLA$^{COOH}$ | 99 | 2.4 | 6.6 |
| b17TAT-C | $^b$-LAALPLVLAAPLAVLAPGRKKRRQRRR -C$^{amide}$ | 92 | 5.4 | 9.4 |
| b12TAT-C | $^b$-LVLAAPLAVLAPGRKKRRQRRRC$^{amide}$ | 63 | 3.3 | 11 |

TABLE 5-continued (SEQ ID NOS: 10, 11, 30-38, respectively, in order of appearance.)

| Peptide | Sequence* | Purity (%) | Entry Block | Virus In-activation |
|---|---|---|---|---|
| b6TAT-C | $^{b-}$LAVLAPGRKKRRQRRRC$^{amide}$ | 70 | 5.3 | 25 |
| bTAT-C | $^{b-}$GRKKRRQRRRC$^{amide}$ | 91 | 5.8 | 27 |
| TAT$^-$ | $^{NH2}$GRKKRRQRRR$^{COOH}$ | 95 | 6.6 | ≧150† |
| TAT$^0$ | $^{NH2}$GRKKRRQRRR$^{amide}$ | 96 | 0.9 | >300† |
| TAT-C | $^{NH2}$GRKKRRQRRRC$^{COOH}$ | 97 | 3.0 | 11 |

*$^{b-}$ = biotin-ε-aminohexanoyl.

Figure 18:
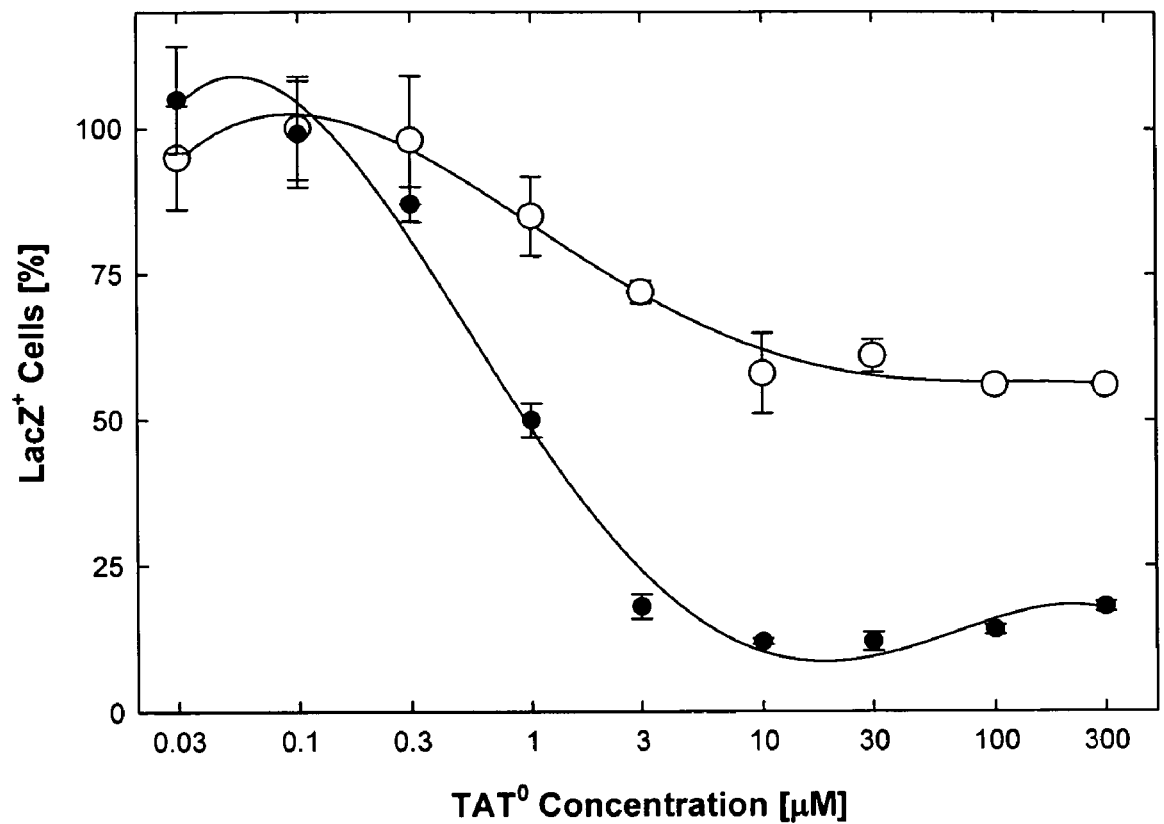

Entry blocking activity and inactivation of pre-adsorbed virus were measured at 33° C. as shown in FIG. 18 and are expressed as micromolar $IC_{50}$s. The $IC_{50}$s of virus inactivation by TAT$^-$ and TAT$^0$ (†) are poorly defined, since virus was only partially inhibited (cf. FIG. 17). The better defined doses required for 25% virus inactivation were 10 μM and 2 μM, respectively, for TAT$^-$ and TAT$^0$.

Interestingly, the single cysteine residue, which was added to the C-terminus of the TAT-MTP as a potential conjugation site, appears to be important for antiviral activity. This was examined by testing two truncated peptides terminating either with arginine (TAT; Table 5 #9) or arginine amide (TAT$^0$; Table 5 #10) in position 57 of the TAT-MTP. Both of these peptides were distinguished from all other TAT peptides in that there was clear evidence that virus could only be partially inactivated by about 50%. For the TAT$^0$ peptide, virus inactivation reached a plateau (42% inhibition) at peptide concentrations between 10 and 300 μM (FIG. 18). In FIG. 18, inhibition of entry ($IC_{50}$=0.9 μM) and virus inactivation (25% inactivation: $IC_{25}$=2 μM) were measured at 33° C. as described in the legend to FIG. 15. In case of the TAT$^-$ peptide, a slightly lower plateau (46% inhibition) was reached at concentrations between 30 and 300 μM (not shown). Virus inactivation by the TAT-C peptide also seemed to reach a plateau at concentrations between 25 and 200 μM but only after about 80% of the virus was inhibited (FIG. 15A). The additional cysteine at the carboxy-terminus thus clearly enhanced the antiviral activity of the TAT-MTP.

Despite their limited ability to inactivate virus, TAT$^-$ and TAT$^0$ could block entry by ≧90% (as shown for TAT$^0$ in FIG. 18) indicating, again, that inhibition of entry was not simply the result of virus inactivation. Nevertheless, TAT$^-$ and TAT$^0$, unlike bTAT-9, bTAT-9X and $n_{50,51}$TAT-C, were not selective entry blockers, because their entry blocking activities ($IC_{50}$=6.6 μM and 0.9 μM, respectively; Table 5) widely overlapped with partial virus inactivation ($IC_{25}$=10 μM and 2 μM, respectively; Table 5 and FIG. 18). The fact that TAT$^0$ was inhibitory at 5-7 times lower concentrations than TAT$^-$ suggests that some charge interference by the proximal carboxyl group in TAT$^-$ may be limiting.

Example 19

Release of Adsorbed Virions

Figures 19A, 19B:
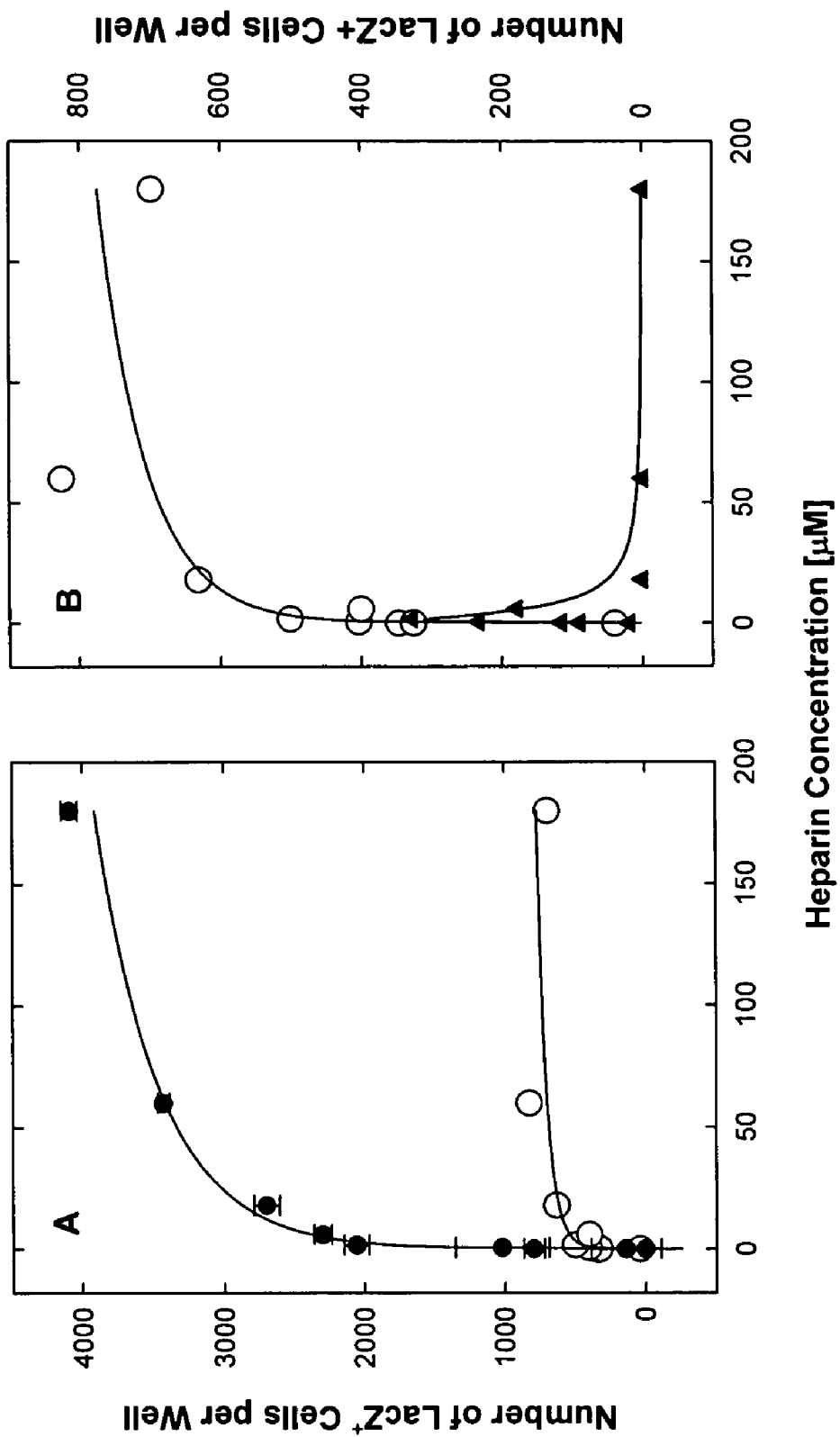
Figure 21:
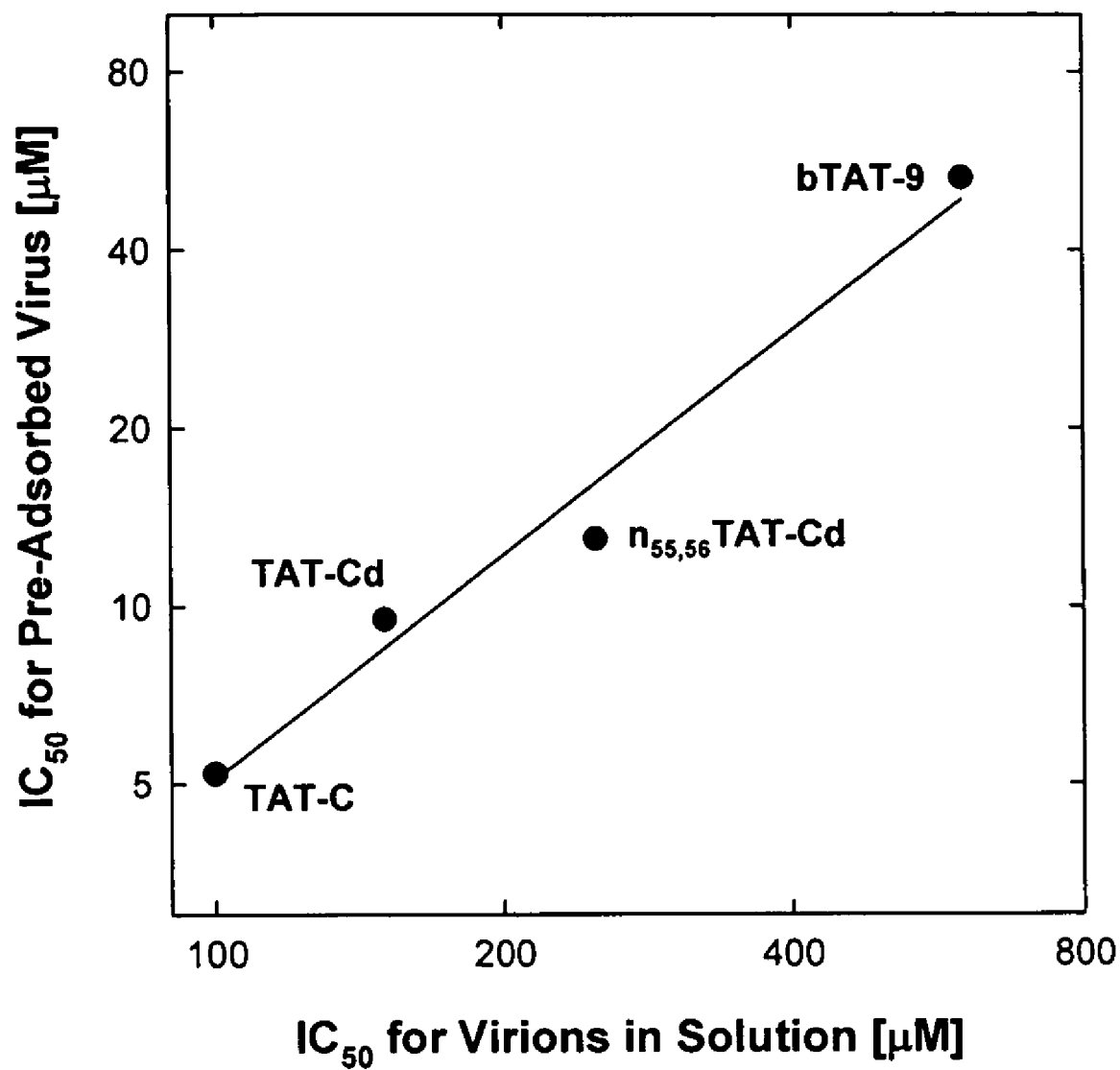

Since TAT-peptides are expected to bind to heparan sulfate and could potentially compete with virus attachment to cells, the possibility that the inhibition of preadsorbed virus may be due to the release of virions into the culture medium was examined. Initial experiments were done with heparin, which had been shown to compete with HSV attachment. As shown in FIG. 19A, heparin maximally inhibited 94% of the preadsorbed virus during a 1 h treatment at 4° C. potentially causing enough virus to be released to infect 4100 cells/well (●). Yet only 15% of the maximal number of virions expected to be released could actually be recovered in the medium (○) suggesting that 85% of the inactivated virus remained adsorbed to cells. After treatments with low heparin concentrations, some infectious virus could be recovered without addition of NaCl to the medium (FIG. 19B: ▲). The fact that more infectious virus could be recovered following treatment with NaCl (FIG. 19B: ○) suggests that heparin remained bound to the released virions. Control experiments with virions in solution established that 0.5 M NaCl had no effect on infectivity (see below: FIG. 21).

In this example pre-adsorbed virus was exposed to heparin (FIG. 19 Panels A, B) or TAT-Cd peptide (FIG. 19 Panels C, D) for 1 h at 4° C. (FIG. 19 Panels A, B, C) or 18° C. (FIG. 19 Panel D) and any virus released into the culture medium during this time was collected and pelleted in the presence (○) or absence (▲) of 0.5 M NaCl and assayed for infectivity as described in Example 1. To measure the infectivity of the virus that remained attached to cells, cultures were returned to regular medium and stained with X-gal 8 h later. Virus inhibition (●) corresponds to the number of LacZ+ cells seen in the absence of inhibitor minus the number of LacZ+ cells seen in the presence of inhibitor and is equivalent to the maximal amount of virus potentially released into the culture medium as a result of virus inhibition. Panel B compares the amount of infectious virus recovered in the presence (○; data from Panel A) and absence (▲) of 0.5 M NaCl at an expanded scale.

In similar experiments with the TAT-Cd peptide, preadsorbed virus was inhibited by 92% (FIG. 19C: ●) but only 4.4% of the potentially released virus was actually recovered following a 1 h treatment at 4° C. (FIG. 19C: ○). Increasing the treatment temperature to 18° C. still blocked virus entry by >99% but had no effect on the release of virions (FIG. 19D: maximally 5.6% virus recovery (○) after inactivation of 93% of the virus (●)). Recovery of infectious virus released by TAT-Cd, was completely dependent on prior extraction of the peptide with 0.5 M NaCl (FIG. 19C, D: ▲). Inhibition of preadsorbed virus by TAT-Cd thus seems to occur essentially independent of any reversal of virus attachment. The fact that virus recovery was enhanced by salt extraction suggests that reversible ionic interactions between TAT peptides and virions may play some role in the antiviral effects.

Example 20

Inactivation of Virions

Figures 20A, 20B:
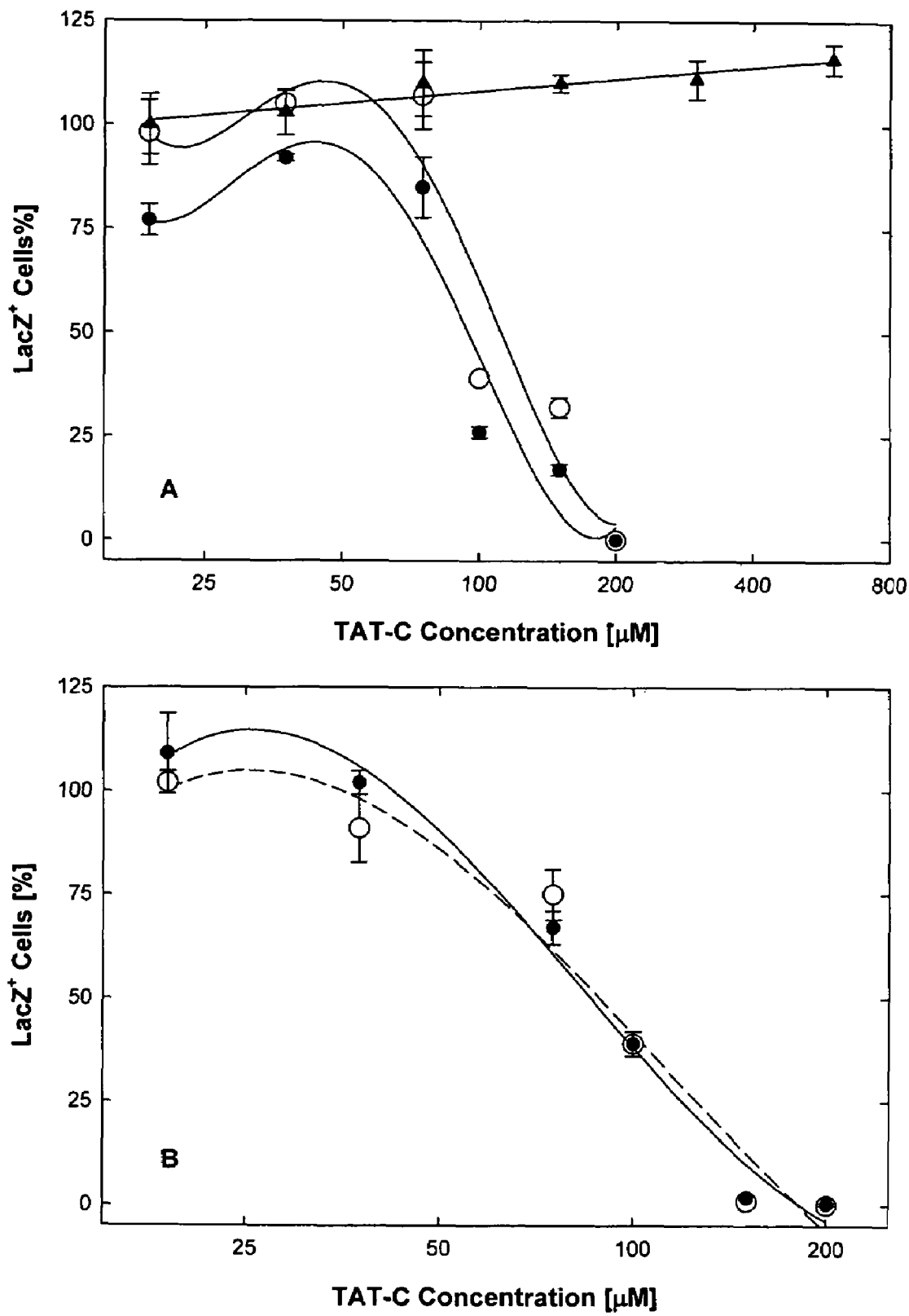

Previous studies had shown that bTAT-9 and bTAT9X did not inactivate virions in solution effectively ($IC_{50} \geq 600$ μM). In contrast, at 37° C., TAT-C inactivated virions with an $IC_{50}$ of about 75 μM, regardless whether the peptide was rendered ineffective by dilution or removed by centrifugation following treatments of the virus (FIG. 20A: ● and ○, respectively). Neither of the two norleucine-substituted peptides ($n_{50,51}$TAT-C and $n_{55,56}$TAT-C) had any effect on virions at concentrations up to 600 μM (Table 4). TAT-Cd was nearly as effective as TAT-C but $n_{55,56}$TAT-Cd was again more effective than $n_{55,56}$TAT-C (Table 4). Like TAT-C (FIG. 20A: ▲), none of these peptides had any ability to inactivate virions at 4° C.

Virus ($3 \times 10^6$ pfu/mL hrR3) was exposed to TAT-Cd in serum-free medium for 1 h at 4° C. (▲) or 37° C. (●,○) and infectivity was measured either after a 1000-fold dilution of aliquots into serum-supplemented medium (●,▲), or after pelleting the virus in serum-supplemented medium (○), as described in Example 1. For virus treated at 37° C., nearly the same $IC_{50}$s were obtained in the two assays [A: 96 μM (●) vs. 110 μM (○)]. In Panel B, the TAT-C-treated pelleted virus was resuspended in serum-free medium and exposed to 0.01% active [B (●): $IC_{50}$=86 μM] or inactivated trypsin [B (○): $IC_{50}$=90 μM] for 1 h at 37° C. before infectivity was measured (see above).

The inactivation of virions in solution was correlated with the inactivation of preadsorbed virus (last two columns in Table 4; FIG. 21) suggesting that inactivation of preadsorbed virus depends on direct interactions of peptides with virus particles. In FIG. 21, for the four identified peptides, inactivation of pre-adsorbed virus and inactivation of virions were measured at 37° C. as shown in FIG. 15 (○) and FIG. 20, respectively. The $IC_{50}$s are taken from the last two columns of Table 4. The fact that inactivation of virions in solution required about 20-times higher peptide concentrations, is presumably due to the different assay conditions, notably, the much higher virus concentration.

Example 21

Irreversibility of the Inactivation of Virions

In this example aliquots (10 μl) of mock-treated virions (gray bars in FIG. 22) and virions treated for 1 h at 37° C. with 200 μM TAT-Cd in serum-supplemented DMEM (black bars in FIG. 21) (both at $2.9 \times 10^6$ pfu/mL) were diluted into 1 mL peptide-free serum-supplemented medium without or with the addition of 0.5 M NaCl. Some of the virus diluted without the addition of NaCl was pelleted immediately (Control), while the rest of the diluted virus was stored at 4° C. and pelleted 19 h later. The virus was pelleted and assayed for infectivity as described in Example 1.

Figure 22:
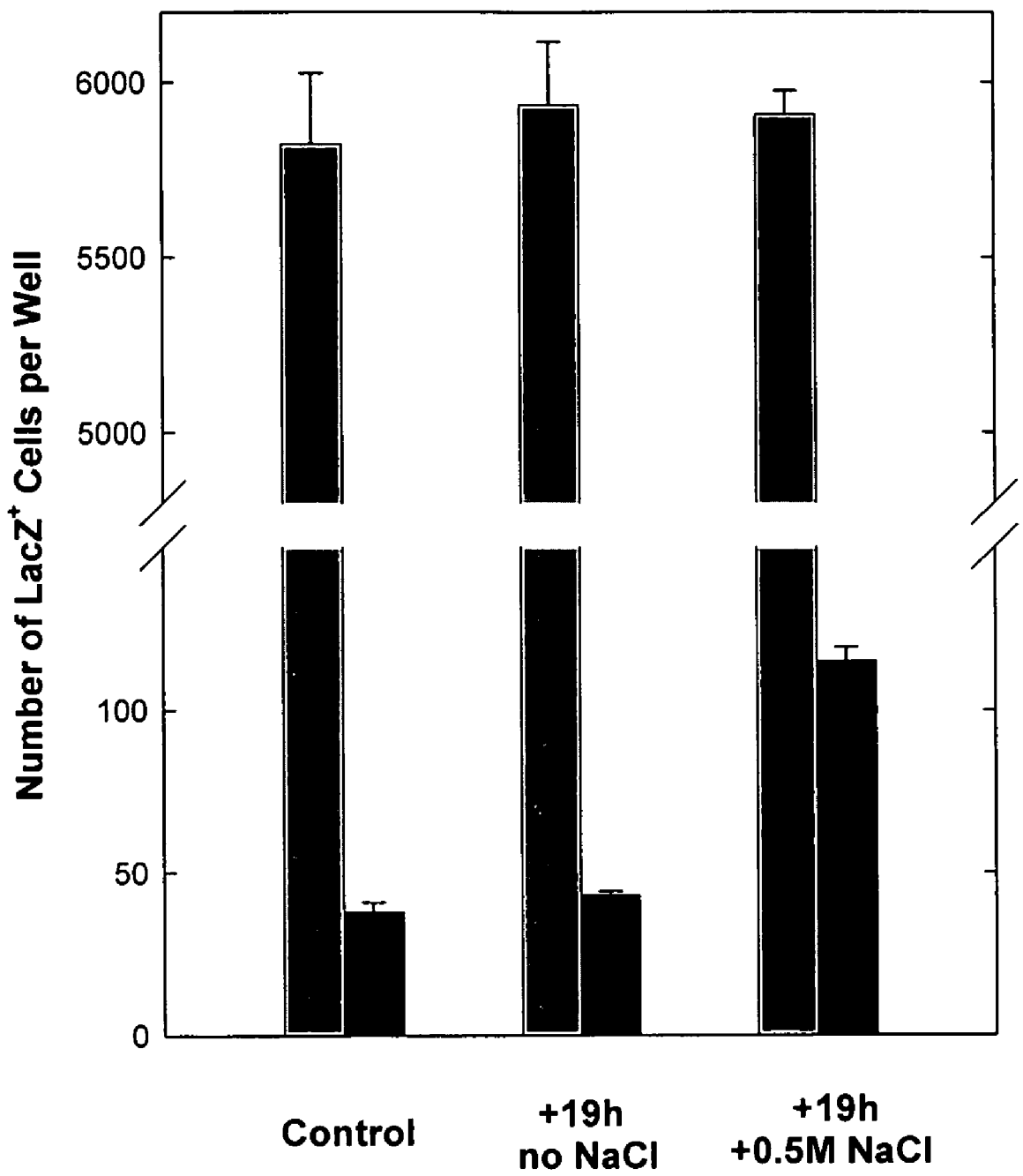

Inactivation of virions by TAT peptides appears to be irreversible. For example, immediately after treatments with TAT-Cd, recovery of infectious virions by centrifugation was reduced to <1% of the mock-treated virus (FIG. 22: black versus gray 'control' bar). No additional virus was recovered if the peptide was diluted and virions were incubated for 19 h at 4° C. prior to centrifugation (FIG. 22: center bars). The presence of 0.5 M NaCl during the 19 h incubation increased viral yields by only about 1% of the mock-treated controls indicating that the inactivation of virions by TAT-Cd was essentially irreversible even at high salt concentrations. Without prior peptide treatments, equivalent amounts of infectious virus were recovered under all conditions (FIG. 22: gray bars).

To examine the possibility that irreversible virus inactivation depended on irreversible peptide binding to virions, TAT-C treated virus recovered by centrifugation, was treated with trypsin, which inactivates the peptides. Such trypsin treatments had no effect on virus infectivity as compared to controls using trypsin inactivated by soybean trypsin inhibitor (FIG. 20B: ● and ○, respectively). Furthermore, the $IC_{50}$s measured after trypsinization or mock-trypsinization (FIG. 20B) were not substantially different from $IC_{50}$s measured in other ways (FIG. 20A).

Figures 23A, 23B:
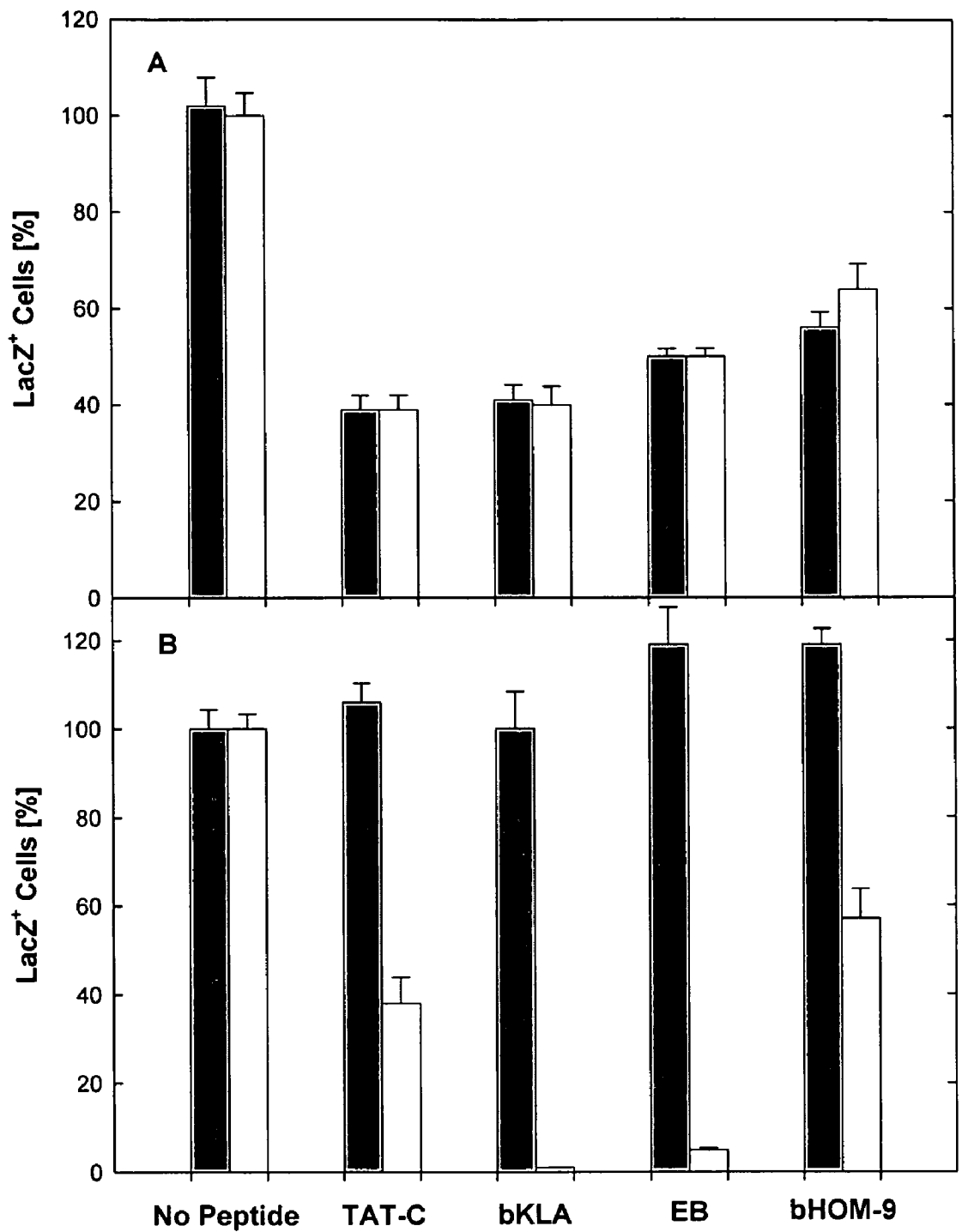

Trypsin also did not have any effect on the infectivity of virions partially inactivated by peptides representing three other structurally unrelated types of membrane-transiting peptides with antiviral activity: bKLA, EB and bHOM-9 (FIG. 23A). Trypsinization of the peptides, including TAT-C, prior to exposure to virions completely abolished their antiviral activity, indicating they are sensitive to trypsin digestion (FIG. 23B). Complete inactivation of the TAT-C peptide required twice the trypsin concentration necessary for the complete inactivation of more than equal molar amounts of EB or bHOM-9, even though the TAT-C peptide contains a proportionally larger number or arginine and lysine residues (8/11 versus 4/20 and 7/28, respectively). Higher trypsin concentrations (0.01% or ~4 μM) had no effect on the infectivity of control virions that had not been pretreated with peptide (FIG. 23: 'no peptide'). As expected, trypsinization also had no effect on antiviral activity of the TAT-Cd peptide. Treatments with a 1.3-fold molar excess of soybean trypsin inhibitor completely abolished trypsin activity (data not shown). These results seem to exclude the possibility that irreversible inactivation of virions by any of the membrane-transiting peptides depends on continued binding of trypsin-accessible peptides to the virions.

In Panel A of FIG. 23, virions ($4 \times 10^6$ pfu/mL hrR3) were exposed to peptides in serum-free medium for 1 h at 37° C., pelleted in peptide-free serum-supplemented medium, resuspended in serum-free medium, exposed to active trypsin (shaded bars) or inactive trypsin (open bars) for 1 h at 37° C., and assayed for remaining infectivity as described in Example I. Peptide concentrations were chosen to result in ~50% virus inactivation in controls (open bars): 100 μM TAT-C, 12.5 μM bKLA, 50 μM EB, and 200 μM bHOM-9. In Panel B, peptides in serum-free medium were pre-treated with active trypsin (open bars) or inactivated trypsin (shaded bars) for 1 h at 37° C. before they were added to virions for 1 h at 37° C. (see Example 1). The treated virions were then pelleted and resuspended in serum-supplemented medium and assayed for infectivity without further trypsinization. The peptide concentrations were as high or higher than those used in Panel A: 150 M TAT-C, 50 μM bKLA, 200 μM EB and bHOM-9. Trypsin concentrations used in both Panels A and B, were 0.005% (for bKLA, EB and bHOM-9) or 0.01% (for TAT-C and the 'no peptide' control).

Discussion of Examples 10-21

The above examples demonstrate that various peptides containing the TAT-MTP can block entry of HSV-I virus in cultured Vero cells by two independent mechanisms: (a) by direct interactions with virions resulting in irreversible virus inactivation and (b) by some still undefined readily reversible mechanism(s), which may not exclusively involve interactions with virions. It was possible to distinguish indirect effects on entry such as 'virus inactivation' from more narrowly defined 'entry blocking activities' of peptides (cf. FIG. 15) on the basis of four different observations. Firstly, some peptides, notably those acting as selective entry blockers, lost much of the ability to inactivate virions while retaining most or all other entry blocking activity. Secondly, in other peptides, entry blocking activity was rendered temperature-dependent whereas virus inactivation was not. Thirdly, inhibition of virus infection by selective entry blockers was largely or entirely reversible while virus inactivation was not. Finally, direct and irreversible inactivation of virions in solution was correlated with 'virus inactivation' but not with 'entry blocking activity' (Table 4; FIG. 21). These findings exclude the possibility that inhibition of entry is merely the result of irreversible virus inactivation for some peptides.

Data generated using TAT peptide variants show that the antiviral activity can be modified. Three different means of modifying these functions have been defined: 1) by adding a C-terminal cysteine residue, 2) by replacing the cysteine with specific short peptides, and 3) by replacing positively charged residues within the TAT-MTP with norleucine.

The TAT-MTP, by itself, inactivated virus by no more than 50%. Addition of a C-terminal cysteine or cysteine amide improved the efficacy of virus inactivation increasing it to 80% (TAT-C) or nearly 100% (TAT-Cd). Replacing the cysteine with the RR2-derived peptide or a scrambled version of that peptide selectively curtailed virus inactivation. Other added peptides, however, were functionally 'inert' and had little or no effect on antiviral activity indicating that some specific but not strictly sequence-dependent feature or features of the peptide extensions are important in modifying TAT-MTP functions. The same peptide also modified the antiviral activity of the HOM-MTP but, it enhanced rather than curtailed virus inactivation (Bultmann, H., and Brandt, C. R. (2002) J. Biol. Chem. 277, 36108-36023).

Replacing pairs of lysines (residues 50 and 51) or arginines (residues 55 and 56) within the TAT-MTP not only curtailed virus inactivation but was the only means of interfering with entry blocking activity in any substantial way. The loss of function in the $n_{50,51}$TAT-C peptide is consistent with the finding that selective acetylation of lysines 50 and 51 in the bTAT-9 peptide inhibited antiviral activity. The loss of entry blocking activity in the $n_{50,51}$TAT-C peptide was conditional and was expressed only at temperatures ($\geqq34°$ C.) that could promote virus entry at near-maximal rates. The loss of antiviral activity in the $n_{55,56}$TAT-C peptide correlates with the finding that arginines 55-57 are important for membrane-transiting activity (Vivès, et al. (1997b) Lett. Pept. Sci. 4, 429-436). However, antiviral and membrane-transiting activities are not always correlated. For example, inactivation of virions in solution by the TAT-C peptide (or other peptides) was abolished at 4° C. (FIG. 18A: A), whereas previous work had shown that membrane-transiting activity was retained at 4° C. (10). Norleucine substitutions in positions 55 and 56 of the TAT-MTP had very different effects depending on whether the peptide was composed of L- or D-isomers (Table 4). As indicated above, this implies that chirality may play some, as yet undefined, role in the antiviral activity of TAT peptides.

While there is ample evidence that virus entry can be blocked independent of virus inactivation, there were no indications that any of the TAT peptides or any of the other antiviral peptides with membrane-transiting properties inactivated virus without inhibiting entry. Peptide concentrations required for virus inactivation invariably exceeded peptide concentrations inhibiting entry. This suggests that both, inhibition of entry and virus inactivation, may depend on direct interactions of peptides with virions and that virus inactivation merely requires higher peptide concentrations. More specifically, one might assume that any inhibition of entry independent of virus inactivation relies on reversible peptide binding to virions, whereas virus inactivation depends on secondary effects of high peptide concentrations that leave virions irreversibly inactivated even after the peptide was removed.

Reversible ionic interactions between TAT peptides and virions may indeed contribute to blocking infections. The small amount (~5%) of adsorbed virus that could be released into the culture medium by the TAT-Cd peptide was infectious only if the peptide was removed with 0.5 M NaCl (FIGS. 19C, 19D). Also, a small fraction (~1%) of virions treated with high concentrations of TAT-Cd peptide could be reactivated only after extraction with 0.5 M NaCl (FIG. 22). The notion that irreversible virus inactivation depends on secondary effects of peptides is compatible with the finding that virions exposed to high peptide concentrations could not be reactivated by trypsinization (FIG. 20B; FIG. 23). Trypsinization also failed to reactivate virions treated with bKLA, EB or bHOM-9 representing three other groups of antiviral peptides with membrane-transiting properties (FIG. 23). Thus, irreversible virus inactivation does not depend on any of these peptides remaining bound to virions in a trypsin-accessible manner.

Antiviral effects of the TAT peptides appear to be largely independent of any reversal of virus adsorption as indicated by the fact that maximally only about 5% of infectious preadsorbed virus could be recovered in the culture medium after treatments with the TAT-Cd peptide as compared to 15% being released by heparin (FIG. 19). Heparin had earlier been shown to release up to 60% of preadsorbed HSV-1 KOS virions from HEp-2 cells (Herold, et al. (1994) J. Gen. Virol. 75, 1211-1222).

In conclusion, the results described herein are compatible with the simple notion that all antiviral activities of TAT peptides depend exclusively on reversible and irreversible interactions with virions. It was found, however, that some of the TAT peptides and some of the other antiviral peptides with membrane-transiting properties can also block virus entry by activating cellular responses independent of any effects on virions. The inventors have shown that these antiviral peptides are remarkably flexible antivirals whose various activities can be manipulated by specific structural additions and modifications.

III. Peptide Induction of Cellular Resistance to Virus Infection

Example 22

Effect of Cell Pretreatments with TAT-Cd or EB on Subsequent Viral Infection in the Absence or Presence of Peptide Confluent Vero cell cultures ($2\times10^5$ cells/well) were exposed to TAT-Cd (A) or EB (C) for 1 h at 37° C. The peptides were rinsed off and cultures were infected in the absence of peptide with untreated virus (4500 pfu/well hrR3) for 1 h at 37° C. Any remaining external virus was inactivated with citrate buffer (pH 3) and cells were incubated for 8 h before staining with X-gal (▲) or trypan blue (Δ). Alternatively, cells pretreated with peptides (•) along with non-pretreated control cultures (○) were infected in the presence of peptide with virus that had been pretreated with peptide for 1 h at 37° C. immediately before infection. Again, either TAT-Cd (B) or EB (D) was used in these experiments. Following infection, the peptides were rinsed off, external virus was inactivated with citrate, and cultures were stained with X-gal 8 h later. All experiments were done in Hepes-buffered serum-supplemented DMEM.

Figures 24A, 24B:
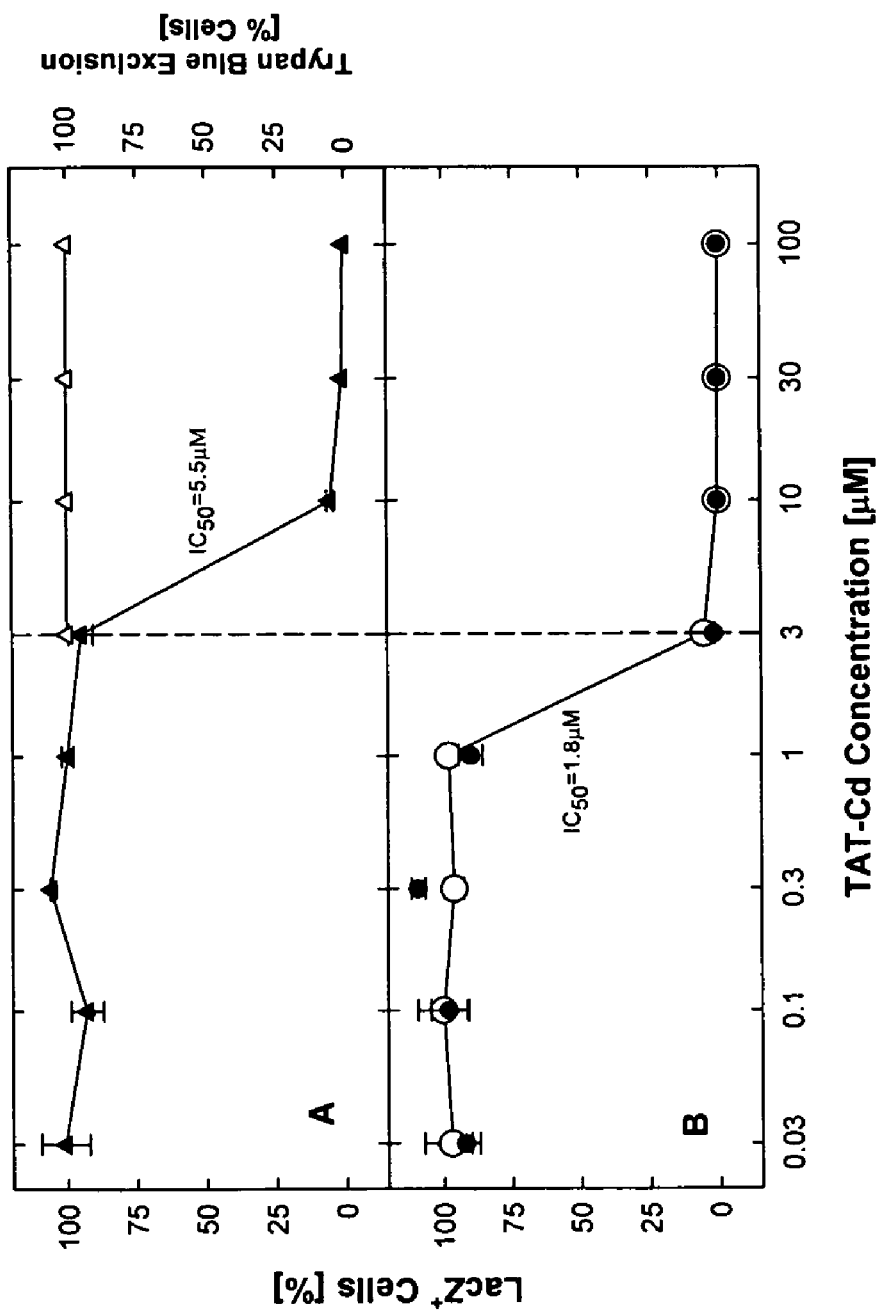

The results for this Example are shown in FIG. 24, which illustrates the following:

Low concentrations of TAT-Cd ($IC_{50}$=5.5 µM) or EB ($IC_{50}$=2.3 µM) render cells resistant to subsequent viral infection in the absence of peptide (A, C: ▲);

Induction of resistance is not associated with any cytotoxic effects (trypan blue exclusion; A, C: Δ); and Cell pretreatments add little (D: shift of $IC_{50}$ from 1.7 to 0.9 µM EB) or no (B: $IC_{50}$=1.8 µM TAT-Cd) antiviral activity, if peptides are included during infection with peptide treated virions.

Example 23

Rapidity of Induction of Cellular Resistance to Viral Infection

Confluent Vero cell cultures plated in strip wells ($2\times10^5$ cells/well) were exposed to 30 µM TAT-C (Δ), TAT-Cd (▲), EBX (○), EB (•) or no peptide (□) at 37° C. for the times indicated. The peptides were then rinsed off and cells were infected with untreated virus (8400 pfu/well hrR3) for 1 h at 37° C., treated with low-pH citrate buffer and stained 8 h later with X-gal. Cultures which were not incubated at 37° C. (0-time) were exposed to peptides at ~23° C. for 1-2 min before they were rinsed and infected. No significant (95% confidence limit) differences in 0-time scores were found for any of the peptide-treated cultures as compared to the mock-treated controls indicating that peptides were rinsed off effectively.

Figure 25:
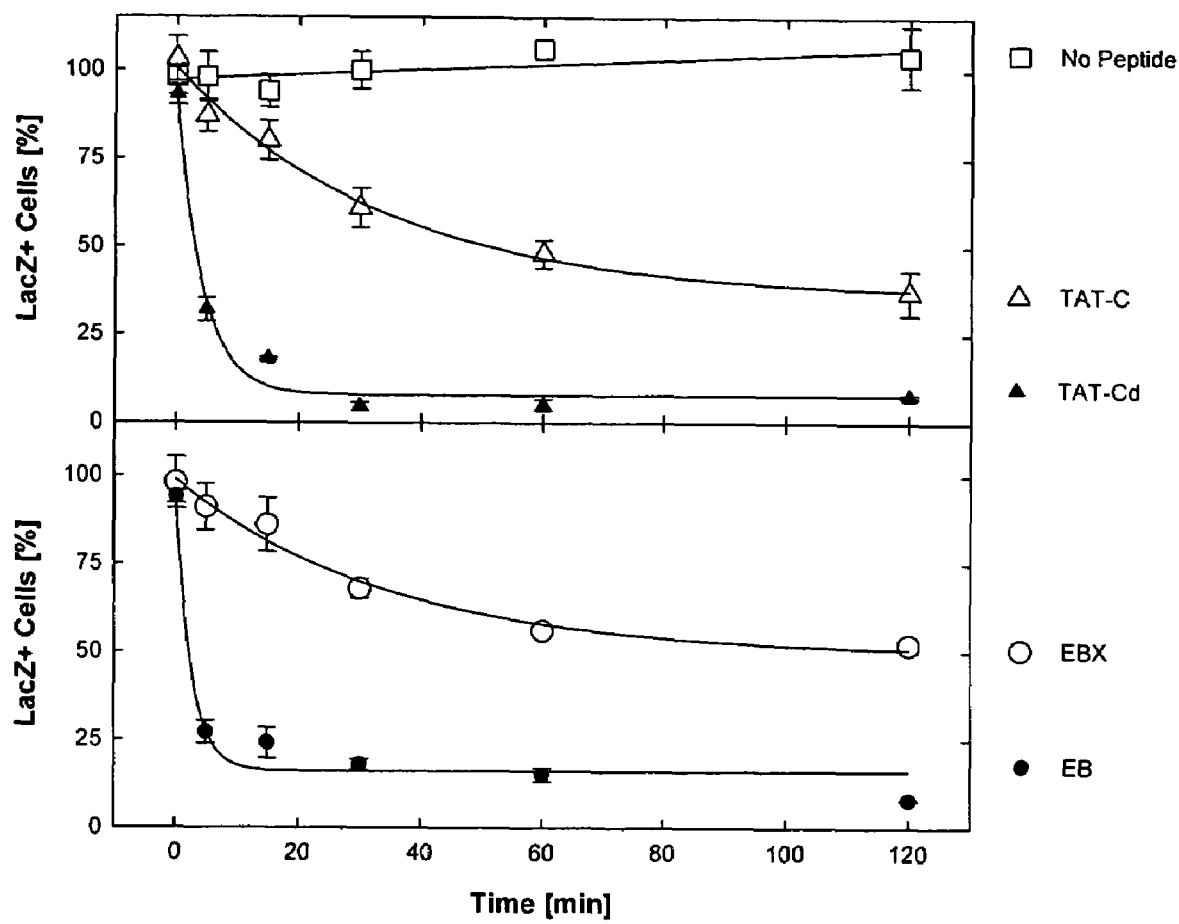

The results for this Example are shown in FIG. 25. The results show: cellular resistance to viral infection may be induced almost instantaneously by the most active peptides (TAT-Cd, EB), while other peptides act more slowly (1-2 h; TAT-C, EBX); and the most active peptides (TAT-Cd, EB) can induce cellular resistance so rapidly that viral pretreatments with these peptides become superfluous (see above).

Example 24

Induction of Cellular Resistance to Viral Infection by Various Peptides

Vero cells were infected with untreated virus (5400 pfu/well hrR3) in the absence of peptide following various cell pretreatments with peptides as described in the legend to FIG. 24. All peptides were used at a concentration of 30 µM, except for the two KLA-peptides, which were used at 10 µM because of their higher cytotoxicity. No cytotoxic effects were indicated by trypan blue staining. Means of triplicate determinations with standard errors of the means are indicated.

Figure 26:
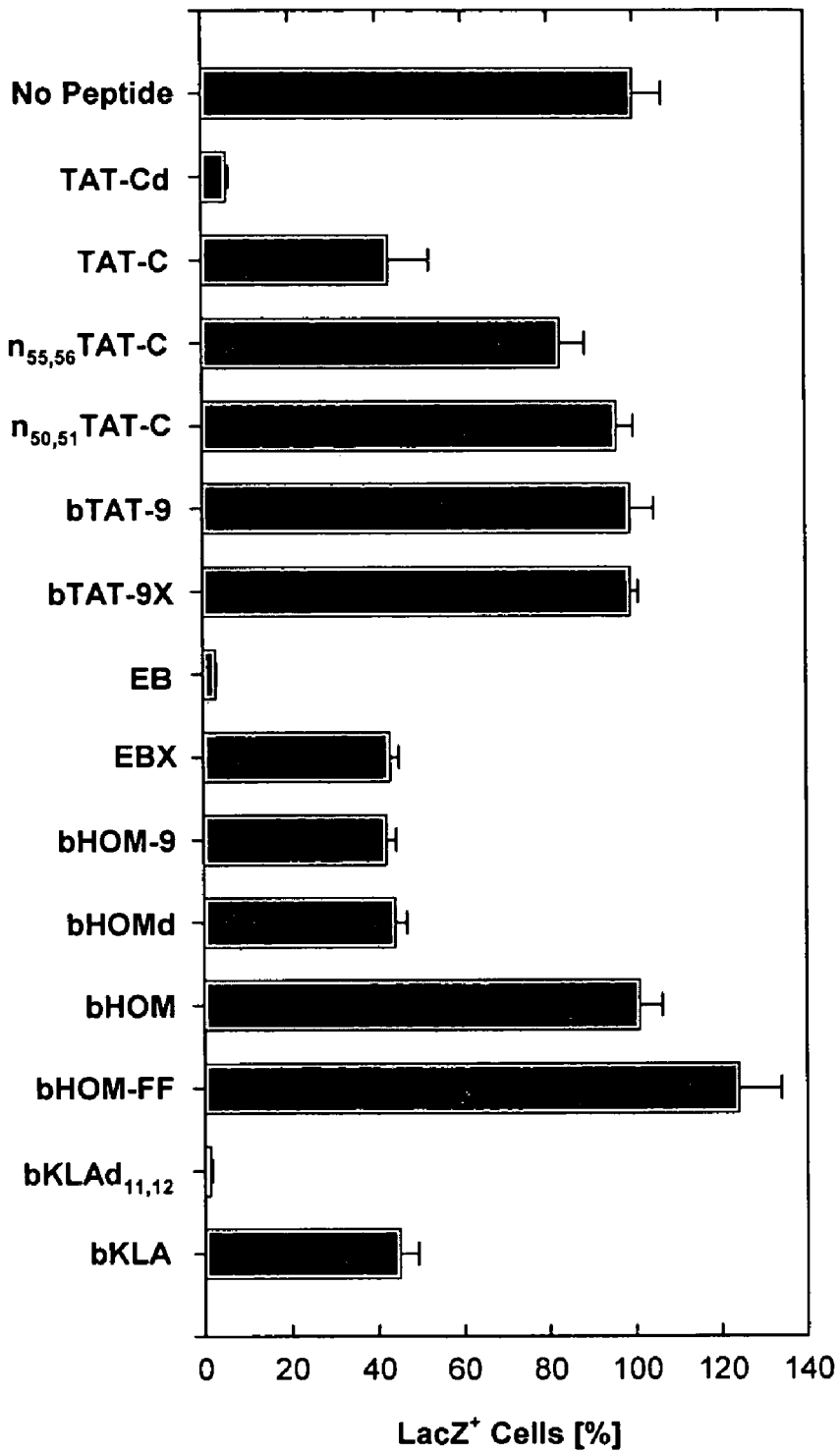

The results for this Example are shown in FIG. 26. FIG. 26 demonstrates that: 1) each of the four sets of peptides includes effective inducers of cellular resistance to viral infection; 2) there is a rough correspondence between the effectiveness of peptides as inducers of cellular resistance and as agent inactivating virions; and 3) peptides composed of D-isomers are more effective than the corresponding peptides composed of L-isomers.

Example 25

Induction of Cellular Resistance to Viral Infection in Primary Human Fibroblasts by TAT-Cd and EB Confluent human foreskin fibroblasts in 96-well plates were exposed to 30 µM peptide in Hepes-buffered serum supplemented DMEM for 1 h at 37° C. Peptide was rinsed off with the culture medium and cells were infected for 1 h at 37° C. (5100 pfu/mL hrR3) and stained with X-gal or trypan blue 8 h later. Means of triplicate determinations with standard errors of the means are indicated. No cytotoxic effects of the peptides were seen by trypan blue staining.

Figure 27:
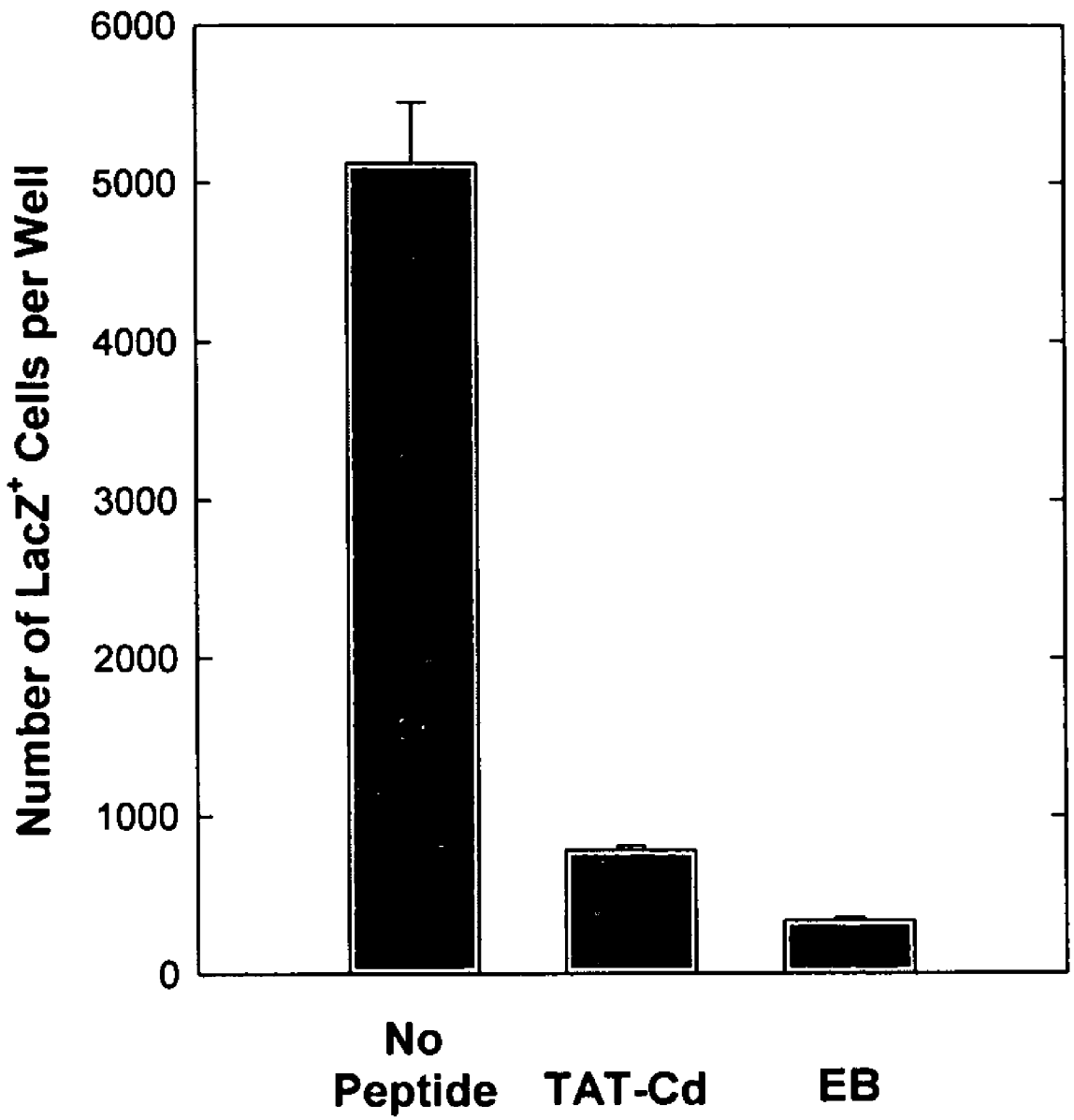
FIG. 27 is a graph showing the induction of cellular resistance to viral infection in primary human fibroblasts by TAT-Cd (SEQ ID NO:39) or EB (SEQ ID NO:1).

The results for this Example are shown in FIG. 27 which shows that induction of cellular resistance to viral infection is not cell-type specific.

Example 26

Reversibility of Peptide-induced Cellular Resistance to Viral Infection Under Normal Growth Conditions Confluent Vero cells plated in a strip well plate ($2\times10^5$ cells/well) were exposed to 30 µM TAT-Cd (•) or EB (▲), to 10 µM bKLA (Δ), or no peptide (○) for 1 h at 37° C. The peptides were rinsed off and cells were kept in normal culture medium for the indicated times when they were infected with untreated virus (8400 pfu/well hrR3) for 1 h and stained with X-gal 8 h later. Means of triplicate determinations with standard errors of the means are indicated.

Figure 28:
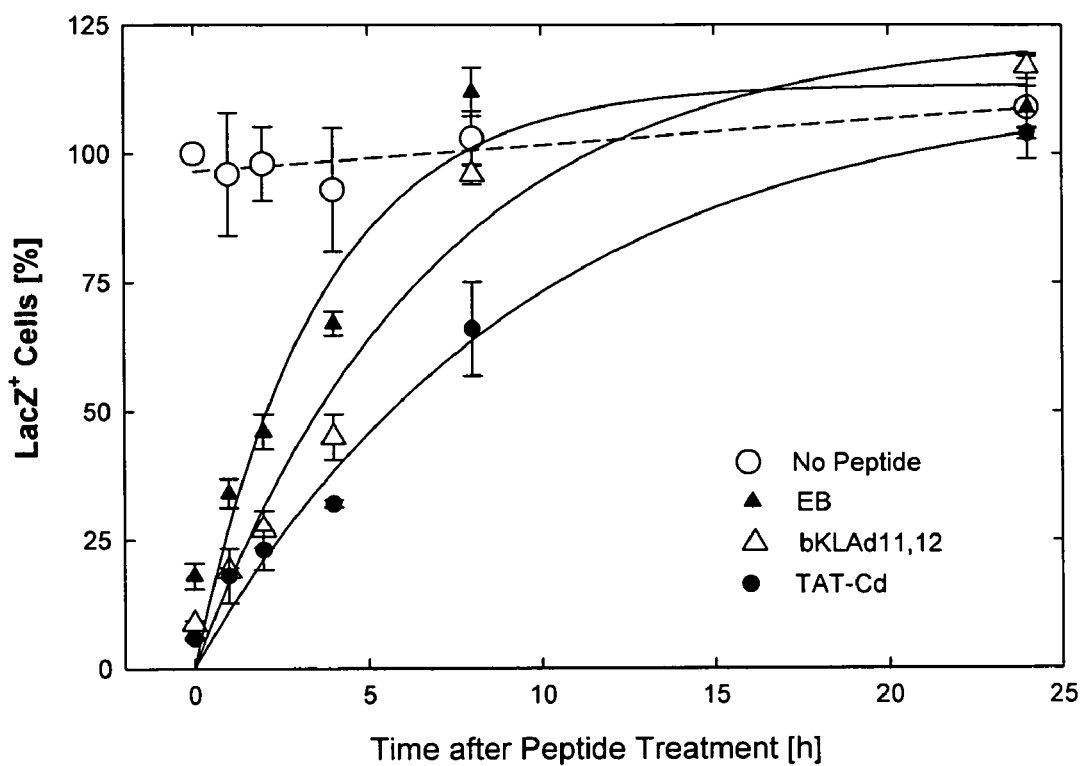
FIG. 28 is a plot demonstrating the time course of the reversibility of peptide-induced cellular resistance to viral infection under normal growth conditions. Curves (solid lines) are exponential rises to maxima (simple exponent, 2 parameters): $y=a(1-b^x)$ [did not see any difference from $y=a(1-e^{-bx})$].

The results for this Example are shown in FIG. 28, and are as follows: 1) cellular resistance to viral infection induced by the most effective peptides persists for several hours; 2) cellular resistance induced by other peptides may persist for shorter periods of time; and 3) cellular resistance induced by any peptide (1 h at 37° C.) is completely lost after one day (data not shown).

Example 27

Figure 29:
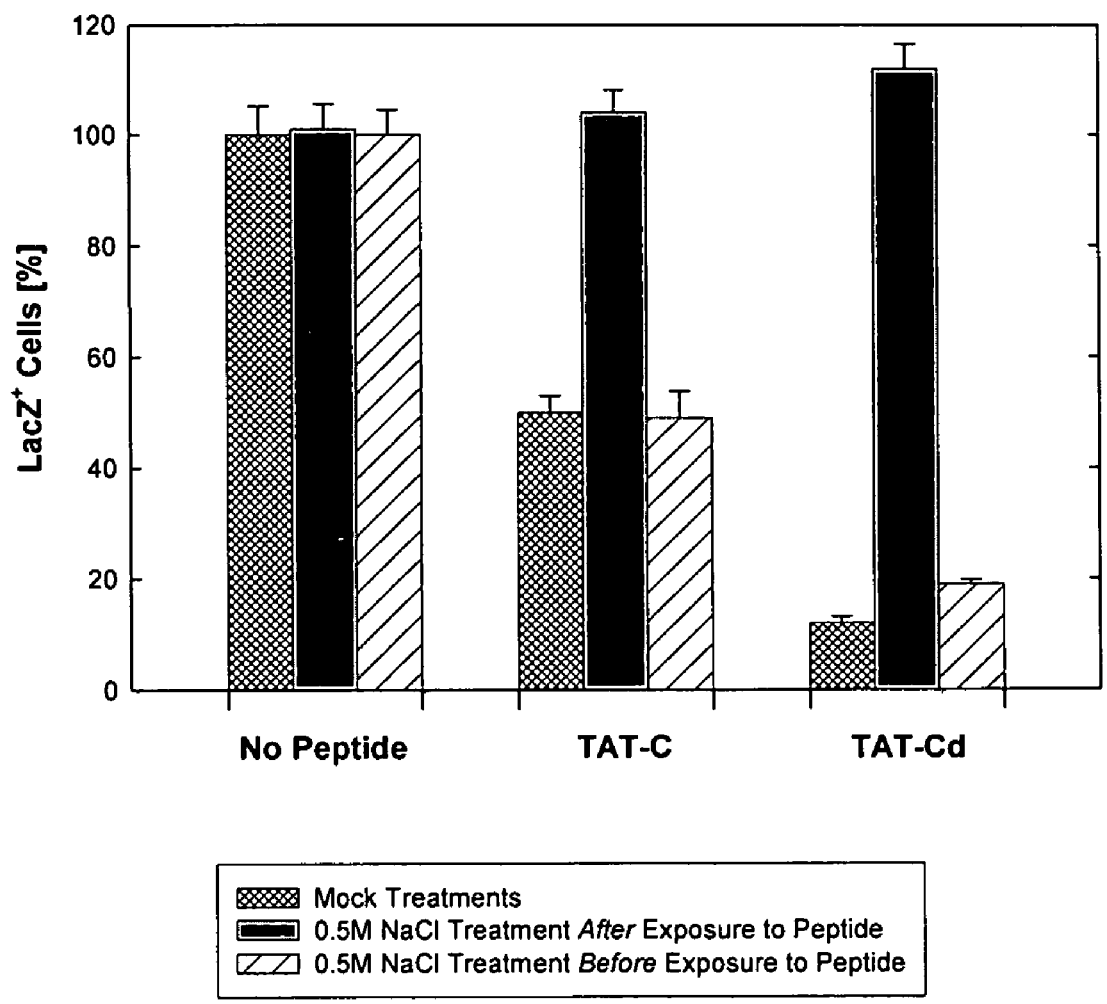
FIG. 29 is a graph showing that induction of cellular resistance to virus infection prior to infection by the TATC and TAT-Cd peptides is reversible by peptide extraction with high salt concentration.

Induction of Cellular Resistance to Virus Infection by TAT Peptides at 4° C. is Instantly Reversible by Rinsing Cells in the Presence of 0.5 M NaCl Prior to Infection Confluent Vero cell cultures ($2\times10^5$ cells/well) were exposed to 30 µM TAT-C, 30 µM TAT-Cd or no peptide for 1 h at 4° C., infected with untreated virus (8100 pfu/mL hrR3) for 1 h at 37° C., and stained with X-gal 8 h later. The results for this Example are shown in FIG. 29. When unbound peptides were rinsed off at 4° C. with culture medium alone (Hepes-buffered serum-supplemented DMEM; 3 rinses over a period of 5 min), infection was blocked by 50% (TAT-C) and 90% (TAT-Cd) (cross-hatched bars). When rinsed with the addition of 0.5 M NaCl to the medium, inhibition was completely reversed (gray bars). Rinsing cultures with 0.5 M NaCl supplemented medium only prior to the peptide treatments had little or no effect on the inhibitory activities of the peptides (hatched bars). Means of triplicate determinations with standard errors of the means are indicated.

Example 28

Differential Stability of Cellular Resistance to Viral Infection Induced by MT-peptides at 4° C. and 37° C.

Confluent Vero cell cultures ($2\times10^5$ cells/well) were exposed to various peptides at the indicated concentrations for 1 h at either 4° C. (left bars) or 37° C. (right bars) and rinsed with ice-cold culture medium without (gray bars) or with the addition of 0.5 M NaCl (cross-hatched bars). Cells were then infected for 1 h at 37° C. (9900 pfu/well hrR3) and stained with X-gal 8 h later. The data are means of triplicate determinations with standard errors of the means (100% corresponding to 350 LacZ+ cells/mm$^2$ counted in 4° C. controls rinsed without the addition of NaCl).

Figure 30:
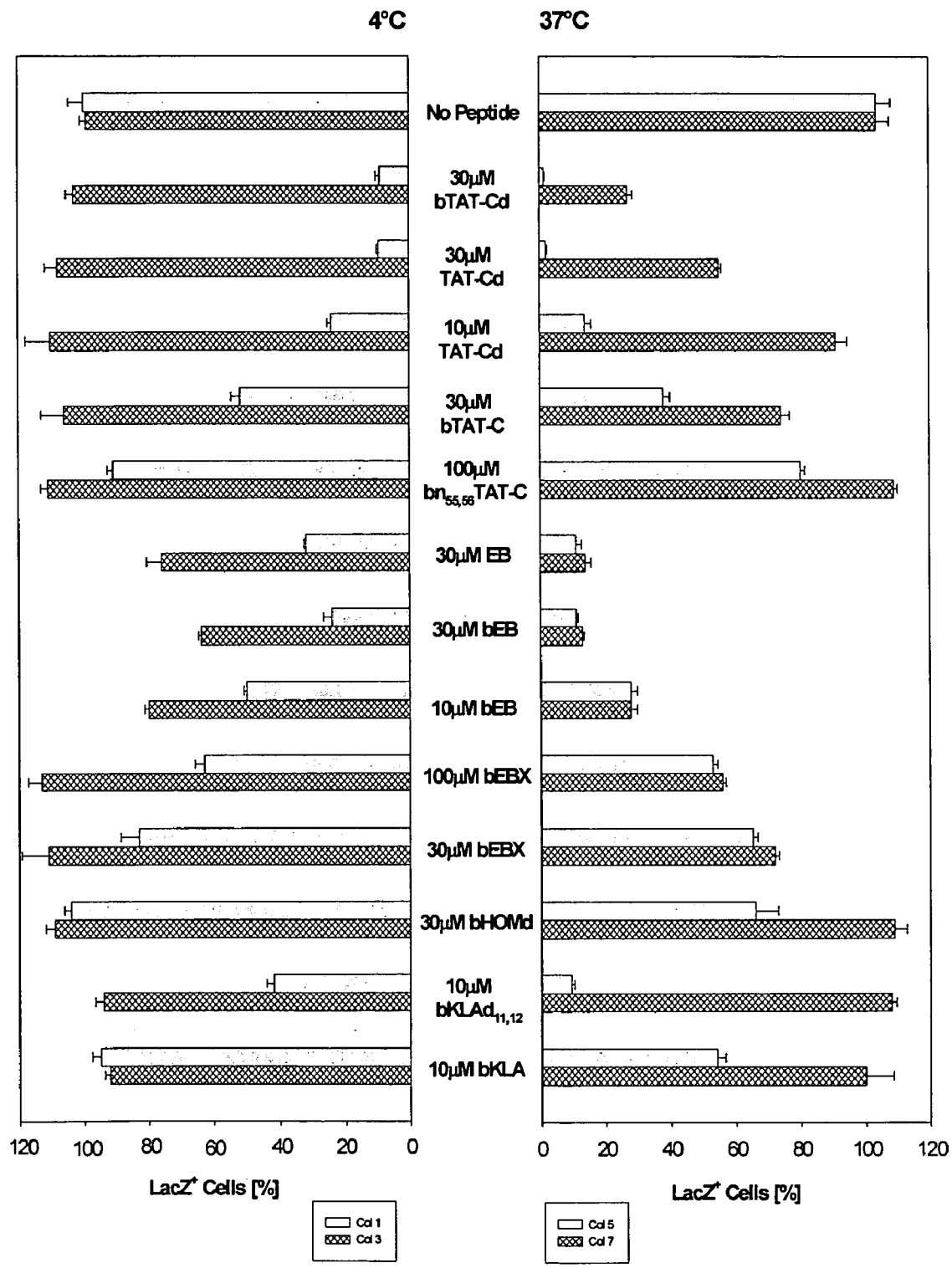
FIG. 30 is a graph demonstrating the differential stability of cellular resistance to viral infection induced by the present peptides.

The results for this Example are shown in FIG. 30. FIG. 30 demonstrates the following:

TAT peptides with intact MT sequences induce resistance to infection nearly as effectively at 4° as at 37° C. (gray bars);

Resistance induced by the TAT peptides at 4° C. was instantly and fully reversible by rinsing with 0.5 M NaCl (left cross-hatched bars) indicating that cells were exclusively protected by external peptide bound ionically to the cell surface;

Resistance induced by TAT peptides at 37° C. was only partially reversible by rinsing with 0.5 M NaCl (right cross-hatched bars) suggesting that cells may also become protected by internalized peptide or by more tightly bound or secluded peptide at the cell surface;

EB peptides, like TAT peptides, induced resistance to infection almost as effectively at 4° as at 37° C. (gray bars), but the EB-induced resistance was not as readily reversible in the presence of 0.5 M NaCl;

Resistance induced by EB at 4° C. was only partially reversible (left cross-hatched bars) and it was completely irreversible when induced at 37° C. (right cross-hatched bars) suggesting that EB-induced resistance depends primarily on internalized peptide or tightly bound external peptide.

A more limited study of HOM and KLA peptides showed that resistance induced by these peptides at both, 4° and 37° C., was fully reversible at high salt concentrations.

Example 29

Figure 31:
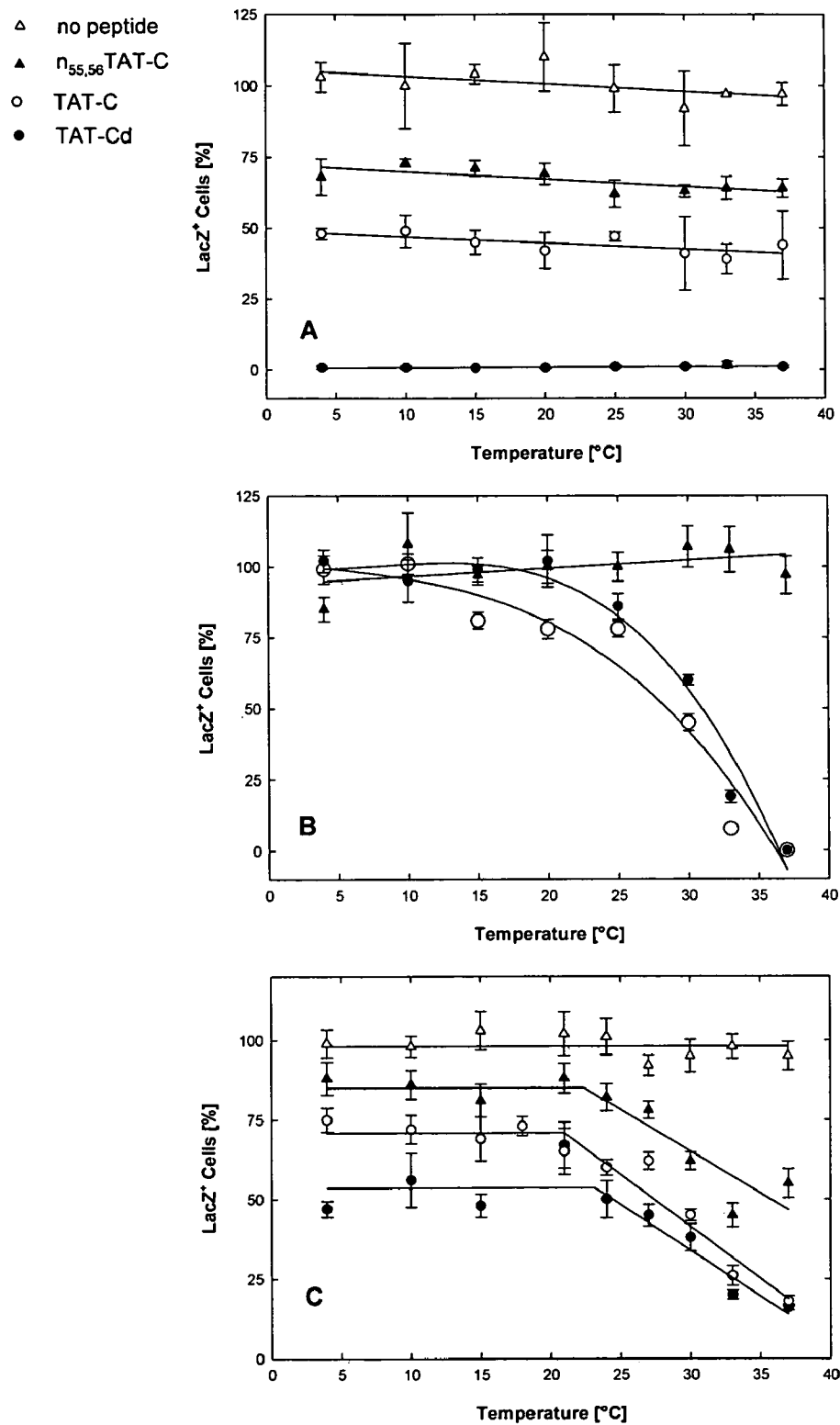

Induction of Cellular Resistance to Viral Infection, in Contrast to Virus Inactivation, is Temperature Independent The results for this Example are shown in FIG. 31. TAT-Cd (•), TAT-C(○), and $n_{55,56}$TAT-C (▲) were tested at temperatures between 4 and 37° C. and compared to mock-treated control (Δ) for their ability to induce cellular resistance to viral infection (A), to inactivate virions in solution in the absence of cells (B), and to inactivate virions adsorbed to cells at 4° C. (C).

For all experiments, Vero cells were plated in stripwells ($2\times10^5$ pfu/well) and kept in Hepes-buffered serum-supplemented DMEM throughout each of the assays. No cytotoxic effects were indicated in mock-infected trypan blue stain cultures. In (A), cellular resistance was induced by pretreating cells with 30 μM peptide and infecting them with untreated virus in the absence of peptide (as described above). In (B), virions (~$3\times10^6$ pfu/mL hrR3) in solution were exposed to 200 μM peptide for 1 h at the indicated temperatures. Aliquots of the treated virus (10 μL) were added to 1 mL ice-cold peptide-free medium, and the virus was pelleted (99 min at 13,200 rpm in an Eppendorf table-top centrifuge kept at 4° C.), resuspended in 250 μL medium and titered in Vero cell cultures. Mock-treated controls (data not shown) and samples treated with $n_{55,56}$TAT-C, which had no effect on virions at 200 μM, served as references to show that active virus was equally recovered at all temperatures. In (C), virus (5600 pfu/well hrR3) was adsorbed to pre-cooled Vero cells ($2\times10^5$ cells/well) for 1 h at 4° C. After rinsing off any free virus, cultures were exposed to 200 μM peptide for 1 h at the indicated temperatures. The peptides were rinsed off and cells were stained with X-gal 8 h later. The results for this example are as follows:

Induction of resistance to infection by TAT peptides is temperature independent, whereas inactivation of virions is not; and Inactivation of adsorbed virus by TAT peptides apparently depends on both, temperature-independent inductions of cellular resistance to infection (below 24° C.) and temperature-dependent direct inactivation of virions (above 24° C.).

IV.—Induction of Cellular Resistance

Example 30

Cellular resistance to virus infection was effectively induced by the first exposure to EB (•; $IC_{50}=4$ μM) and largely lost over the following 8.5 h (period ○; $IC_{50}>100$ μM). The second exposure to EB, however, restored cellular resistance to infection at least as effectively as the first exposure (▲; $IC_{50}=2.5$ μM). Thus, cellular resistance to virus infection can be induced repeatedly by successive exposures to peptide at intervals of several hours. The data are shown in FIG. 32.

Example 31

In Vitro Toxicity

To test if these peptides had cytotoxic effects on a variety of cell lines, the MTS analysis was carried out on eight cell lines. FIGS. 33A, 33B, 33C, 33D, 33E, 33F, 33G, and 33H show the results of MTS assay in HeLa, CV-1 PD, TM-1, DP-9, CEMx174, NIKS, and W12E cells. The results were similar to those in Vero cells. For the EB peptide, the $EC_{50}$ values were greater than 100 μM, with the exception of CEMx174 (50 μM). The TAT-C peptide was not toxic even at a concentration of 400 μM in all cell lines tested. With the bHOM peptide, the $EC_{50}$ values were greater than 200 μM for W12E, NIKS, and TM-1 cells and were 50 μM, 75 μM, 100 μM, 150 μM, and 180 μM for CEMxl74, Vero, HeLa, DP-9, and CV-1PD cells, respectively. Therefore, both the active MTPs (EB, TAT-C, and bHOM), and their inactive versions (EBX, $n_{55,56}$TAT-C, and bHOM-FF, respectively) were generally not cytotoxic to cells.

Example 32

In Vivo Toxicity

Figure 34:
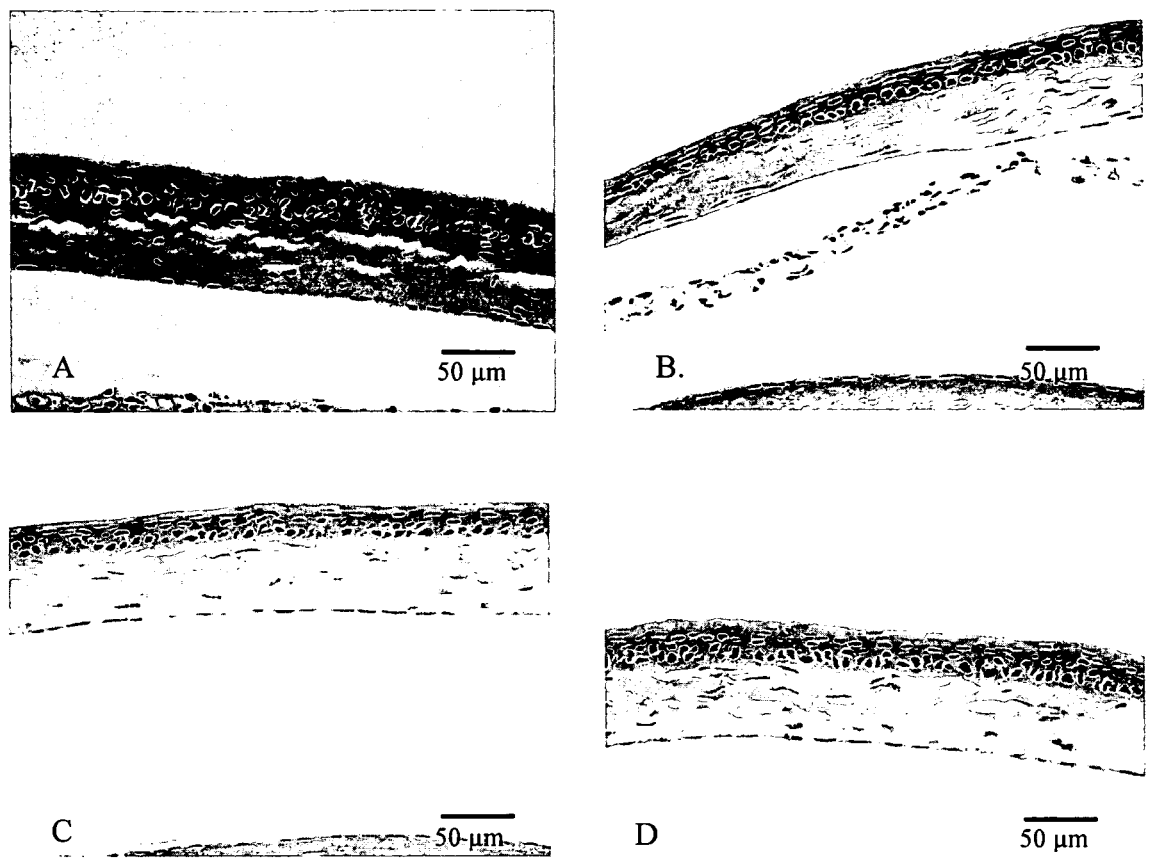

To determine if the peptides were toxic in vivo, they were applied to the corneas of female BALB/C mice (4-6 weeks old) four times a day for seven days (FIG. 34). The concentrations used were approximately 1000 times higher than the $IC_{50}$ values obtained in the in vitro experiments. The severity of blepharitis, punctate keratopathy, dendrite ulceration, and geographic ulceration was scored at various times post-treatment (1, 5, and 7 days). The control for this experiment was no-peptide treatment. The TAT-C, TAT-Cd (D-version of TAT-C peptide), and bHOMd (D-version of bHOM) peptides caused mild blepharitis in mice, whereas the EB peptide had no effect. The TAT-Cd and bHOMd peptides were previously shown to have relatively similar antiviral activity as TAT-C and bHOM.

Punctate keratopathy, dendrite ulceration, and geographic ulceration also were examined by calcein staining and microscopic examination of the cornea. The TAT-Cd, and bHOMd peptides caused very mild punctate keratopathy. None of the peptides caused dendritic ulceration. No evidence of geographic ulceration in the cornea was observed. The control, EB, EBX, and $n_{50,5}{}^{18}$TAT-C treated groups showed no evidence of corneal pathology. Analysis of tissue sections (FIG. 34) revealed no evidence of pathology or toxicity, including cell necrosis, epithelial cell proliferation, stromal edema, or endothelial cell loss indicating that treatment with the peptides four times daily for seven days did not adversely affect the cornea. There were also no changes seen in the lens, retina, or any other structures in the eye.

The peptides were also tested for in vivo toxicity in the mouse vagina. The same peptide concentrations (6.1 mM EB, 7.5 mM TAT-C, and 11.2 mM bHOMd peptides) as in the corneal study were used. Treatment with 6.6% nonoxynol-9 (N-9), which is widely used as a microbicide, and PBS in the vagina served as controls. The concentration of N-9 selected for this experiment corresponds to the average (6.6%) concentration of N-9 used with barrier contraceptives. FIG. 35 shows low magnification views of the H&E stained sections of mouse vagina treated with PBS (A), 6.6% N-9 (B), EB (C), bHOMd (D), and TAT-C (E). The presence of inflammatory cells in the lumen as indicated by the arrows, was observed in all samples, including vaginas treated with the PBS control. There was no evidence of damage to the epithelium (ulceration), infiltration of inflammatory cells into the epithelium, epithelial thinning or hyperplasia, and the presence of intracellular glycogen was similar in all samples. Higher magnification images of mouse vaginas treated with the peptides are shown in FIG. 35. No differences in the appearance of the tissues was seen in any of the samples, including those treated with N-9. Thus, exposure to the peptides did not adversely affect vaginal tissues. We also saw no differences in the cervix, uterus, fallopian tube, ovary, or any other structures in the female reproductive tract in any of the groups. We observed occasional pockets of inflammatory cells in the vaginal epithelium, but these were seen in tissues exposed to all treatments, including animals receiving PBS only (FIG. 36). No differences in the number of these pockets, nor tissue size were observed between any of the samples.

Discussion of Part IV

Peptide Toxicity

The cytotoxic effects of MTPs and control peptides, in which the transiting sequences had been altered, were evaluated in vitro in eight cell lines (Vero, HeLa, DP-9, TM-1, CV-1PD, CEMx 174, NIKS, and W12E) by MTS Assay. The results showed that all peptides tested gave the $EC_{50}$ values that were significantly above those for antiviral activity in all cell types tested.

Studies to examine the effect of the peptides in vivo or intact epithelium supported the conclusions from the in vitro data. In the cornea, we observed some changes in the epithelium after staining with calcein, which does not stain intact epithelium, but these changes were very mild, did not involve extensive areas of the cornea, and were transient. Histopathological analysis of corneas failed to show any evidence of toxicity, nor did the peptides stimulate infiltration of inflammatory cells. We also found no evidence of toxicity or pathology in the vagina tissues, nor did we see increased inflammation in the vaginal epithelium. Therefore, these results indicate the peptides have a favorable toxicity profile.

The data shown in examples 22 through 32 show that peptides with membrane transiting motifs have an additional protective activity. That is, they are capable of rendering cells resistant to virus infection. The resistance is not cell type or species specific since the resistance could be induced in both primary human foreskin fibroblasts and Vero cells (African Green Monkey Kidney). This cellular resistance phenomenon is induced at different rates, even as fast as 5 minutes of exposure, depending on the peptide used. In all cases, resistance was induced even after peptide treated cells were extensively washed to remove as much peptide as possible. This washing step removes peptide that is not bound to cells but peptide could clearly remain bound to cells and be involved in the resistance effect. This observation is supported by our finding that washing with 0.5 M sodium chloride reverses the effect of TAT peptides, suggesting that peptide bound to cells may be involved. For the EB peptide, this is not clear since salt treatment did not reverse the resistance effect. Either EB triggers some event responsible for resistance or the EB peptide binds tightly to cells and this bound peptide could be involved in resistance. Regardless of whether the effect is due to residual peptide or some event triggered by peptide exposure, the fact that peptide exposure induces resistance to infection shows the feasibility of using these peptides for prophylaxis against viral infection.

The feasibility of using peptide exposure prophylactically is further underscored by the observation that the resistance effect lasts several hours. For example, the halftime to recover susceptibility to infection for the EB peptide is on the order of 5 to 6 hours; thus, periodic dosing could provide a substantial protective effect. This results is also significant for the use of these peptides to prevent transmission of sexually transmitted viral infections in that a single use prior to intercourse could protect an individual for several hours thereafter.

Finally, the utility of the peptides is also supported by the finding that cells can be treated with peptide to induce resistance, allowed to recover susceptibility, and then reexposed to the same peptide to induce resistance. This finding supports the use of these peptides to prevent infection prophylactically by the administration of repeated doses several hours apart.

In summary, the examples now add an additional protective activity of peptides carrying membrane transiting domains; the induction of resistance to cells prior to viral infection. Thus, virus infection is prevented by these peptides by three mechanisms. They have microbicidal activity and inactivate virus. They prevent the entry of virus into cells whether the viruses are exposed to the peptide prior to cell contact or after adsorption has occurred, and they induce a state of resistance to viral infection in cells exposed to the peptides. The combination of the three methods of antiviral activity is powerful and supports the utility of these peptides for dealing with viral infection.

The present peptides can have any or all of the components described herein. Likewise, the present methods can be carried out by performing any of the steps described herein, either alone or in various combinations. One skilled in the art will recognize that all embodiments of the present invention are capable of use with all other appropriate embodiments of the invention described herein. Additionally, one skilled in the art will realize that the present invention also encompasses variations of the present peptides, configurations and methods that specifically exclude one or more of the components or steps described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference thereto. Unless otherwise specified, "a" or "an" means "one or more".

While preferred embodiments have been illustrated and described, it should be understood that changes and modifications can be made therein in accordance with ordinary skill in the art without departing from the invention in its broader aspects as defined in the following claims.

The Following References are Additionally Incorporated by Reference:

1. Aldrian-Herrada, G., M. G. Desarménien, H. Orcel, L. Boissin-Agasse, J. Méry, J. Brugidou, and A. Rabié. "A peptide nucleic acid (PNA) is more rapidly internalized in cultured neurons when coupled to a retro-inverso delivery peptide. The antisense activity depresses the target mRNA and protein in magnocellular oxytocin neurons." *Nucleic Acids Res.* 26: 4910-4916, 1998.
2. Banfield, B. W., Y. Leduc, L. Esford, R. J. Visalli, C. R. Brandt, and F. Tufaro. "Evidence for an interaction of herpes simplex virus with chondroitin sulfate proteoglycans during infection." *Virology* 208:531-539, 1995.
3. Berkowitz, B. A., C. L. Bevins, and M. A. Zasloff. Magainins: "A new family of membrane-active host defense peptides." *Biochem. Pharmacol.* 39:625-629, 1990.
4. Brandt, C. R., Coakley, L. M., and Grau, D. R. "A murine model of herpes simplex virus-induced ocular disease for antiviral drug testing." *J. Virol. Methods.* 36: 209-222, 1992.
5. Brandt, C. R., Spencer, B., Imesch, P., Garneau, M., and Deziel, R. "Evaluation of a peptidomimetic ribonucleotide reductase inhibitor with a murine model of herpes simplex virus type 1 ocular disease." *Antimicrob. Agents Chemother.* 40: 1078-1084, 1996.
6. Bultmann, H., Busse, J. S., and Brandt, C. R: "Modified FGF4 signal peptide inhibits entry of herpes simplex virus type 1." *J. Virol.* 75: 2634-2645, 2001.
7. Bultmann, H., and Brandt, C. R.: "Peptides containing membrane-transiting motifs inhibit virus entry." *J. Biol. Chem.* 277: 36108-36023, 2002.
8. Cai, W., B. Gu, and S. Person. "Role of glycoprotein B of herpes simplex virus type I in viral entry and fusion." *J. Virol.* 62: 2596-2604, 1988.
9. Campadelli-Fiume, G., D. Stirpe, A. Boscano, E. Avitabile, L. Foa-Tomasi, D. Barker, and B. Roizman. 1990. "Glycoprotein C-dependent attachment of herpes simplex virus to susceptible cells leading to productive infection." *Virology* 178: 213-222, 1990.
10. Chou, P. Y. and G. D. Fasman. "Prediction of the secondary structure of proteins from their amino acid sequence." *Adv. Enzymol Related Areas Mol. Biol.* 47: 45-147, 1978.
11. Cockrell, A. S., and M. I. Muggeridge. "Herpes simplex virus type 2 UL45 is a type II membrane protein." *J. Virol.* 72: 4430-4433, 1998.
12. Coen, D. M., D. P. Aschman, P. T. Gelep, M. J. Retondo, S. K. Weller, and P. A. Schaffer. 1984. "Fine mapping and molecular cloning of mutations in the herpes simplex virus DNA polymerase locus." *J. Virol.* 49: 236-247, 1984.
13. Cohen, E. A., Gandreau, P., Brazeau, P., and Langelier, Y. "Specific inhibition of herpesvirus ribonucleotide reductase by a nonapeptide derived from the carboxy terminus of subunit 2." *Nature,* 321: 441-443, 1986.
14. Derossi, D., A. H. Joliot, G. Chassaing, and A. Prochiantz. "The third helix of the antennapedia homeodomain translocates through biological membranes" *J. Biol. Chem.* 269: 1044-1050, 1994.
15. Derossi, D., Calvet, S., Trembleau, A., Brunissen A, Chassaing G, and Prochiantz A. "Cell internalization of the third helix of the antennapedia homeodomain is receptor-independent." *J. Biol. Chem.* 271: 18188-18193, 1996.
16. Derossi, D., Chassaing, G., and Prochiantz, A. "Trojan peptides: the penetration system for intracellular delivery." *Trends Cell. Biol.* 8: 84-87, 1998.
17. Desai, P. J., P. A. Schaffer, and A. C. Minson. "Excretion of non-infectious virus particles lacking gH by a temperature-sensitive mutant of herpes simplex virus type I: Evidence that gH is essential for virion infectivity." *J. Gen. Virol.* 69: 1147-1156, 1988.
18. Dutia, B, Frame, M. C., Subak-Sharpe, J. H., Clark, W. N., and Marsden, H. S. "Specific inhibition of herpesvirus ribonucleotide reductase by synthetic peptides." *Nature* 321: 439-441, 1986.
19. Fawell, S., J. Seery, Y. Daikh, C. Moore, L. L. Chen, B. Pepinsky, and J. Barsoum. "Tat-mediated delivery of heterologous proteins into cells." *Proc. Natl. Acad. Sci. USA* 91: 664-668, 1994.
20. Fields, C. G., D. H. Lloyd, R. L. Macdonald, K. M. Otteson, and R. L. Noble. "HBTU activation for automated Fmoc solid-phase peptide synthesis." *Peptide Res.* 4: 95-101, 1991.
21. Flores, E. R., Allen-Hoffmann, B. L., Lee, D., Sattler, C. A., and Lambert, P. F. "Establishment of the human papillomavirus type 16 (HPV-16) life cycle in an immortalized human foreskin keratinocyte cell line." *Virology* 262: 344-354, 1999.
22. Fuller, A. D., and P. G. Spear. "Anti-glycoprotein D antibodies that permit adsorption but block infection by herpes simplex virus 1 prevent virion-cell fusion at the cell surface." *Proc. Natl. Acad. Sci. USA* 84: 5454-5458, 1987.
23. Fuller, A. O., and W.-C. Lee. "Herpes simplex virus type I entry through a cascade of virus-cell interactions requires different roles of gD and gH in penetration." *J. Virol.* 66: 5002-5012, 1992.

24. Gariepy, J. and Kawamura, K. "Vectorial delivery of macromolecules into cells using peptide-based vehicles." *Trends Biotechnol.* 19: 21-28, 2001.
25. Geraghty, R. J., C. Krummenacher, G. Cohen, R. J. Eisenberg, and P. G. Spear. "Entry of alphaherpesviruses mediated by poliovirus receptor related protein 1 and poliovirus receptor." *Science* 280: 1618-1620, 1998.
26. Gibbs, J. S., H. C. Chiou, J. D. Hall, D. W. Mount, M. J. Retondo, S. K. Weller, and D. M. Coen. "Sequence and mapping analysis of the herpes simplex virus DNA polymerase gene predicts a c-terminal substrate binding domain." *Proc. Natl. Acad. Sci. USA* 82: 7969-7973, 1985.
27. Goldstein, D. J. and Weller, S. K.: "Factor(s) present in herpes simplex virus type 1-infected cells can compensate for the loss of the large subunit of the viral ribonucleotide reductase: characterization of an ICP6 deletion mutant." *Virology* 166: 41-51, 1988.
28. Grau, D. R., R. J. Visalli, and C. R. Brandt. "Herpes simplex virus stromal keratitis is not titer-dependent and does not correlate with neurovirulence." *Invest. Ophthalmol. Vis. Sci.* 30: 2474-2480, 1989.
29. Haanes, E. J., C. M. Nelson, C. L. Soule, and J. L. Goodman. "The UL45 gene product is requires for herpes simplex virus type 1 glycoprotein B-induced fusion." *J. Virol.* 68: 5825-5834, 1994.
30. Hall, J. D., and S. Woodward. "Aphidicolin resistance in herpes simplex virus type 1 appears to alter substrate specificity in the DNA polymerase." *J. Virol.* 63: 2874-2876, 1989.
31. Handler, C. G., G. Cohen, and R. J. Eisenberg. "Cross-linking of glycoprotein oligomers during herpes simplex virus type 1 entry." *J. Virol.* 70: 6076-6082, 1996.
32. Hawiger, J. "Noninvasive intracellular delivery of functional peptides and proteins." *Curr. Opin. Chem. Biol.* 3: 89-94, 1999.
33. Herold, B. C., D. WuDunn, N. Soltus, and P. G. Spear. "Glycoprotein C of herpes simplex virus type 1 plays a principal role in the adsorption of virus to cells and in infectivity." *J. Virol.* 65: 1090-1098, 1991.
34. Herold, B. C., R. J. Visalli, N. Susmarski, C. R. Brandt, and P. G. Spear. "Glycoprotein C-independent binding of herpes simplex virus to cells requires cell surface heparan sulphate and glycoprotein B." *J. Gen. Virol.* 75: 1211-1222, 1994.
35. Herold, B. C., S. I. Gerber, B. J. Belval, A. M. Siston, and N. Shulman. "Differences in the susceptibility of Herpes simplex virus types 1 and 2 to modified heparan compounds suggest serotype differences in viral entry." *J. Virol.* 70: 3461-3469, 1996.
36. Highlander S, Sutherland S L, Gage P J, D. C. Johnson, M. Levine, and J. C. Glorioso. "Neutralizing monoclonal antibodies specific for herpes simplex virus glycoprotein D inhibit virus penetration." *J. Virol.* 61: 3356-3364, 1987.
37. Hutchinson, L., L. K. Goldsmith, H. Browne, V. Wargent, N. Davis-Poynter, S. Primorac, K. Goldsmith, A. C. Minson, and D. C. Johnson. "A novel herpes simplex virus type 1 glycoprotein forms a complex with glycoprotein H (gH) and affects normal folding and surface expression of gH." *J. Virol.* 66: 2240-2250, 1992.
38. Johnson, D. C., and P. G. Spear. "Herpes simplex virus glycoprotein D mediates interference with herpes simplex virus infection." *J. Virol.* 63: 819-827, 1989.
39. Kilby, M. J., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. "Potent suppression of HIV-1 replication in humans by T-20, a peptide inhibitor of gp41-mediated virus entry." *Nature Med.* 11: 1302-1307, 1998.
40. Knopf, C. W. "The herpes simplex virus type 1 DNA polymerase gene: Site of phosphonoacetic acid resistance mutation in strain Angelotti is highly conserved." *J. Gen. Virol.* 68: 1429-1433, 1987.
41. Krummenacher, C., A. V. Nicola, J. C. Whitbeck, H. Lou, W. Hou, J. D. Lambris, R. J. Geraghty, P. G. Spear, G. H. Cohen, and R. J. Eisenberg. "Herpes simplex virus glycoprotein D can bind to poliovirus receptor-related protein 1 or herpesvirus entry mediator, two structurally unrelated mediators of virus entry." *J. Virol.* 72: 7064-7074, 1998.
42. Laquerre, S., R. Argnani, D. B. Anderson, S. Zucchini, R. Manservigi, and J. C. Glorioso. "Heparan sulfate proteoglycan binding by herpes simplex virus type 1 glycoproteins B and C, which differ in their contributions to virus attachment, penetration, and cell to cell spread." *J. Virol.* 72: 6119-6130, 1998.
43. Ligas, M. W., and D. C. Johnson. "A herpes simplex virus mutant in which glycoprotein D sequences are replaced by β-galactosidase sequences binds to, but is unable to penetrate into cells." *J. Virol.* 62: 1486-1494, 1988.
44. Lin, Y.,-Z., S.-Y. Yao, R. A. Veach, T. R. Torgerson, and J. Hawiger. "Inhibition of nuclear translocation of transcription factor NF-κβ by a synthetic peptide containing a cell membrane-permeable motif and nuclear localization sequence." *J. Biol. Chem.* 270: 14255-14258, 1995.
45. Lycke, E., M. Johansson, B. Svennerholm, and U. Lindahl. "Binding of herpes simplex virus to cellular heparan sulfate, an initial step in the adsorption process." *J. Gen. Virol.* 72: 1131-1137, 1991.
46. Manservigi, R., P. G. Spear, and A. Buchan. "Cell fusion induced by herpes simplex virus is promoted and suppressed by different viral glycoproteins." *Proc. Natl. Acad. Sci. USA* 74: 3913-3917, 1977.
47. Matthews, J. T., B. J. Terry, and A. K. Field. "The structure and function of the HSV DNA replication proteins: Defining novel antiviral targets." *Antiviral Res.* 20: 89-114, 1993.
48. Meienhofer, J., M. Waki, E. P. Heimer, T. J. Lambros, R. C. Makofske, and C. D. Chang. "Solid phase synthesis without repetitive acidolysis: Preparation of leucyl-alanyl-glycyl-valine using 9-fluorenylmethyloxycarbonylamino acids." *Int. J. Peptide Protein Res.* 13: 35-42, 1979.
49. Merrifield, R. B. "Solid phase peptide synthesis I. The synthesis of a tetrapeptide." *J. Am. Chem. Soc.* 85: 7129-7133, 1963.
50. Minson, A. C., T. C. Hodgman, P. Digard, D. C. Hancock, S. E. Bell, and E. A. Buckmaster. "An analysis of the biological properties of monoclonal antibodies against glycoprotein D of herpes simplex virus and identification of amino acid substitutions that confer resistance to neutralization." *J. Gen. Virol.* 67: 1001-1013, 1986.
51. Montgomery, R. I., M. S. Warner, B. J. Lum, and P. G. Spear. "Herpes simplex virus-1 entry into cells mediated by a novel member of the TNF/NGF receptor family." *Cell* 87:427-436, 1996.
52. Nicola, A. V., S. H. Willis, N. Naidoo, R. J. Eisenberg, and G. Cohen. "Structure function analysis of soluble forms of herpes simplex virus glycoprotein D." *J. Virol.* 70: 3815-3822, 1996.

53. Nicola, A. V., M. Ponce de Leon, R. Xu, W. Hou, J. C. Whitbeck, C. Krummenacher, R. I. Montgomery, P. G. Spear, R. J. Eisenberg, and G. H. Cohen. "Monoclonal antibodies to distinct sites on herpes simplex virus (HSV) glycoprotein D block HSV binding to HVEM." *J. Virol.* 72: 3595-3601, 1998.
54. Nisole, S., B. Krust, C. Callebaut, G. Guichard, S. Muller, J.-P. Briand, and A. G. Hovanessian. "The anti-HIV pseudopeptide HB-19 forms a complex with the cell-surface-expressed nucleolin independent of heparan sulfate proteoglycans." *J. Biol. Chem.* 274: 27875-27884, 1999.
55. Oehlke, J., E. Krause, B. Wiesner, M. Beyermann, and M. Bienert. "Nonendocytic, amphipathicity dependent cellular uptake of helical model peptides." *Protein Peptide Lett.* 3: 393-398, 1996.
56. Oehlke, J., E. Krause, B. Wiesner, M. Beyermann, and M. Bienert. "Extensive cellular uptake into endothelial cells of an amphipathic □-sheet forming peptide." *FEBS Lett.* 415: 196-199, 1997.
57. Pooga, M., M. Hällbrink, M. Zorko, and Ü Langel. "Cell penetration by transportan." *FASEB J.* 12: 67-77, 1998.
58. Rimsky, L. T., D. C. Shugars, T. J. Matthews. "Determinants of human immunodeficiency virus type 1 resistance to gp41-derived inhibitory peptides." *J. Virol.* 72: 986-993, 1998.
59. Roop, C., L. Hutchinson, and D. C. Johnson. "A mutant herpes simplex virus type 1 unable to express glycoprotein L cannot enter cells and its particles lack glycoprotein H." *J. Virol.* 67: 2285-2297, 1993.
60. Sasadeusz, J. J., F. Tufaro, S. Safrin, K. Schubert, M. M. Hubinette, P. K. Cheung, and S. L. Sacks. "Homopolymer mutational hot spots mediate herpes simplex virus resistance to acyclovir." *J. Virol.* 71: 3872-3878, 1997.
61. Schwarze, S. R., A. Ho, A. Vocero-Akbani, and S. F. Dowdy. "In vivo protein transduction: Delivery of a biologically active protein into the mouse." *Science* 285: 1569-1572, 1999.
62. Schwarze, S. R., Hruska, K. A. and Dowdy, S. F. "Protein transduction: unrestricted delivery into all cells." *Trends Cell Biol.* 10: 290-295, 2000.
63. Sears, A. E., B. S. McGwire, and B. Roizman. "Infection of polarized MDCK cells with herpes simplex virus 1: Two asymetrically distributed cell receptors interact with different viral proteins." *Proc. Natl. Acad. Sci. USA* 88: 5087-5091, 1991.
64. Segel, I. H. "Biochemical Calculations," $2^{nd}$ ed. John Wiley & Sons, Inc., New York, N.Y., 1976.
65. Shieh, M. T., D. WuDunn, R. I. Montgomery, J. D. Esko, and P. G. Spear. "Cell surface receptors for herpes simplex virus are heparan sulfate proteoglycans." *J. Cell Biol.* 116: 1273-1281, 1992.
66. Shieh, M. T., and P. G. Spear. "Herpes virus-induced cell fusion that is dependent on cell surface heparan sulfate or soluble heparan." *J. Virol.* 68: 1224-1228, 1994.
67. Spear, P. G. "Entry of alphaherpesviruses into cells." *Sem. Virol.* 4: 167-180, 1993.
68. Srinivas, R. V., B. Birkedal, R. J. Owens, G. M. Anantharamaiah, J. P. Segrest, and R. W. Compans. "Antiviral effects of apolipoprotein A-I and its synthetic amphipathic peptide analogs." *Virology* 176: 48-57, 1990.
69. Srinivas, S. K., R. V. Srinivas, G. M. Anantharamaiah, J. P. Segrest, and R. W. Compans. "Membrane interactions of synthetic peptides corresponding to amphipathic helical segments of the human immunodeficiency virus type-1 envelope glycoprotein." *J. Biol. Chem.* 267: 7121-7127, 1992.
70. Stephens, D. J. and Pepperkok, R. "The many ways to cross the plasma membrane." *Proc. Natl. Acad. Sci USA* 98, 4295-4298, 2001.
71. Tal-Singer, R., C. Peng, M. Ponce de Leon, W. R. Abrams, B. W. Banfield, F. Tufaro, G. H. Cohen, and R. J. Eisenberg. "Interaction of herpes simplex virus glycoprotein C with mammalian cell surface molecules." *J. Virol.* 69: 4471-4483, 1995.
72. Théodore, L., D. Derossi, G. Chassaing, B. Llirbat, M. Kubes, P. Jordan, H. Chneiweiss, P. Godement, and A. Prochiantz. "Intraneuronal delivery of protein kinase C pseudosubstrate leads to growth cone collapse." *J. Neurosci.* 15: 7158-7167, 1995.
73. Turner, A., B. Bruun, T. Minson, and H. Browne. "Glycoproteins gB, gD, and gHgL of herpes simplex virus type I are necessary and sufficient to mediate membrane fusion in a Cos cell transfection system." *J. Virol.* 72: 873-875, 1998.
74. Visalli, R. J., and C. R. Brandt. "The HSV-1 UL45 18 kDa gene product is a true late protein and a component of the virion." *Virus Res.* 29: 167-178, 1993.
75. Vivès, E., P. Brodin, and B. Lebleu. "A truncated HIV-1 tat protein basic domain rapidly translocates through the plasma membrane and accumulates in the cell nucleus." *J. Biol. Chem.* 272: 16010-16017, 1997.
76. Vivès, E., Granier, C., Prevot, P., and Lebleu, B. "Structure-activity relationship study of the plasma membrane translocating potential of a short peptide from HIV-1 tat protein." *Lett. Pept. Sci.* 4, 429-436, 1997.
77. Westra, D. F., K. L. Glazenburg, M. C. Harmsen, A. Tiran, A. Jan Scheffer, G. W. Welling, T. Hauw The, and S Welling-Wester. "Glycoprotein H of herpes simplex virus type 1 requires glycoprotein L for transport to the surfaces of insect cells." *J. Virol.* 71: 2285-2291, 1997.
78. Whitbeck, J. C., C. Peng, H. Lou, R. Xu, S. H. Willis, M. Ponce de Leon, T. Peng, A. V. Nicola, R. I. Montgomery, M. S. Warner, A. M. Soulika, L. A. Spruce, W. T. Moore, J. D. Lambris, P. G. Spear, G. H. Cohen, and R. J. Eisenberg. "Glycoprotein D of herpes simplex virus (HSV) binds directly to HVEM, a member of the tumor necrosis factor receptor superfamily and a mediator of HSV entry." *J. Virol.* 71: 6083-6093, 1997.
79. White, J. "Membrane fusion." *Science* 258: 917-923, 1992.
80. Whitley, R. J. "Epidemiology of herpes simplex viruses," p. 1-44. In B. Roizman, (ed), The Herpesviruses, Volume 3. Plenum Press, New York, N.Y., 1982.
81. Wild C, T. Oas, C. McDanal, D. Bolognesi, and T. Matthews. "A synthetic peptide inhibitor of human immunodeficiency virus replication: Correlation between solution structure and viral inhibition." *Proc. Natl. Acad. Sci. USA* 89: 10537-10541, 1992.
82. WuDunn, D., and P. G. Spear. "Initial interaction of herpes simplex virus with cells is binding to heparan sulfate." *J. Virol.* 63: 52-58, 1989.
83. Yao, Q and R. W. Compans. "Peptides corresponding to the heptad repeat sequence of human parainfluenza virus fusion protein are potent inhibitors of virus infection." *Virology* 223: 103-112, 1996.

What is claimed is:

1. A method of inhibiting an influenza infection in a mammal comprising administering an effective amount of a peptide consisting of SEQ ID NO: 1 to a mammal having or suspected of having an influenza infection, wherein the peptide has an amino terminus selected from the group consisting of an $NH_2$ group and a biotin-aminohexanoyl group.

2. The method according to claim 1 wherein the peptide is administered with a pharmaceutically acceptable carrier.

3. The method according to claim 1, wherein the peptide is administered to the mammal's respiratory system.

4. The method according to claim 1, wherein the peptide is administered via inhalation.

5. The method according to claim 4, wherein the peptide is administered intranasally.

6. The method according to claim 1, wherein the antiviral peptide is administered after the mammal has been exposed to a virus that is capable of causing the viral respiratory infection.

7. The method according to claim 1, wherein the antiviral peptide is administered to the mammal at about the time the mammal is exposed to a virus that is capable of causing the viral respiratory infection.

8. The method according to claim 1, further comprising re-administering the peptide one or more times to the mammal.

9. The method according to claim 8, wherein at least one of the re-administrations occurs within about two to four hours of the previous administration.

10. The method according to claim 8, wherein at least one of the re-administrations occurs after there is substantially no free peptide present in the respiratory system.

11. The method according to claim 1, wherein the peptide backbone consists of d-amino acids.

12. The method of claim 1, wherein the mammal is a human.

13. A method of inducing resistance to influenza infection in a mammalian cell comprising:
(a) contacting one or more mammalian cells with an effective amount of at least one peptide consisting of SEQ ID NO: 1, wherein the peptide has an amino terminus selected from the group consisting of an $NH_2$ group and a biotin-aminohexanoyl group; and
(b) removing free peptide from the presence of the mammalian cells, wherein at least a portion of the one or more mammalian cells are resistant to influenza infection after (b);

(c) contacting one or more of the mammalian cells with one or more influenza viruses.

14. The method of claim 13 further comprising:

(d) measuring the influenza infection of the mammalian cells resulting from (c).

15. The method of claim 13, wherein (b) is performed by washing away the free peptide.

16. The method of claim 13, wherein (b) occurs by a biological process.

17. The method of claim 13 wherein the one or more mammalian cells are in vitro or in vivo.

18. A method of inducing resistance to influenza infection in a mammalian cell comprising:

(a) contacting one or more infectious influenza viruses with an effective amount of at least one peptide in the absence of a mammalian cell thereby rendering the one or more infectious influenza viruses less infectious, wherein the at least one peptide consists of SEQ ID NO: 1 and has an amino terminus selected from the group consisting of an $NH_2$ group and a biotin-aminohexanoyl group.

19. The method of claim 18 further comprising:

(b) contacting the one or more influenza viruses with one or more mammalian cells after (a).

20. The method of claim 19, wherein the one or more mammalian cells are in vitro or in vivo.

21. The method of claim 1 wherein the amino terminus of the peptide is an $NH_2$ group.

22. The method of claim 13 wherein the amino terminus of the peptide is an $NH_2$ group.

23. The method of claim 18 wherein the amino terminus of the peptide is an $NH_2$ group.

24. The method of claim 1, wherein the influenza infection is an influenza A infection.

25. The method of claim 13, wherein the influenza infection is an influenza A infection.

26. The method of claim 18, wherein the influenza infection is an influenza A infection.

27. A method of inhibiting an influenza infection in a mammal comprising administering an effective amount of a peptide consisting of SEQ ID NO: 1 to the respiratory system of a mammal having, suspected of having, or at risk for an influenza infection, wherein the peptide has an amino terminus selected from the group consisting of an $NH_2$ group and a biotin-aminohexanoyl group.

28. The method of claim 27, wherein the mammal is a human.

29. The method of claim 27, wherein the influenza infection is an influenza A infection.

30. The method according to claim 27, wherein the peptide is administered prophylactically.

* * * * *

UNITED STATES PATENT AND TRADEMARK OFFICE
CERTIFICATE OF CORRECTION

PATENT NO. : 7,432,045 B2
APPLICATION NO. : 11/001674
DATED : October 7, 2008
INVENTOR(S) : Curtis R. Brandt et al.

It is certified that error appears in the above-identified patent and that said Letters Patent is hereby corrected as shown below:

In the Specification

Column 1, Lines 14-16:
Delete the phrase:
"This invention was made with United States government support awarded by the following agencies: NIH AI52049. The United States has certain rights in this invention."
And replace with:
--This invention was made with government support under AI052049 awarded by the National Institutes of Health. The government has certain rights in the invention.--.

Signed and Sealed this
Eighth Day of December, 2020

Andrei Iancu
*Director of the United States Patent and Trademark Office*